US008536185B2

(12) United States Patent
Endres et al.

(10) Patent No.: US 8,536,185 B2
(45) Date of Patent: Sep. 17, 2013

(54) MULTIHETEROARYL COMPOUNDS AS INHIBITORS OF H-PGDS AND THEIR USE FOR TREATING PROSTAGLANDIN D2 MEDIATED DISEASES

(75) Inventors: Gregory W. Endres, Saline, MI (US); Pil Heui Lee, Chelsea, MI (US); Kirk Lang Olson, Canton, MI (US); James Bernard Kramer, Sylvania, OH (US); Fred Lawrence Ciske, Dexter, MI (US); Stephen Douglas Barrett, Hartland, MI (US)

(73) Assignee: Cayman Chemical Company, Incorporated, Ann Arbor, MI (US)

( * ) Notice: Subject to any disclaimer, the term of this patent is extended or adjusted under 35 U.S.C. 154(b) by 430 days.

(21) Appl. No.: 12/564,582

(22) Filed: Sep. 22, 2009

(65) Prior Publication Data

US 2010/0075990 A1 Mar. 25, 2010

Related U.S. Application Data

(60) Provisional application No. 61/098,942, filed on Sep. 22, 2008.

(51) Int. Cl.
*A61K 31/44* (2006.01)
*C07D 401/04* (2006.01)
*C07D 239/42* (2006.01)
*C07D 239/02* (2006.01)

(52) U.S. Cl.
USPC ........... 514/256; 514/340; 544/333; 544/335; 546/272.7

(58) Field of Classification Search
USPC ....... 514/256, 340; 544/333, 335; 546/272.7
See application file for complete search history.

(56) References Cited

U.S. PATENT DOCUMENTS

| 4,435,396 | A | 3/1984 | LaMattina et al. |
| 6,005,116 | A | 12/1999 | Kojima et al. |
| 7,238,718 | B2 | 7/2007 | Urade et al. |
| 7,547,532 | B2 | 6/2009 | Urade et al. |
| 7,951,956 | B2 | 5/2011 | Urade et al. |
| 2005/0154024 | A1 | 7/2005 | Bryans et al. |
| 2005/0272767 | A1 | 12/2005 | Urade et al. |
| 2008/0146569 | A1 | 6/2008 | Blake et al. |
| 2008/0207651 | A1 | 8/2008 | Blake et al. |
| 2008/0227782 | A1 | 9/2008 | Aldous et al. |

FOREIGN PATENT DOCUMENTS

| EP | 0257897 A1 | 3/1988 |
| EP | 0504888 A1 | 9/1992 |
| WO | WO 96-32938 A1 | 10/1996 |
| WO | WO9632938 | 10/1996 |
| WO | WO 97-31906 A1 | 9/1997 |
| WO | WO9731906 | 9/1997 |
| WO | WO 97-36901 A1 | 10/1997 |
| WO | WO9736901 | 10/1997 |
| WO | 01-52845 A1 | 7/2001 |
| WO | WO0152846 A1 | 7/2001 |
| WO | WO03027096 A1 | 4/2003 |
| WO | WO03027101 A1 | 4/2003 |
| WO | WO03087045 A1 | 10/2003 |
| WO | WO2004005283 A1 | 1/2004 |
| WO | WO2004043926 A1 | 5/2004 |
| WO | WO2004060367 A1 | 7/2004 |
| WO | WO2004069394 A2 | 8/2004 |
| WO | WO2005003099 A2 | 1/2005 |
| WO | WO2005012298 A1 | 2/2005 |
| WO | WO2005028452 A1 | 3/2005 |
| WO | WO2005047281 A1 | 5/2005 |
| WO | WO2005058848 A1 | 6/2005 |
| WO | WO2005061489 A1 | 7/2005 |
| WO | 2005-075468 A2 | 8/2005 |
| WO | WO 2005-080382 A1 | 9/2005 |
| WO | WO 2005-087764 A1 | 9/2005 |
| WO | WO 2005-094805 A1 | 10/2005 |
| WO | WO2005094805 A1 | 10/2005 |
| WO | WO 2006-108701 A1 | 10/2006 |
| WO | WO 2007/007778 A1 | 1/2007 |
| WO | WO2007007778 A1 | 1/2007 |
| WO | 2007-040440 A1 | 4/2007 |
| WO | WO 2007-041634 A1 | 4/2007 |
| WO | WO2007041634 A1 | 4/2007 |
| WO | WO2007087427 A2 | 8/2007 |
| WO | WO2007113276 A1 | 10/2007 |
| WO | WO 2007-125061 A1 | 11/2007 |
| WO | WO 2007-129052 A1 | 11/2007 |
| WO | WO2007129052 A1 | 11/2007 |
| WO | 2008-021928 A2 | 2/2008 |
| WO | WO 2008/029306 A2 | 3/2008 |
| WO | WO 2008-075172 A2 | 6/2008 |
| WO | WO2008075172 A2 | 6/2008 |
| WO | WO 2008-104869 A1 | 9/2008 |

(Continued)

OTHER PUBLICATIONS

Gao, et al., Rapid Communication: Prostaglandin D2 Produced by Hematopoietic Prostaglandin D Synthase Contributes to LPS-Induced Fever, Journal of Physiology and Pharmacology 2009, vol. 60, No. 2, pp. 145-150.

Palanki et al., Structure-Activity Relationship Studies of Ethyl 2-[3-Methyl-2,5-dioxo(3-pyrrolinyl))amino]-4-(trifluoromethyl)pyrimidine-5-carboxylate: An Inhibitor of AP-1 and NF-κB Mediated Gene Expression, Bioorganic & Medicinal Chemistry Letters, 12 (2002) 2573-2577.

Boulos J et al.: "Synthesis of Oxasolyland Furanyl-Substituted Imidazole Hydrochlorides and Methiodides" Journal of Heterocyclic Chemistry, Wiley-Blackwell Publishing, Inc., US, vol. 35, No. 4, Jul. 1, 1998, pp. 859-863, XP001017982, ISSN: 0022-152X, DOI: 10.1002/JHET.5570350413 *p. 860; example 13a*.

Zhang W et al.: "Structure and isomerization in 4,4'-biimidazoles: a comparison of crystal structures and theoretical calculations of 2,2'-dimethyl-4,4'-biimidazole and 2,2'-dimethyl-4,4'-biimidazolium bis-trifluoroactate", Thetrahedron, Elsevier Science Publishers, Amsterdam, NL, vol. 59, No. 32, Aug. 4, 2003, pp. 6027-6034, XP004442545, ISSN: 0040-4020, DOI: 10.1016/S0040-4020 (03) 00987-6 *p. 6028; compound 1*.

English language abstract for WO 1997-031906 published on Sep. 4, 1997; extracted from the espacenet.com database on Dec. 5, 2012; 249 pages.

English language abstract for WO 2005-094805 published on Oct. 13, 2005, extracted from the espacenet.com database on Dec. 5, 2012; 234 pages.

English language abstract for WO 2007-007778 published on Jan. 18, 2007; extracted from the espacenet.com database on Dec. 5, 2012; 125 pages.

(Continued)

*Primary Examiner* — James O Wilson
*Assistant Examiner* — Ebenezer O Sackey
(74) *Attorney, Agent, or Firm* — Howard & Howard Attorneys PLLC

(57) ABSTRACT

Multiheteroaryl compounds, their preparation, pharmaceutical compositions comprising these compounds, and their pharmaceutical use in the prevention and treatment of prostaglandin $D_2$ mediated diseases and conditions that may be modulated by the inhibition of hematopoietic prostaglandin D synthase (H-PGDS).

57 Claims, No Drawings

(56) References Cited

FOREIGN PATENT DOCUMENTS

| WO | WO2008104869 A1 | 9/2008 |
|---|---|---|
| WO | WO2008121670 A1 | 10/2008 |
| WO | WO2008128951 A1 | 10/2008 |
| WO | WO 2009/051556 A1 | 4/2009 |
| WO | WO 2009-051556 A1 | 4/2009 |

OTHER PUBLICATIONS

Pinzar, et al., Prostaglandin D Synthase Gene is Involved in the Regulation of Non-Rapid Eye Movement Sleep, Apr. 25, 2000, vol. 97, No. 9, pp. 4903-4907.

Kapoor, et al., Sequential Induction of Pro- and Anti-inflammatory Prostaglandins and Perioxisome Proliferators Activated Receptor-Gamma During Normal Wound Healing: A Time Course Study, NIH Public Access—Author Manuscript, Prostaglandins Leukor Essent Fatty Acids, Feb. 2007; 76(2): 103-112.

Urade, et al., Purification and Characterization of Rat Brain Prostaglandin D Synthetase, The Journal of Biological Chemistry, vol. 260, No. 23, Issue of Oct. 15, pp. 12410-12415, 1985.

Spik, et al., Activation of the Prostaglandin D2 Receptor DP2/CRTH2 Increases Allergic Inflammation in Mouse1, The Journal of Immunology, 2005 174, pp. 3703-3708.

Urade, et al., Prostaglandin D. Synthase: Structure and Function, Vitamins and Hormones, 2000, vol. 58, pp. 89-120.

Kanaoka, et al., Cloning and Crystal Structure of Hematopoietic Prostaglandin D Synthase, Cell, 1997, vol. 90, pp. 1085-1095.

Herlong, et al., Positioning Prostanoids of the D and J series in the Immunopathogenic Scheme, Immunology Letters, 102, 2006 pp. 121-131.

Gao, et al., Rapid Communication: Prostaglandin D2 Produced by Hematopoietic Prostaglandin D Synthase Contributes to LPS-Induced Fever, Journal of Physiology and Pharmacology 2009, vol. 60, No. 2 pp. 145-150.

Eguchi et al., Lack of Tactile Pain (Allodynia) in Lipocalin-Type Prostaglandin D Synthase-Deficient Mice, Proc. Natl. Acad. Sci. USA, vol. 96, pp. 726-730, Jan. 1999, Neurobiology.

Kanaoka et al., Hematopoietic Prostaglandin D Synthase, Prostaglandins, Leukotrienes and Essential Fatty Acids, 69 (2003) 163-167.

Mohri et al., Inhibition of Prostaglandin D Synthase Suppresses Muscular Necrosis, The American Journal of Pathology, vol. 174, No. 5, May 2009, pp. 1735-1744.

Ikai, et al., Inhibitory Effect of Tranilast on Prostaglandin D Synthase, Biochemical Pharmacology, vol. 38, No. 16, pp. 2673-2676, 1989.

Urade, et al., Biochemical and Structural Characteristics of Hematopoietic Prostaglandin D Synthase: From Evolutionary Analysis to Drug Designing, Transworld Research Network, Functional and Structural Biology on the Lipo-Network, 2006: 135-164 ISBN: 81-7895-232-7.

Matsushita et al., Pharmacological Studies on the Novel Antiallergic Drug HGL-79: I. Antiallergic and Aniasthmatic Effects in Various Experimental Models, Japan Journal Pharmacology, vol. 78, pp. 1-10 (1998).

Matsushita et al., Pharmacological Studies on the Novel Antiallergic Drug HQL-79: II. Elucidation of Mechanisms for Antiallergic and Antiasthmatic Effects, Japan, Pharmacology 78 pp. 11-22 (1998).

Palanki et al., Structure-Activity Relationship Studies of Ethyl 2-[3-Methyl-2,5-dioxo(3-pyrrolinyl))amino]-4-(trifluoromethyl)pyrimidine-5-carboxylate: An Inhibitor of AP-1 and NF-kB Mediated Gene Expression, Bioorganic & Medicinal Chemistry Letters, 12 (2002) 2573-2577.

Tanaka et al., Studies on Antiplatelet Agents. I. Synthesis and Platelet Inhibitory Activity of 5-Aljy1-2-aryl-4-pyridylimidazoles1) Chem. Parhm. Bull. 40(12) 3206-3213 (1992).

Hohwy, et al., Novel Prostaglandin D Synthase Inhibitors Generated by Fragment-Based Drug Design, Journal Medical Chemical 2008, 51, pp. 2178-2186.

Matthews, et al., Synthase and Cardiotonic Activity of Novel Biimidazoles, Journal Medical Chem. 1990, 33, pp. 317-327.

Nuriev, et al., Synthetic Pathways to a Family of Pyridine-Containing Azoles-Promising Ligands for Coordination Chemistry, ARKIVOC, 2005 (iv) pp. 208-224.

2-Phenoxypyrimidine-5-carbonxamide derivatives as a novel Prostaglandin D Synthase Inhibitor, 235th ACS Mtg., TAIHO Pharmaceutical Co., LTD.

MULTIHETEROARYL COMPOUNDS AS INHIBITORS OF H-PGDS AND THEIR USE FOR TREATING PROSTAGLANDIN D2 MEDIATED DISEASES

CROSS REFERENCE TO RELATED APPLICATIONS

The present invention claims priority from U.S. Provisional Application No. 61/098,942 filed Sep. 22, 2008 entitled "Multiheterocyclic Compounds for the Treatment of Allergy, Inflammation, and Immune Disorders."

FIELD OF THE INVENTION

Multiheteroaryl compounds, their preparation, pharmaceutical compositions comprising these compounds, and their pharmaceutical use in the prevention and treatment of prostaglandin $D_2$ mediated diseases and conditions that may be modulated by the inhibition of hematopoietic prostaglandin D synthase (H-PGDS).

BACKGROUND OF THE INVENTION

Allergic and inflammatory disorders such as allergic rhinitis, asthma, chronic obstructive pulmonary disease (COPD), allergic conjunctivitis, and atopic dermatitis affect roughly one-fifth of the world population. Symptoms arising from antigenic challenge, including bronchoconstriction, bronchial hyperactivity, sneezing, nasal discharge, and nasal congestion, have been shown to correspond with the release of multiple mediators from inflammatory cells. Current therapies that effectively treat some of these symptoms have arisen out of compound classes including antihistamines, leukotriene antagonists, and corticosteroids. Many existing medicines suffer from side effects such as headache, sleepiness, sedation, dyspepsia, hydrodipsia, pharyngitis, and oral candidiasis. In addition, many of these individual therapies, although treating some symptoms, may fail to address a broader range of symptoms that affect patient quality of life. Antihistamines, for example, treat some of the most unpleasant symptoms of allergy, but have little therapeutic benefit against nasal congestion.

Immunological challenge results in the release of prostaglandin $D_2$ ($PGD_2$), the primary allergic and inflammatory mediator, from inflammatory cells. $PGD_2$, a metabolite of arachidonic acid, activates both the $DP_1$ (DP) and $DP_2$ (CRTH2) receptors, which play a central role in airway inflammation (Spik, I., Brenuchon, C., Angeli, V., et al. *J. Immunol.*, 174, 2005, 3703-3708; Urade, Y., Hayaishi, O. *Vitamin and Hormones*, 58, 2000, 89-120).

Prostaglandin D synthase (PGDS) catalyzes the conversion of the common prostanoid precursor prostaglandin $H_2$ ($PGH_2$) to $PGD_2$. Two distinct forms of PGDS, lipocalin PGDS (L-PGDS) and hematopoietic PGDS (H-PGDS) have been identified and characterized (Kapoor, M., Kojima, F., Yang, L., and Crofford, L. J. *Prostaglandins Leukot. Essent. Fatty Acids*, 76(2), 2007, 103-112; Herlong, J. L., Scott, T. R. *Immunology Letters*, 102, 2006, 121-131; Urade, Y., Fujimoto, N., and Hayaishi, O. *J. Biol. Chem.*, 260, 1985, 12410-12415; Kanaoka, Y., Ago, H., Inagaki, E., et al. *Cell*, 90, 1997, 1085-1095).

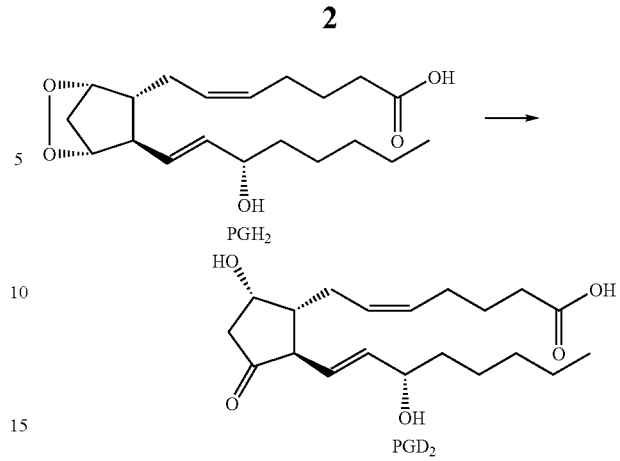

L-PGDS is a glutathione-independent 26 kDa secretory protein that is regarded as the major generator of $PGD_2$ in the central nervous system. L-PGDS is involved in the regulation of sleep (Pinzar, E., Kanaoka, Y., Inui, T., Eguchi, N., Urade, Y., and Hayaishi, O. *Proc. Natl. Acad. Sci. U.S.A.*, 97, 2000, 4903-4907) and pain (Eguchi, N., Minami, T., Shirafuji, N., et al. *Proc. Natl. Acad. Sci. U.S.A.*, 96, 1999, 726-730).

H-PGDS is a 26 kDa cytosolic protein that catalyzes the conversion of $PGH_2$ to $PGD_2$ in a glutathione-dependent manner. This sigma class glutathione S-transferase (GST) is localized in mast cells, antigen-presenting cells, and Th2 cells, and is involved in allergic and inflammatory response (Urade, Y., Mohri, I., Aritake, K., Inoue, T., Miyano, M. *Functional and Structural Biology on the Lipo-network*, 2006, 135-164; Kanaoka, Y., Urade, Y. *Prostaglandins Leukot. Essent. Fatty Acids*, 69, 2003, 163-167).

H-PGDS inhibition provides a novel method for preventing and/or treating allergic and respiratory diseases or conditions through the suppression of $PGD_2$ synthesis. Most current therapies function subsequent to mast cell activation and/or degranulation and the formation and release of $PGD_2$. H-PGDS inhibitors, however, have been found to block the formation of $PGD_2$ in vitro (Ikai, K., Ujihara, M., Fujii, K., Urade, Y. *Biochemical Pharmacology*, 38(16), 1989, 2673-2676). In addition, the weak H-PGDS inhibitor HQL-79 has shown antiallergic and antiasthmatic activity in vivo (Matsushita, N., Hizue, M., Aritake, K., et al. *Jpn. J. Pharmacol.*, 78, 1998, 1-10; Matsushita, N., Aritake, K., Takada, A., et al. *Jpn. J. Pharmacol.*, 78, 1998, 11-22). Other PGDS inhibitors have been reported (US Patent Application No. US 2008/0146569 A1; PCT International Application No. WO 2007/041634 A1; PCT International Application No. WO 2005/094805 A1; PCT International Application No. WO 2007/007778).

Evidence suggests that the modulation of H-PGDS activity should be of therapeutic benefit in indications related to elevated $PGD_2$ levels. These indications include, but are not limited to, allergic rhinitis, perennial rhinitis, rhinorrhea, nasal congestion, nasal inflammation, all types of asthma, COPD, allergic conjunctivitis, arthritis, atopic dermatitis and other types of dermal inflammation, ocular inflammation, wound healing, dermal scarring, and muscular necrosis (i.e. Duchenne muscular dystrophy; *American Journal of Pathology*, 174(5), 2009, 1735-1744). Efficacious doses of H-PGDS inhibitors may provide both therapeutic benefits and improved safety profiles over existing therapies used for these indications. Recent evidence also suggests that $PGD_2$ produced by H-PGDS plays a role in fever induction (*Journal of Physiology and Pharmacology,* 60(2), 2009, 145-150).

Compounds have now been found that are inhibitors of H-PGDS, and at expected efficacious doses, do not significantly inhibit L-PGDS.

SUMMARY OF THE INVENTION

The exemplary embodiments may be directed to multiheterocyclic (multiheteroaryl) compounds of structural formulas (I) or (II), respectively, that may be used to treat or prevent allergic, inflammatory, and/or immune disorders, including the prevention and treatment of prostaglandin $D_2$ mediated diseases and conditions that may be modulated by the inhibition of hematopoietic prostaglandin D synthase (H-PGDS), wherein $R^1$, $R^2$, $U^1$, $U^2$, $U^3$, $U^4$, $Y^1$, $Y^2$, $Y^3$, $Y^4$, and W, are defined herein:

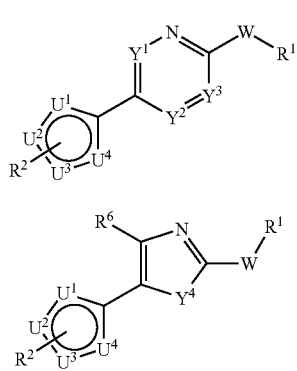

Another aspect of the exemplary embodiments may be a pharmaceutical composition comprising a pharmaceutically effective amount of a compound according to either of formulas (I) or (II), or an equivalent thereof, or an N-oxide thereof, or a pharmaceutically acceptable salt or solvate thereof, in admixture with a pharmaceutically acceptable carrier.

Another aspect of the exemplary embodiments may be directed to a method of treating immunological disorders, particularly allergic and/or inflammatory disorders, and more particularly disorders such as allergic rhinitis, asthma, chronic obstructive pulmonary disease (COPD), arthritis, dermal inflammation, ocular inflammation, wound healing, and dermal scarring in a patient in need thereof by administering to the patient a compound according to either formula (I) or (II), or a hydrate, solvate, or N-oxide thereof, or a pharmaceutically acceptable salt thereof.

DETAILED DESCRIPTION OF THE INVENTION

The exemplary embodiments may be directed bicyclic heteroaryl compounds of formulas (I) or (II), respectively, their preparation, pharmaceutical compositions comprising these compounds, and their pharmaceutical use in the prevention and treatment of prostaglandin $D_2$ mediated diseases and conditions that may be modulated by the inhibition of hematopoietic prostaglandin D synthase (H-PGDS).

The compound of formula (I), according to one exemplary embodiment, is shown below:

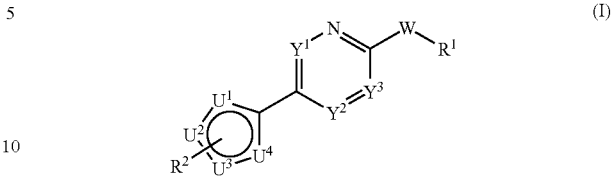

wherein:

$R^1$ is $(C_1\text{-}C_6)$-alkyl, $(C_3\text{-}C_6)$-cycloalkyl, phenyl, 2-pyridyl, 3-pyridyl, or 4-pyridyl; wherein each phenyl, 2-pyridyl, 3-pyridyl, or 4-pyridyl of $R^1$ may be optionally substituted with no more than two of each or a combination of fluoro, hydroxy, —$CH_2OH$, carboxy, carboxymethyl, or carboxyethyl;

$R^2$ is —$(CH_2)_n Z^1$ or —$(CH_2)_n Z^2$;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1\text{-}C_6)$-alkyl, $(C_3\text{-}C_6)$-cycloalkyl, $(C_3\text{-}C_6)$-alkenyl, $(C_3\text{-}C_6)$-alkynyl, $(C_6\text{-}C_{14})$-aryl, $(CH_2)_p CF_3$, a five- to ten-membered heteroaryl,

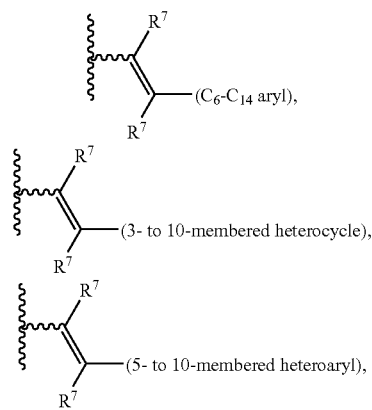

or a three- to ten-membered heterocycle; wherein any one nitrogen atom of any heterocycle containing one or more nitrogen atoms that may be substituted with a non-ring atom are substituted with —$(CH_2)_q Q$;

$Z^2$ is cyano, trifluoromethyl, $(CF_2)_p CF_3$, $SR^3$, $NR^4R^5$, $N(H)C(O)R^3$, $N(H)CO_2R^3$, $N(H)C(O)NR^4R^5$, $N(H)SO_2R^3$, vinyl, or ethynyl when n is 1, 2, 3 or 4;

$Z^2$ may also be cyano, trifluoromethyl, $(CF_2)_p CF_3$, $SR^3$, $NR^4R^5$, $N(H)C(O)R^3$, $N(H)CO_2R^3$, $N(H)C(O)NR^4R^5$, $N(H)SO_2R^3$, vinyl, or ethynyl when n is 0, except when $R^2$ is covalently bonded to a $U^1$, $U^2$, $U^3$, or $U^4$ that is a nitrogen atom;

$R^3$ is hydrogen, $(C_1\text{-}C_6)$-alkyl, trifluoromethyl, $(C_3\text{-}C_6)$-alkenyl, $(C_3\text{-}C_6)$-alkynyl, $(CH_2)_m(C_3\text{-}C_6)$-cycloalkyl, $(CH_2)_m$ phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_q Q$;

m is 0, 1, 2, 3, or 4;

q is 0, 1, 2, 3, or 4;

Q is hydrogen, $(C_1\text{-}C_6)$-alkyl, $(CH_2)_p CF_3$, $(C_3\text{-}C_6)$-alkenyl, $(C_3^{-C}_6)$-alkynyl, $(C_3\text{-}C_6)$-cycloalkyl, $(C_6\text{-}C_{14})$-aryl, C(O)R$^3$, CO$_2$R$^3$, C(O)NR$^4$R$^5$, a three- to six-membered heterocycle, or a five- to ten-membered heteroaryl when q is 0, 1, 2, 3, or 4;

Q may also be cyano, trifluoromethyl, or SO$_2$NR$^4$R$^5$ when q is 1, 2, 3, or 4;

Q may also be hydroxy, (C$_1$-C$_6$)-alkoxy, sulfhydryl, —S—(C$_1$-C$_6$)-alkyl, or NR$^4$R$^5$ when q is 2, 3, or 4;

p is 1, 2, or 3;

R$^3$ may also be vinyl or ethynyl when R$^3$ is not covalently bonded to an N or O atom;

R$^3$ may also be vinyl or ethynyl when R$^3$ is not covalently bonded to an S atom possessing a −2 (minus 2) oxidation state;

R$^4$ and R$^5$ are independently hydrogen, (C$_1$-C$_6$)-alkyl, (C$_3$-C$_6$)-alkenyl, (C$_3$-C$_6$)-alkynyl, (CH$_2$)$_m$(C$_3$-C$_6$)-cycloalkyl, (CH$_2$)$_m$phenyl, (CH$_2$)$_m$-(three- to ten-membered heterocycyl), or (CH$_2$)$_m$-(five- to ten-membered heteroaryl);

the NR$^4$R$^5$ group of any C(O)NR$^4$R$^5$, SO$_2$NR$^4$R$^5$, NR$^4$R$^5$, or N(H)C(O)NR$^4$R$^5$ may also form a pyrrolidine, a piperidine, a morpholine, a thiomorpholine, or a thiomorpholine S-dioxide;

the NR$^4$R$^5$ group of any C(O)NR$^4$R$^5$, SO$_2$NR$^4$R$^5$, NR$^4$R$^5$, or N(H)C(O)NR$^4$R$^5$ may also form a piperazine ring, wherein the other nitrogen atom of the piperazine ring is substituted with hydrogen, (C$_1$-C$_6$)-alkyl, CH$_2$CF$_3$, (C$_3$-C$_6$)-cycloalkyl, CH$_2$(C$_3$-C$_6$)-cycloalkyl, phenyl, benzyl, hydroxyethyl, or hydroxypropyl;

phenyl or heteroaryl rings of Z$^1$ and Z$^2$ are optionally substituted with one-to-three of any one or combination of the following: halo, hydroxy, sulfhydryl, (C$_1$-C$_3$)-alkoxy, (C$_1$-C$_3$)-alkyl, (C$_i$-C$_3$)-alkylthio, trifluoromethyl, trifluoromethoxy, cyano, carboxy, carboxy(C$_1$-C$_3$)-alkyl, carbamoyl, or sulfamoyl;

W is a covalent bond, O, S, SO, SO$_2$, CH$_2$, CHOH, CO, or NH;

U$^1$, U$^2$, U$^3$, U$^4$, and a carbon atom form a five-membered heteroaryl ring; wherein one of U$^1$, U$^2$, U$^3$, and U$^4$ of the five-membered heteroaryl ring is covalently bonded to the R$^2$ group; wherein the U$^1$, U$^2$, U$^3$, or U$^4$ that is covalently bonded to the R$^2$ group is a carbon atom or a nitrogen atom; wherein when the U$^1$, U$^2$, U$^3$, or U$^4$ that is covalently bonded to the R$^2$ group is a nitrogen atom, one, two, or all of the other three of the group consisting of U$^1$, U$^2$, U$^3$, and U$^4$ is N and each remaining of the group consisting of U$^1$, U$^2$, U$^3$, and U$^4$ that is not N is C—R$^6$; wherein when the U$^1$, U$^2$, U$^3$, or U$^4$ that is covalently bonded to the R$^2$ group is a carbon atom, one of the other three of the group consisting of U$^1$, U$^2$, U$^3$, and U$^4$ is N—R$^6$, O, or S, and each of remaining of the group consisting of U$^1$, U$^2$, U$^3$, and U$^4$ is C—R$^6$ or N;

Y$^1$, Y$^2$, Y$^3$, a nitrogen atom, and two carbon atoms form a six-membered heteroaryl ring; wherein no more than one of the group consisting of Y$^1$, Y$^2$, and Y$^3$ is N; and wherein all Y$^1$, Y$^2$, and Y$^3$ that are not N are C—R$^6$;

each R$^6$ is independently hydrogen, methyl, trifluoromethyl, or amino; and each R$^7$ is independently hydrogen or methyl;

or an equivalent thereof, or an N-oxide thereof, or a pharmaceutically acceptable salt or solvate thereof.

Another exemplary embodiment may be directed to a compound of formula (II):

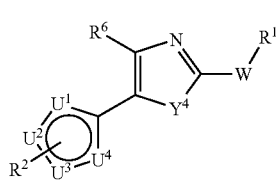

(II)

wherein:

R$^1$ is (C$_1$-C$_6$)-alkyl, (C$_3$-C$_6$)-cycloalkyl, phenyl, 2-pyridyl, 3-pyridyl, or 4-pyridyl; wherein each phenyl, 2-pyridyl, 3-pyridyl, or 4-pyridyl of R$^1$ may be optionally substituted with no more than two of each or a combination of fluoro, hydroxy, —CH$_2$OH, carboxy, carboxymethyl, or carboxyethyl;

R$^2$ is —(CH$_2$)$_n$Z$^1$ or —(CH$_2$)$_n$Z$^2$;

n is 0, 1, 2, 3, or 4;

Z$^1$ is hydrogen, OR$^3$, C(O)R$^3$, CO$_2$R$^3$, C(O)NR$^4$R$^5$, SO$_2$NR$^4$R$^5$, SO$_2$R$^3$, (C$_1$-C$_6$)-alkyl, (C$_3$-C$_6$)-cycloalkyl, (C$_3$-C$_6$)-alkenyl, (C$_3$-C$_6$)-alkynyl, (C$_6$-C$_{14}$)-aryl, (CH$_2$)$_p$CF$_3$, a five- to ten-membered heteroaryl,

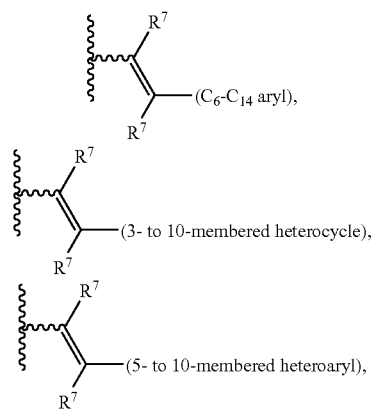

or a three- to ten-membered heterocycle; wherein any one nitrogen atom of any heterocycle containing one or more nitrogen atoms that may be substituted with a non-ring atom are substituted with —(CH$_2$)$_q$Q;

Z$^2$ is cyano, trifluoromethyl, (CF$_2$)$_p$CF$_3$, SR$^3$, NR$^4$R$^5$, N(H)C(O)R$^3$, N(H)CO$_2$R$^3$, N(H)C(O)NR$^4$R$^5$, N(H)SO$_2$R$^3$, vinyl, or ethynyl when n is 1, 2, 3 or 4;

Z$^2$ may also be cyano, trifluoromethyl, (CF$_2$)$_p$CF$_3$, SR$^3$, NR$^4$R$^5$, N(H)C(O)R$^3$, N(H)CO$_2$R$^3$, N(H)C(O)NR$^4$R$^5$, N(H)SO$_2$R$^3$, vinyl, or ethynyl when n is 0, except when R$^2$ is covalently bonded to a U$^1$, U$^2$, U$^3$, or U$^4$ that is a nitrogen atom;

R$^3$ is hydrogen, (C$_1$-C$_6$)-alkyl, trifluoromethyl, (C$_3$-C$_6$)-alkenyl, (C$_3$-C$_6$)-alkynyl, (CH$_2$)$_m$(C$_3$-C$_6$)-cycloalkyl, (CH$_2$)$_m$ phenyl, (CH$_2$)$_m$-(five- to ten-membered heteroaryl), or (CH$_2$)$_m$(three- to ten-membered heterocycle); wherein any one nitrogen atom of any heterocycle containing one or more nitrogen atoms that may be substituted with a non-ring atom are substituted with —(CH$_2$)$_q$Q;

m is 0, 1, 2, 3, or 4;

q is 0, 1, 2, 3, or 4;

Q is hydrogen, (C$_1$-C$_6$)-alkyl, (CH$_2$)$_p$CF$_3$, (C$_3$-C$_6$)-alkenyl, (C$_3$-C$_6$)-alkynyl, (C$_3$-C$_6$)-cycloalkyl, (C$_6$-C$_{14}$)-aryl, C(O)R$^3$, CO$_2$R$^3$, C(O)NR$^4$R$^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ and $Z^2$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

W is a covalent bond, O, S, SO, $SO_2$, $CH_2$, CHOH, CO, or NH;

$U^1$, $U^2$, $U^3$, $U^4$, and a carbon atom form a five-membered heteroaryl ring; wherein one of $U^1$, $U^2$, $U^3$, and $U^4$ of the five-membered heteroaryl ring is covalently bonded to the $R^2$ group; wherein the $U^1$, $U^2$, $U^3$, or $U^4$ that is covalently bonded to the $R^2$ group is a carbon atom or a nitrogen atom; wherein when the $U^1$, $U^2$, $U^3$, or $U^4$ that is covalently bonded to the $R^2$ group is a nitrogen atom, one, two, or all of the other three of the group consisting of $U^1$, $U^2$, $U^3$, and $U^4$ is N and each remaining of the group consisting of $U^1$, $U^2$, $U^3$, and $U^4$ that is not N is C—$R^6$; wherein when the $U^1$, $U^2$, $U^3$, or $U^4$ that is covalently bonded to the $R^2$ group is a carbon atom, one of the other three of the group consisting of $U^1$, $U^2$, $U^3$, and $U^4$ is N—$R^6$, O, or S, and each of remaining of the group consisting of $U^1$, $U^2$, $U^3$, and $U^4$ is C—$R^6$ or N;

$Y^4$ is O, S, or N—$R^7$;

each $R^6$ is independently hydrogen, methyl, trifluoromethyl, or amino; and each $R^7$ is independently hydrogen or methyl;

or an equivalent thereof, or an N-oxide thereof, or a pharmaceutically acceptable salt or solvate thereof.

A more specific subset of exemplary embodiments derived from formula (I) are shown below individually as formulas (III)-(XIX), respectively.

One such exemplary embodiment may be directed to a compound of formula (III)

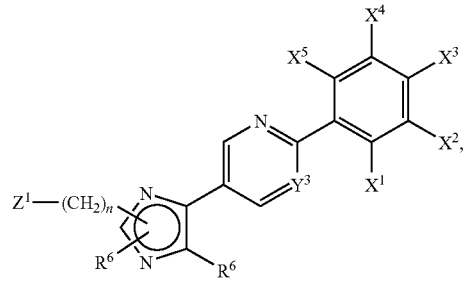

(III)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

$Y^3$ is CH or N;

each $R^6$ is independently hydrogen, methyl, trifluoromethyl, or amino;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_pCF_3$, a five- to ten-membered heteroaryl,

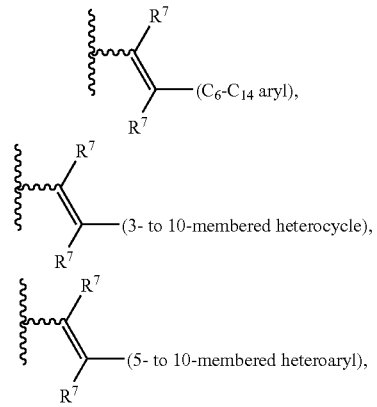

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$ phenyl, $(CH_2)_m$-(five- to ten-membered heteroaryl), or $(CH_2)_m$-(three- to ten-membered heterocycle); wherein any one nitrogen atom of any heterocycle containing one or more nitrogen atoms that may be substituted with a non-ring atom are substituted with —$(CH_2)_qQ$;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl; and $R^7$ is hydrogen or methyl;

or an equivalent thereof, or an N-oxide thereof, or a pharmaceutically acceptable salt or solvate thereof.

Another exemplary embodiment may be directed to a compound of formula (IV):

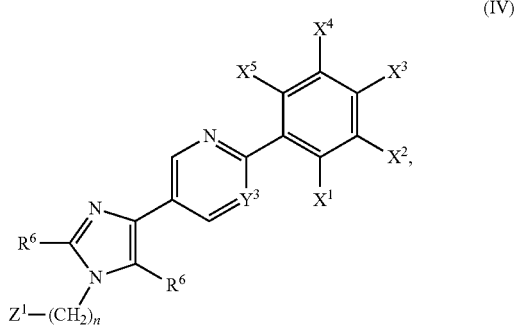

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, a $X^5$ are as defined above for a compound of Formula (III).

Another exemplary embodiment may be directed to a compound of formula (V):

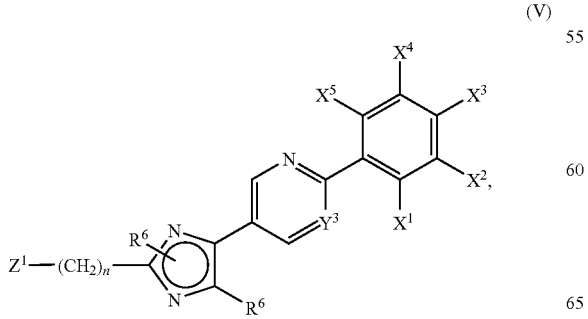

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, and $X^5$ are as defined above for a compound of Formula (IV).

Another exemplary embodiment may be directed to a compound of formula (VI):

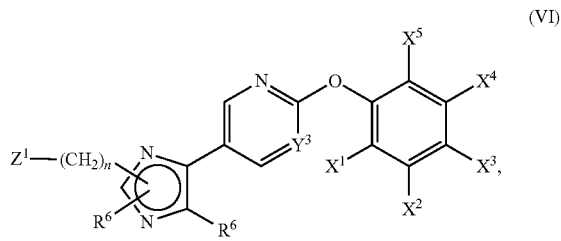

or an equivalent thereof, or an N-oxide thereof, or a pharmaceutically acceptable salt or solvate thereof, wherein each $X^1$, $X^2$, $X^3$, $X^4$, and $X^5$ is independently hydrogen or fluoro, with no more than two of $X^1$, $X^2$, $X^3$, $X^4$, and $X^5$ being fluoro; and wherein n, $Z^1$, $R^6$, and $Y^3$ are as defined above for a compound of Formula (I).

Another exemplary embodiment may be directed to a compound of formula (VII):

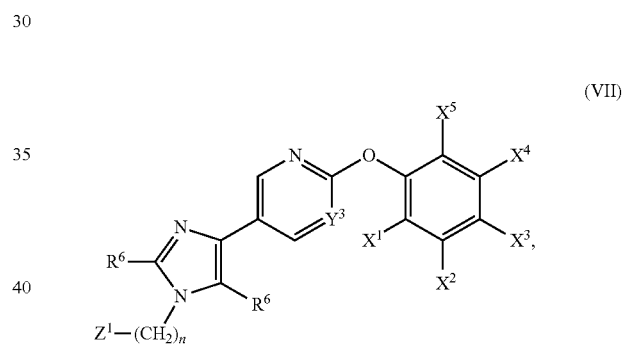

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, and $X^5$ are as defined above for a compound of Formula (VI).

Another exemplary embodiment may be directed to a compound of formula (VIII):

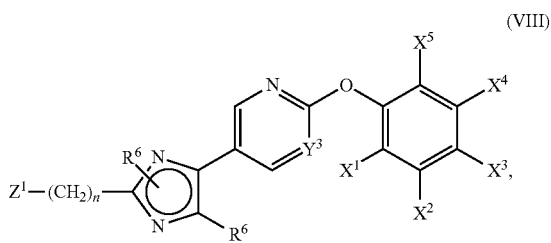

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, and $X^5$ are as defined above for a compound of Formula (VI).

Another exemplary embodiment may be directed to a compound of formula (IX):

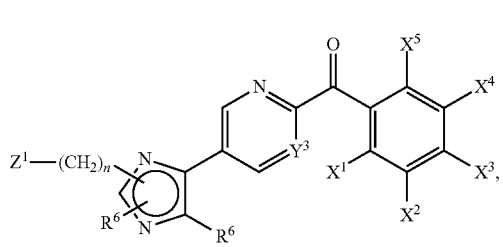

(IX)

or an equivalent thereof, or an N-oxide thereof, or a pharmaceutically acceptable salt or solvate thereof, wherein each $X^1$, $X^2$, $X^3$, $X^4$, and $X^5$ is independently hydrogen or fluoro, with no more than two of $X^1$, $X^2$, $X^3$, $X^4$, and $X^5$ being fluoro; and wherein n, $Z^1$, $R^6$, and $Y^3$ are as defined above for a compound of Formula (I).

Another exemplary embodiment may be directed to a compound of formula (X):

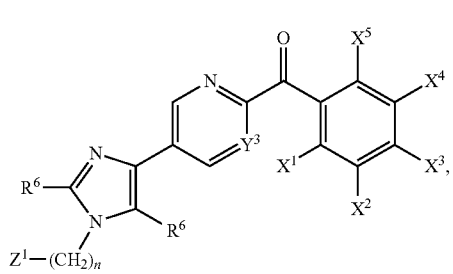

(X)

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, and $X^5$ are as defined above for a compound of Formula (IX).

Another exemplary embodiment may be directed to a compound of formula (XI):

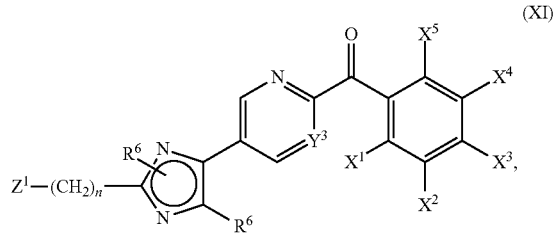

(XI)

or an equivalent thereof, or an N-oxide thereof, or a pharmaceutically acceptable salt or solvate thereof, wherein n, $Z^1$, $R^6$, $Y^3$, $X^1$, $X^2$, $X^3$, $X^4$, and $X^5$ are as defined above for a compound of Formula (IX).

Another exemplary embodiment may be directed to a compound of formula (XII):

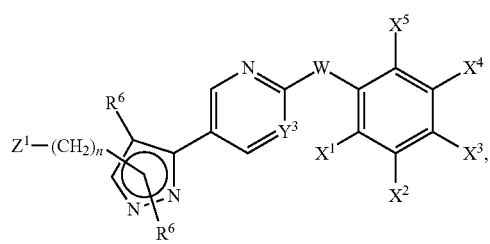

(XII)

or an equivalent thereof, or an N-oxide thereof, or a pharmaceutically acceptable salt or solvate thereof, wherein W is a covalent bond, oxygen atom (O), or carbonyl group (CO), and wherein each $X^1$, $X^2$, $X^3$, $X^4$, and $X^5$ is independently hydrogen or fluoro, with no more than two of $X^1$, $X^2$, $X^3$, $X^4$, and $X^5$ being fluoro; and wherein n, $Z^1$, $R^6$, and $Y^3$ are as defined above for a compound of Formula (I).

Another exemplary embodiment may be directed to a compound of formula (XIII):

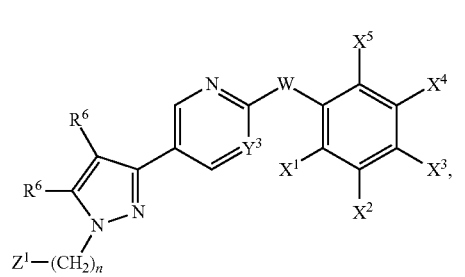

(XIII)

or an equivalent thereof, or an N-oxide thereof, or a pharmaceutically acceptable salt or solvate thereof, wherein n, $Z^1$, $R^6$, $Y^3$, W, $X^1$, $X^2$, $X^3$, $X^4$ and $X^5$ are as defined above for a compound of Formula (XII).

Another exemplary embodiment may be directed to a compound of formula (XIV):

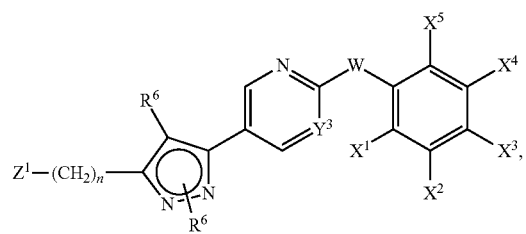

(XIV)

or an equivalent thereof, or an N-oxide thereof, or a pharmaceutically acceptable salt or solvate thereof, wherein n, $Z^1$, $R^6$, $Y^3$, W, $X^1$, $X^2$, $X^3$, $X^4$, and $X^5$ are as defined above for a compound of Formula (XII).

Another exemplary embodiment may be directed to a compound of formula (XV):

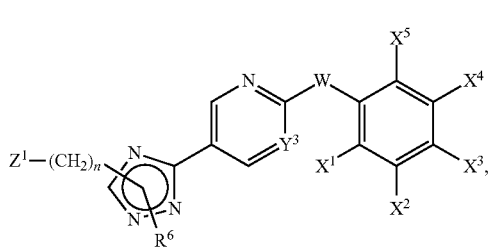

(XV)

or an equivalent thereof, or an N-oxide thereof, or a pharmaceutically acceptable salt or solvate thereof, wherein W is a covalent bond, oxygen atom (O), or carbonyl group (CO); and wherein each $X^1$, $X^2$, $X^3$, $X^4$, and $X^5$ is independently hydrogen or fluoro, with no more than two of $X^1$, $X^2$, $X^3$, $X^4$, and $X^5$ being fluoro; and wherein n, $Z^1$, $R^6$, and $Y^3$ are as defined above for a compound of Formula (I).

Another exemplary embodiment may be directed to a compound of formula (XVI):

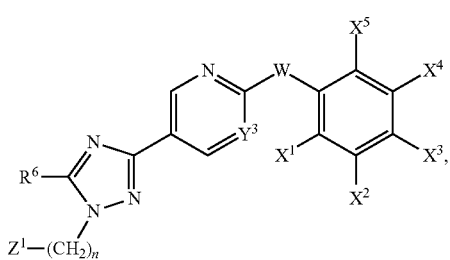

(XVI)

or an equivalent thereof, or an N-oxide thereof, or a pharmaceutically acceptable salt or solvate thereof, wherein n, $Z^1$, $R^6$, $Y^3$, W, $X^1$, $X^2$, $X^3$, $X^4$, and $X^5$ are as defined above for a compound of Formula (XV).

Another exemplary embodiment may be directed to a compound of formula (XVII):

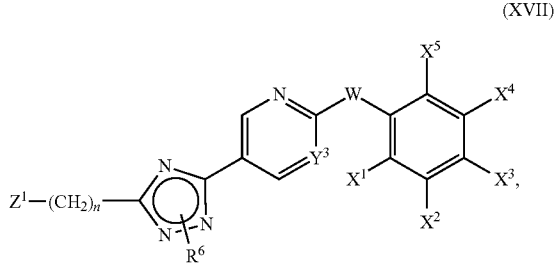

(XVII)

or an equivalent thereof, or an N-oxide thereof, or a pharmaceutically acceptable salt or solvate thereof, wherein n, $Z^1$, $R^6$, $Y^3$, W, $X^1$, $X^2$, $X^3$, $X^4$, and $X^5$ are as defined above for a compound of Formula (XV).

Another exemplary embodiment may be directed to a compound of formula (XVIII):

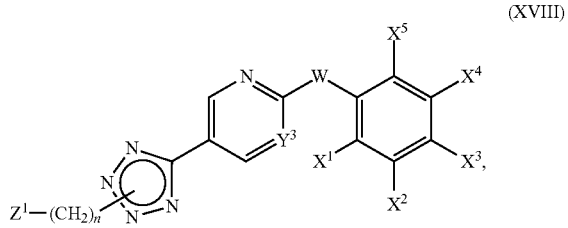

(XVIII)

or an equivalent thereof, or an N-oxide thereof, or a pharmaceutically acceptable salt or solvate thereof, wherein W is a covalent bond, oxygen atom (O), or carbonyl group (CO); and wherein each $X^1$, $X^2$, $X^3$, $X^4$, and $X^5$ is independently hydrogen or fluoro, with no more than two of $X^1$, $X^2$, $X^3$, $X^4$, and $X^5$ being fluoro; and wherein n, $Z^1$, and $Y^3$ are as defined above for a compound of Formula (I).

Another exemplary embodiment may be directed to a compound of formula (XIX):

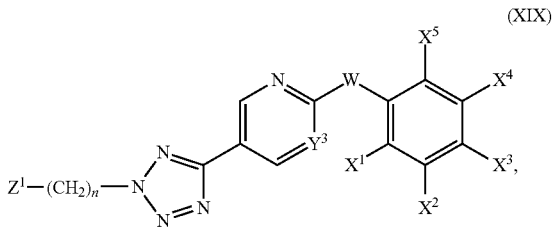

(XIX)

or an equivalent thereof, or an N-oxide thereof, or a pharmaceutically acceptable salt or solvate thereof, wherein n, $Z^1$, $Y^3$, W, $X^1$, $X^2$, $X^3$, $X^4$, and $X^5$ are as defined above for a compound of Formula (XVIII).

Another exemplary embodiment may be directed to a compound of formula (I) or (II), wherein $R^1$ is phenyl or 3-fluorophenyl; or an equivalent thereof, or an N-oxide thereof, or a pharmaceutically acceptable salt or solvate thereof.

Another exemplary embodiment may be directed to a compound of formula (I) or (II), wherein $R^1$ is phenyl; or an equivalent thereof, or an N-oxide thereof, or a pharmaceutically acceptable salt or solvate thereof.

Another exemplary embodiment may be directed to a compound of formula (I) or (II), wherein $R^1$ is 3-fluorophenyl; or an equivalent thereof, or an N-oxide thereof, or a pharmaceutically acceptable salt or solvate thereof.

Another exemplary embodiment may be directed to a compound of formula (I) or (II), wherein $R^2$ is 2-pyridyl, 3-pyridyl, or 4-pyridyl; or an equivalent thereof, or an N-oxide thereof, or a pharmaceutically acceptable salt or solvate thereof.

Another exemplary embodiment may be directed to a compound of formula (I) or (II) wherein $R^2$ is phenyl; or an equivalent thereof, or an N-oxide thereof, or a pharmaceutically acceptable salt or solvate thereof.

Another exemplary embodiment may be directed to a compound of formula (I) or (II) wherein $R^2$ is 3-fluorophenyl; or an equivalent thereof, or an N-oxide thereof, or a pharmaceutically acceptable salt or solvate thereof.

Another exemplary embodiment may be directed to a compound of formula (I) wherein $R^2$ is benzyl; or an equivalent thereof, or an N-oxide thereof, or a pharmaceutically acceptable salt or solvate thereof.

Another exemplary embodiment may be directed to a compound of formula (I) or (II) wherein $R^2$ is 2-pyridylmethyl, 3-pyridylmethyl, or 4-pyridylmethyl; or an equivalent thereof, or an N-oxide thereof, or a pharmaceutically acceptable salt or solvate thereof.

Another exemplary embodiment may be directed to a compound of formula (I) or (II), wherein $R^2$ is attached to a carbon atom of the adjacent aromatic ring and is

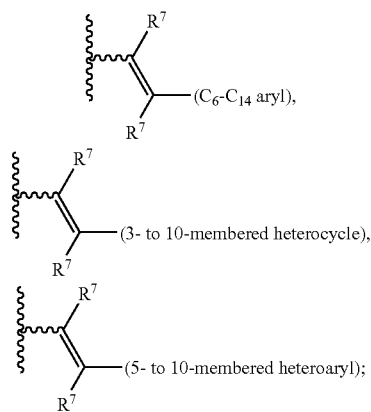

or an equivalent thereof, or an N-oxide thereof, or a pharmaceutically acceptable salt or solvate thereof.

Another exemplary embodiment may be directed to a compound of formula (I) or (II), wherein $R^2$ is attached to a carbon atom of the adjacent aromatic ring and is

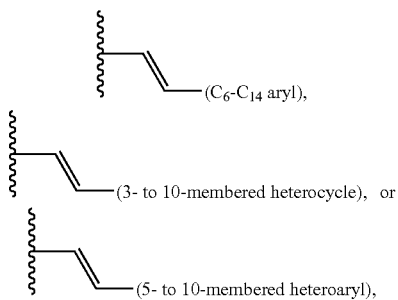

all of E-geometry; or an equivalent thereof, or an N-oxide thereof, or a pharmaceutically acceptable salt or solvate thereof.

Another exemplary embodiment may be directed to a compound of formula (I) or (II), wherein $R^2$ is attached to a carbon atom of the adjacent aromatic ring and is

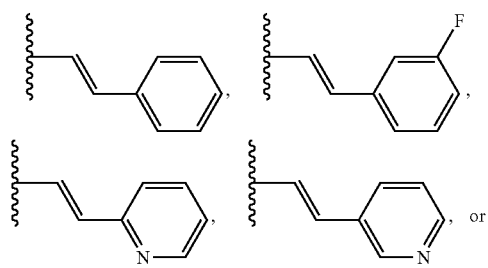

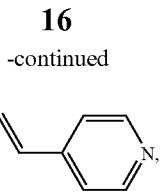

all of E-geometry, or an equivalent thereof, or an N-oxide thereof, or a pharmaceutically acceptable salt or solvate thereof.

Another exemplary embodiment may be directed to a compound of formula (I) or (II), wherein $R^2$ is attached to a carbon atom of the adjacent aromatic ring and is

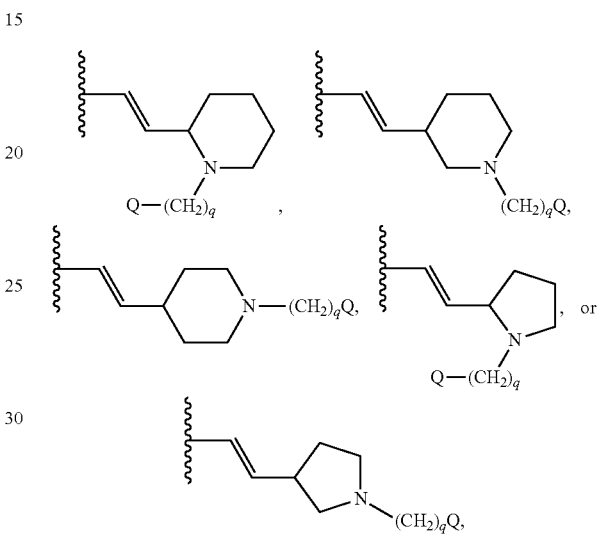

all of E-geometry; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with $-(CH_2)_q Q$; wherein q is 0, 1, 2, 3, or 4; wherein Q is hydrogen, $(C_1-C_6)$-alkyl, $CH_2CF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl; wherein $R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, or $(CH_2)_m$-(five- to ten-membered heteroaryl); wherein m is 0, 1, 2, 3, or 4; wherein $R^3$ may further be vinyl or ethyl when not covalently bonded to an N or O atom, or an S atom possessing a −2 (minus two) oxidation state; wherein each $R^4$ and $R^5$ is independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl); wherein the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide; wherein the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$CH_2Q$; wherein Q is phenyl or naphthyl; wherein the phenyl or naphthyl is optionally substituted with one-to-three of any one or combination of the following: halo, hydroxy, sulfhydryl, ($C_1$-$C_6$)-alkoxy, ($C_1$-$C_6$)-alkyl, ($C_1$-$C_6$)-alkylthio, trifluoromethyl, trifluoromethoxy, cyano, carboxy, carboxy($C_1$-$C_3$)-alkyl, carbamoyl, or sulfamoyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with benzyl; wherein the phenyl ring of the benzyl group is optionally substituted with one-to-three of any one or combination of the following: halo, hydroxy, sulfhydryl, ($C_1$-$C_6$)-alkoxy, ($C_1$-$C_6$)-alkyl, ($C_1$-$C_6$)-alkylthio, trifluoromethyl, trifluoromethoxy, cyano, carboxy, carboxy($C_1$-$C_3$)-alkyl, carbamoyl, or sulfamoyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with benzyl; wherein the phenyl ring of the benzyl group is optionally substituted with one or two of any halo, hydroxy, methoxy, methyl, trifluoromethyl, trifluoromethoxy, or cyano; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl; wherein the nitrogen atom of the piperidinyl ring is substituted with benzyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_qQ$; wherein q is 0 or 1; wherein Q is a five- to ten-membered heteroaryl ring; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_qp$; wherein q is 0 or 1; wherein Q is 2-pyridyl, 3-pyridyl, or 4-pyridyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_qQ$; wherein q is 0 or 1; wherein Q is 3-pyridazyl or 1-methyl-1H-tetrazol-5-yl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$CH_2CF_3$; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl; wherein the nitrogen atom of the piperidinyl ring is substituted with —$CH_2CF_3$; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with ($C_1$-$C_6$)-alkyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_qQ$; wherein q is 0, 1, or 2; wherein Q is ($C_3$-$C_6$)-cycloalkyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with $C(O)NHR^5$; wherein $R^5$ is ($C_1$-$C_6$)-alkyl or ($C_3$-$C_6$)-cycloalkyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with $C(O)NHR^5$; wherein $R^5$ is methyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with $CO_2R^3$; wherein $R^3$ is ($C_1$-$C_6$)-alkyl or ($C_3$-$C_6$)-cycloalkyl; or an equivalent thereof, or an N-oxide thereof, or a pharmaceutically acceptable salt or solvate thereof.

Another exemplary embodiment may be directed to a compound of formula (I) or (II), wherein $R^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with C(O)R$^3$; wherein R$^3$ is $(C_1-C_6)$-alkyl, $(CH_2)_m(C_3-C_6)$-cycloalkyl, $(CH_2)_m$phenyl, $(CH_2)_m$(five- to ten-membered heteroaryl), $(CH_2)_m$(three- to ten-membered heterocycyl); or an equivalent thereof, or an N-oxide thereof, or a pharmaceutically acceptable salt or solvate thereof.

Another exemplary embodiment may be directed to a compound of formula (I) or (II), wherein R$^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_q$Q; wherein q is 1, 2, 3, or 4; wherein Q is cyano, trifluoromethyl, or $SO_2NR^4R^5$; wherein each R$^4$ and R$^5$ is independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl); wherein m is 0, 1, 2, 3, or 4; wherein the NR$^4$R$^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide; wherein the NR$^4$R$^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl; or an equivalent thereof, or an N-oxide thereof, or a pharmaceutically acceptable salt or solvate thereof.

Another exemplary embodiment may be directed to a compound of formula (I) or (II), wherein R$^2$ is 4-piperidinyl, 3-piperidinyl, (3R)-piperidinyl, (3S)-piperidinyl, 3-pyrrolidinyl, (3R)-pyrrolidinyl, (3S)-pyrrolidinyl, or 3-azetidinyl; wherein the nitrogen atom of the piperidinyl, pyrrolidinyl, or azetidinyl ring is substituted with —$(CH_2)_q$Q; wherein q is 2, 3, or 4; wherein Q is hydroxy, sulfhydryl, or NR$^4$R$^5$; wherein each R$^4$ and R$^5$ is independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl); wherein m is 0, 1, 2, 3, or 4; wherein the NR$^4$R$^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide; wherein the NR$^4$R$^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl; or an equivalent thereof, or an N-oxide thereof, or a pharmaceutically acceptable salt or solvate thereof.

Another exemplary embodiment may be directed to a compound of formula (I) or (II) wherein W is a covalent bond; or an equivalent thereof, or an N-oxide thereof, or a pharmaceutically acceptable salt or solvate thereof.

Another exemplary embodiment may be directed to a compound of formula (I) or (II) wherein W is O, S, SO, $SO_2$, $CH_2$, CHOH, CO, or NH; or an equivalent thereof, or an N-oxide thereof, or a pharmaceutically acceptable salt or solvate thereof.

Another exemplary embodiment may be directed to a compound of formula (I) or (II) wherein W is O, S, SO, or $SO_2$; or an equivalent thereof, or an N-oxide thereof, or a pharmaceutically acceptable salt or solvate thereof.

Another exemplary embodiment may be directed to a compound of formula (I) or (II) wherein W is O or S; or an equivalent thereof, or an N-oxide thereof, or a pharmaceutically acceptable salt or solvate thereof.

Another exemplary embodiment may be directed to a compound of formula (I) or (II) wherein W is O; or an equivalent thereof, or an N-oxide thereof, or a pharmaceutically acceptable salt or solvate thereof.

Another exemplary embodiment may be directed to a compound of formula (I) or (II) wherein W is CHOH or CO; or an equivalent thereof, or an N-oxide thereof, or a pharmaceutically acceptable salt or solvate thereof.

Another exemplary embodiment may be directed to a compound of formula (I) or (II) wherein W is CO; or an equivalent thereof, or an N-oxide thereof, or a pharmaceutically acceptable salt or solvate thereof.

Another exemplary embodiment may be directed to a compound of formula (I) wherein: U$^1$ is N; wherein U$^2$ is C—R$^2$; wherein U$^3$ is N—R$^6$ or S; wherein U$^4$ is C—R$^6$; wherein each R$^6$ is independently hydrogen or methyl; and wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is C—R$^2$; wherein U$^3$ is N—H; wherein U$^4$ is C—R$^6$, wherein R$^6$ is hydrogen or methyl; and wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is C—R$^2$; wherein U$^3$ is N—H; wherein U$^4$ is C—H; wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is C—R$^2$; wherein U$^3$ is N—H; wherein U$^4$ is C—CH$_3$; wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is N—R$^6$; wherein U$^3$ is C—R$^2$; wherein U$^4$ is C—R$^6$, wherein each R$^6$ is independently hydrogen or methyl; and wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is N—H; wherein U$^3$ is C—R$^2$; wherein U$^4$ is C—R$^6$, wherein R$^6$ is hydrogen or methyl; and wherein R$^2$ is as defined above for a compound of Formula (I);or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is N—H; wherein U$^3$ is C—R$^2$; wherein U$^4$ is C—H; wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein U$^1$ is N; wherein U$^2$ is N—H; wherein U$^3$ is C—R$^2$; wherein U$^4$ is C—CH$_3$; wherein R$^2$ is as defined above for a compound of Formula (I); or an equivalent thereof, or an N-oxide thereof, or a pharmaceutically acceptable salt or solvate thereof.

Another exemplary embodiment may be directed to a compound of formula (I) wherein each of $Y^1$, $Y^2$, and $Y^3$ is C—H; or an equivalent thereof, or an N-oxide thereof, or a pharmaceutically acceptable salt or solvate thereof.

Another exemplary embodiment may be directed to a compound of formula (I) wherein each of $Y^1$ and $Y^2$ is C—H and $Y^3$ is N; or an equivalent thereof, or an N-oxide thereof, or a pharmaceutically acceptable salt or solvate thereof.

Another exemplary embodiment may be a compound selected from the group consisting of: 2-phenyl-5-(2-phenyl-1H-imidazol-4-yl)pyrimidine; 5-(2-(2-fluorophenyl)-1H-imidazol-4-yl)-2-phenylpyrimidine; 5-(2-(3-fluorophenyl)-1H-imidazol-4-yl)-2-phenylpyrimidine; 5-(2-(4-fluorophenyl)-1H-imidazol-4-yl)-2-phenylpyrimidine; 2-phenyl-5-(2-(pyridin-2-yl)-1H-imidazol-4-yl)pyrimidine; 2-phenyl-5-(2-(pyridin-3-yl)-1H-imidazol-4-yl)pyrimidine; 2-phenyl-5-(2-(pyridin-4-yl)-1H-imidazol-4-yl)pyrimidine; 5-(2-benzyl-1H-imidazol-4-yl)-2-phenylpyrimidine; 5-(2-(2-fluorobenzyl)-1H-imidazol-4-yl)-2-phenylpyrimidine; 5-(2-(3-fluorobenzyl)-1H-imidazol-4-yl)-2-phenylpyrimidine; 5-(2-(4-fluorobenzyl)-1H-imidazol-4-yl)-2-phenylpyrimidine; 2-phenyl-5-(2-(pyridin-2-ylmethyl)-1H-imidazol-4-yl)pyrimidine; 2-phenyl-5-(2-(pyridin-3-ylmethyl)-1H-imidazol-4-yl)pyrimidine; 2-phenyl-5-(2-(pyridin-4-ylmethyl)-1H-imidazol-4-yl)pyrimidine; 5-(5-methyl-2-phenyl-1H-imidazol-4-yl)-2-phenylpyrimidine; 5-(1-methyl-2-phenyl-1H-imidazol-5-yl)-2-phenylpyrimidine; 5-(1-methyl-2-phenyl-1H-imidazol-4-yl)-2-phenylpyrimidine; 5-(5-methyl-2-(pyridin-3-yl)-1H-imidazol-4-yl)-2-phenylpyrimidine; 5-(1-methyl-2-(pyridin-3-yl)-1H-imidazol-5-yl)-2-phenylpyrimidine; and 5-(1-methyl-2-(pyridin-3-yl)-1H-imidazol-4-yl)-2-phenylpyrimidine; or an equivalent thereof, or an N-oxide thereof, or a pharmaceutically acceptable salt or solvate thereof.

Another exemplary embodiment may be a compound selected from the group consisting of: 2-phenyl-5-(2-(1-(2,2,2-trifluoroethyl)piperidin-4-yl)-1H-imidazol-4-yl)pyrimidine; 5-(2-(1-benzylpiperidin-4-yl)-1H-imidazol-4-yl)-2-phenylpyrimidine; 5-(2-(1-benzylpiperidin-4-yl)-5-methyl-1H-imidazol-4-yl)-2-phenylpyrimidine; 5-(2-(1-benzylpiperidin-4-yl)-1-methyl-1H-imidazol-4-yl)-2-phenylpyrimidine; 5-(2-(1-benzylpiperidin-4-yl)-1-methyl-1H-imidazol-5-yl)-2-phenylpyrimidine; 5-(2-(1-(cyclopropylmethyl)piperidin-4-yl)-1H-imidazol-4-yl)-2-phenylpyrimidine; 3-(4-(4-(2-phenylpyrimidin-5-yl)-1H-imidazol-2-yl)piperidin-1-yl)pyridazine; 5-(2-(1-(1-methyl-1H-tetrazol-5-yl)piperidin-4-yl)-1H-imidazol-4-yl)-2-phenylpyrimidine; N-methyl-4-(4-(2-phenylpyrimidin-5-yl)-1H-imidazol-2-yl)piperidine-1-carboxamide; ethyl 4-(4-(2-phenylpyrimidin-5-yl)-1H-imidazol-2-yl)piperidine-1-carboxylate; tert-butyl 4-(4-(2-phenylpyrimidin-5-yl)-1H-imidazol-2-yl)piperidine-1-carboxylate; 1-(4-(4-(2-phenylpyrimidin-5-yl)-1H-imidazol-2-yl)piperidin-1-yl)butan-1-one; 2-phenyl-5-(2-((1-(2,2,2-trifluoroethyl)piperidin-4-yl)methyl)-1H-imidazol-4-yl)pyrimidine; 2-phenyl-5-(2-(1-(2,2,2-trifluoroethyl)piperidin-3-yl)-1H-imidazol-4-yl)pyrimidine; (R)-2-phenyl-5-(2-(1-(2,2,2-trifluoroethyl)piperidin-3-yl)-1H-imidazol-4-yl)pyrimidine; (S)-2-phenyl-5-(2-(1-(2,2,2-trifluoroethyl)piperidin-3-yl)-1H-imidazol-4-yl)pyrimidine; 5-(5-methyl-2-(1-(2,2,2-trifluoroethyl)piperidin-3-yl)-1H-imidazol-4-yl)-2-phenylpyrimidine; (R)-5-(5-methyl-2-(1-(2,2,2-trifluoroethyl)piperidin-3-yl)-1H-imidazol-4-yl)-2-phenylpyrimidine; (R)-5-(5-methyl-2-(1-(2,2,2-trifluoroethyl)piperidin-3-yl)-1H-imidazol-4-yl)-2-phenylpyrimidine; 5-(2-(1-benzylpiperidin-3-yl)-1H-imidazol-4-yl)-2-phenylpyrimidine; (R)-5-(2-(1-benzylpiperidin-3-yl)-1H-imidazol-4-yl)-2-phenylpyrimidine; (S)-5-(2-(1-benzylpiperidin-3-yl)-1H-imidazol-4-yl)-2-phenylpyrimidine; N-methyl-3-(4-(2-phenylpyrimidin-5-yl)-1H-imidazol-2-yl)piperidine-1-carboxamide; (R)-N-methyl-3-(4-(2-phenylpyrimidin-5-yl)-1H-imidazol-2-yl)pipendine-1-carboxamide; (S)-N-methyl-3-(4-(2-phenylpyrimidin-5-yl)-1H-imidazol-2-yl)piperidine-1-carboxamide; N-cyclopropyl-3-(4-(2-phenylpyrimidin-5-yl)-1H-imidazol-2-yl)piperidine-1-carboxamide; (R)-N-cyclopropyl-3-(4-(2-phenylpyrimidin-5-yl)-1H-imidazol-2-yl)piperidine-1-carboxamide; (S)-N-cyclopropyl-3-(4-(2-phenylpyrimidin-5-yl)-1H-imidazol-2-yl)piperidine-1-carboxamide; cyclopropyl(3-(4-(2-phenylpyrimidin-5-yl)-1H-imidazol-2-yl)piperidin-1-yl)methanone; (R)-cyclopropyl(3-(4-(2-phenylpyrimidin-5-yl)-1H-imidazol-2-yl)piperidin-1-yl)methanone; (S)-cyclopropyl(3-(4-(2-phenylpyrimidin-5-yl)-1H-imidazol-2-yl)piperidin-1-yl)methanone; 5-(2-(1-(cyclopropylmethyl)piperidin-3-yl)-1H-imidazol-4-yl)-2-phenylpyrimidine; (R)-5-(2-(1-(cyclopropylmethyl)piperidin-3-yl)-1H-imidazol-4-yl)-2-phenylpyrimidine; (S)-5-(2-(1-(cyclopropylmethyl)piperidin-3-yl)-1H-imidazol-4-yl)-2-phenylpyrimidine; 2-phenyl-5-(2-(1-(2,2,2-trifluoroethyl)piperidin-2-yl)-1H-imidazol-4-yl)pyrimidine; (S)-2-phenyl-5-(2-(1-(2,2,2-trifluoroethyl)piperidin-2-yl)-1H-imidazol-4-yl)pyrimidine; and (R)-2-phenyl-5-(2-(1-(2,2,2-trifluoroethyl)piperidin-2-yl)-1H-imidazol-4-yl)pyrimidine; or an equivalent thereof, or an N-oxide thereof, or a pharmaceutically acceptable salt or solvate thereof.

Another exemplary embodiment may be a compound selected from the group consisting of: 2-phenyl-5-(2-(1-(2,2,2-trifluoroethyl)pyrrolidin-3-yl)-1H-imidazol-4-yl)pyrimidine; (R)-2-phenyl-5-(2-(1-(2,2,2-trifluoroethyl)pyrrolidin-3-yl)-1H-imidazol-4-yl)pyrimidine; (S)-2-phenyl-5-(2-(1-(2,2,2-trifluoroethyl)pyrrolidin-3-yl)-1H-imidazol-4-yl)pyrimidine; 5-(2-(1-benzylpyrrolidin-3-yl)-1H-imidazol-4-yl)-2-phenylpyrimidine; (R)-5-(2-(1-benzylpyrrolidin-3-yl)-1H-imidazol-4-yl)-2-phenylpyrimidine; (S)-5-(2-(1-benzylpyrrolidin-3-yl)-1H-imidazol-4-yl)-2-phenylpyrimidine; ethyl 3-(4-(2-phenylpyrimidin-5-yl)-1H-imidazol-2-yl)pyrrolidine-1-carboxylate; (R)-ethyl 3-(4-(2-phenylpyrimidin-5-yl)-1H-imidazol-2-yl)pyrrolidine-1-carboxylate; (S)-ethyl 3-(4-(2-phenylpyrimidin-5-yl)-1H-imidazol-2-yl)pyrrolidine-1-carboxylate; tert-butyl 3-(4-(2-phenylpyrimidin-5-yl)-1H-imidazol-2-yl)pyrrolidine-1-carboxylate; (R)-tert-butyl 3-(4-(2-phenylpyrimidin-5-yl)-1H-imidazol-2-yl)pyrrolidine-1-carboxylate; (S)-tert-butyl 3-(4-(2-phenylpyrimidin-5-yl)-1H-imidazol-2-yl)pyrrolidine-1-carboxylate; N-methyl-3-(4-(2-phenylpyrimidin-5-yl)-1H-imidazol-2-yl)pyrrolidine-1-carboxamide; (R)-N-methyl-3-(4-(2-phenylpyrimidin-5-yl)-1H-imidazol-2-yl)pyrrolidine-1-carboxamide; (S)-N-methyl-3-(4-(2-phenylpyrimidin-5-yl)-1H-imidazol-2-yl)pyrrolidine-1-carboxamide; 2-phenyl-5-(2-(1-(2,2,2-trifluoroethyl)pyrrolidin-2-yl)-1H-imidazol-4-yl)pyrimidine; (S)-2-phenyl-5-(2-(1-(2,2,2-trifluoroethyl)pyrrolidin-2-yl)-1H-imidazol-4-yl)pyrimidine; (R)-2-phenyl-5-(2-(1-(2,2,2-trifluoroethyl)pyrrolidin-2-yl)-1H-imidazol-4-yl)pyrimidine; 2-phenyl-5-(2-(1-(2,2,2-trifluoroethyl)azetidin-3-yl)-1H-imidazol-4-yl)pyrimidine; 5-(2-(1-benzylazetidin-3-yl)-1H-imidazol-4-yl)-2-phenylpyrimidine; 1-(3-(4-(2-phenylpyrimidin-5-yl)-1H-imidazol-2-yl)azetidin-1-yl)butan-1-one; 5-(5-methyl-2-(1-(2,2,2-trifluoroethyl)pyrrolidin-3-yl)-1H-imidazol-4-yl)-2-phenylpyrimidine; (R)-5-(5-methyl-2-(1-(2,2,2-trifluoroethyl)pyrrolidin-3-yl)-

1H-imidazol-4-yl)-2-phenylpyrimidine; (S)-5-(5-methyl-2-(1-(2,2,2-trifluoroethyl)pyrrolidin-3-yl)-1H-imidazol-4-yl)-2-phenylpyrimidine; 5-(2-(1-benzylpyrrolidin-3-yl)-5-methyl-1H-imidazol-4-yl)-2-phenylpyrimidine; (R)-5-(2-(1-benzylpyrrolidin-3-yl)-5-methyl-1H-imidazol-4-yl)-2-phenylpyrimidine; and (S)-5-(2-(1-benzylpyrrolidin-3-yl)-5-methyl-1H-imidazol-4-yl)-2-phenylpyrimidine; or an equivalent thereof, or an N-oxide thereof, or a pharmaceutically acceptable salt or solvate thereof.

Another exemplary embodiment may be a compound selected from the group consisting of: (E)-2-phenyl-5-(2-styryl-1H-imidazol-4-yl)pyrimidine; (E)-5-(2-(2-fluorostyryl)-1H-imidazol-4-yl)-2-phenylpyrimidine; (E)-5-(2-(3-fluorostyryl)-1H-imidazol-4-yl)-2-phenylpyrimidine; (E)-5-(2-(4-fluorostyryl)-1H-imidazol-4-yl)-2-phenylpyrimidine; (E)-2-phenyl-5-(2-(2-(pyridin-2-yl)vinyl)-1H-imidazol-4-yl)pyrimidine; (E)-2-phenyl-5-(2-(2-(pyridin-3-yl)vinyl)-1H-imidazol-4-yl)pyrimidine; (E)-2-phenyl-5-(2-(2-(pyridin-4-yl)vinyl)-1H-imidazol-4-yl)pyrimidine; (E)-2-(3-fluorophenyl)-5-(5-methyl-2-(2-(pyridin-3-yl)vinyl)-1H-imidazol-4-yl)pyrimidine; and (E)-2-(3-fluorophenyl)-5-(1-methyl-2-(2-(pyridin-3-yl)vinyl)-1H-imidazol-4-yl)pyrimidine; or an equivalent thereof, or an N-oxide thereof, or a pharmaceutically acceptable salt or solvate thereof.

Another exemplary embodiment may be a compound selected from the group consisting of: 5-(2-phenethyl-1H-imidazol-4-yl)-2-phenylpyrimidine; 5-(2-(2-fluorophenethyl)-1H-imidazol-4-yl)-2-phenylpyrimidine; 5-(2-(3-fluorophenethyl)-1H-imidazol-4-yl)-2-phenylpyrimidine; 5-(2-(4-fluorophenethyl)-1H-imidazol-4-yl)-2-phenylpyrimidine; 2-phenyl-5-(2-(2-(pyridin-2-yl)ethyl)-1H-imidazol-4-yl)pyrimidine; 2-phenyl-5-(2-(2-(pyridin-3-yl)ethyl)-1H-imidazol-4-yl)pyrimidine; 2-phenyl-5-(2-(2-(pyridin-4-yl)ethyl)-1H-imidazol-4-yl)pyrimidine; 2-(3-fluorophenyl)-5-(5-methyl-2-(2-(pyridin-3-yl)ethyl)-1H-imidazol-4-yl)pyridine; and 5-(1-methyl-2-(2-(pyridin-3-yl)ethyl)-1H-imidazol-4-yl)-2-phenylpyrimidine; or an equivalent thereof, or an N-oxide thereof, or a pharmaceutically acceptable salt or solvate thereof.

Another exemplary embodiment may be a compound selected from the group consisting of (E)-5-(2-(2-(1-benzylpiperidin-4-yl)vinyl)1H-imidazol-4-yl)-2-phenylpyrimidine; (E)-2-phenyl-5-(2-(2-(1-(2,2,2-trifluoroethyl)piperidin-3-yl)vinyl)-1H-imidazol-4-yl)pyrimidine; (S,E)-2-phenyl-5-(2-(2-(1-(2,2,2-trifluoroethyl)piperidin-3-yl)vinyl)-1H-imidazol-4-yl)pyrimidine; (R,E)-2-phenyl-5-(2-(2-(1-(2,2,2-trifluoroethyl)piperidin-3-yl)vinyl)-1H-imidazol-4-yl)pyrimidine; (E)-2-phenyl-5-(2-(2-(1-propylpiperidin-2-yl)vinyl)-1H-imidazol-4-yl)pyrimidine; (S,E)-2-phenyl-5-(2-(2-(1-propylpipendin-2-yl)vinyl)-1H-imidazol-4-yl)pyrimidine; (R,E)-2-phenyl-5-(2-(2-(1-propylpiperidin-2-yl)vinyl)-1H-imidazol-4-yl)pyrimidine; (E)-3-(2-(4-(2-(3-fluorophenyl)pyrimidin-5-yl)-5-methyl-1H-imidazol-2-yl)vinyl)-N-methylpyrrolidine-1-carboxamide; and (E)-5-(2-(2-(1-(cyclopropylmethyl)pyrrolidin-2-yl)vinyl)-1-methyl-1H-imidazol-4-yl)-2-(3-fluorophenyl)pyridine; or an equivalent thereof, or an N-oxide thereof, or a pharmaceutically acceptable salt or solvate thereof.

Another exemplary embodiment may be a compound selected from the group consisting of: 5-(2-(2-(1-benzylpiperidin-4-yl)ethyl)-1H-imidazol-4-yl)-2-phenylpyrimidine; 2-phenyl-5-(2-(2-(1-(2,2,2-trifluoroethyl)piperidin-3-yl)ethyl)-1H-imidazol-4-yl)pyrimidine; (S)-2-phenyl-5-(2-(2-(1-(2,2,2-trifluoroethyl)piperidin-3-yl)ethyl)-1H-imidazol-4-yl)pyrimidine; (R)-2-phenyl-5-(2-(2-(1-(2,2,2-trifluoroethyl)piperidin-3-yl)ethyl)-1H-imidazol-4-yl)pyrimidine; 5-(2-(2-(1-isobutylpiperidin-2-yl)ethyl)-1H-imidazol-4-yl)-2-phenylpyrimidine; (S)-5-(2-(2-(1-isobutylpiperidin-2-yl)ethyl)-1H-imidazol-4-yl)-2-phenylpyrimidine; (R)-5-(2-(2-(1-isobutylpiperidin-2-yl)ethyl)-1H-imidazol-4-yl)-2-phenylpyrimidine; ethyl 3-(2-(4-(2-(3-fluorophenyl)pyrimidin-5-yl)-5-methyl-1H-imidazol-2-yl)ethyl)pyrrolidine-1-carboxylate; and 1-(2-(2-(4-(6-(3-fluorophenyl)pyridin-3-yl)-1-methyl-1H-imidazol-2-yl)ethyl)pyrrolidin-1-yl)butan-1-one; or an equivalent thereof, or an N-oxide thereof, or a pharmaceutically acceptable salt or solvate thereof.

Another exemplary embodiment may be a compound selected from the group consisting of: 2-phenyl-5-(2-phenyl-1H-imidazol-4-yl)pyridine; 5-(2-(2-fluorophenyl)-1H-imidazol-4-yl)-2-phenylpyridine; 5-(2-(3-fluorophenyl)-1H-imidazol-4-yl)-2-phenylpyridine; 5-(2-(4-fluorophenyl)-1H-imidazol-4-yl)-2-phenylpyridine; 2-phenyl-5-(2-(pyridin-2-yl)-1H-imidazol-4-yl)pyridine; 2-phenyl-5-(2-(pyridin-3-yl)-1H-imidazol-4-yl)pyridine; 2-phenyl-5-(2-(pyridin-4-yl)-1H-imidazol-4-yl)pyridine; 5-(2-benzyl-1H-imidazol-4-yl)-2-phenylpyridin; 5-(2-(2-fluorobenzyl)-1H-imidazol-4-yl)-2-phenylpyridine; 5-(2-(3-fluorobenzyl)-1H-imidazol-4-yl)-2-phenylpyridine; 5-(2-(4-fluorobenzyl)-1H-imidazol-4-yl)-2-phenylpyridine; 2-phenyl-5-(2-(pyridin-2-ylmethyl)-1H-imidazol-4-yl)pyridine; 2-phenyl-5-(2-(pyridin-3-ylmethyl)-1H-imidazol-4-yl)pyridine; 2-phenyl-5-(2-(pyridin-4-ylmethyl)-1H-imidazol-4-yl)pyridine; 5-(5-methyl-2-phenyl-1H-imidazol-4-yl)-2-phenylpyridine; 5-(1-methyl-2-phenyl-1H-imidazol-5-yl)-2-phenylpyridine; 5-(1-methyl-2-phenyl-1H-imidazol-4-yl)-2-phenylpyridine; 5-(5-methyl-2-(pyridin-3-yl)-1H-imidazol-4-yl)-2-phenylpyridine; 5-(1-methyl-2-(pyridin-3-yl)-1H-imidazol-5-yl)-2-phenylpyridine; and 5-(1-methyl-2-(pyridin-3-yl)-1H-imidazol-4-yl)-2-phenylpyridine; or an equivalent thereof, or an N-oxide thereof, or a pharmaceutically acceptable salt or solvate thereof.

Another exemplary embodiment may be a compound selected from the group consisting of: 2-phenyl-5-(2-(1-(2,2,2-trifluoroethyl)piperidin-4-yl)-1H-imidazol-4-yl)pyridine; 5-(5-methyl-2-(1-(2,2,2-trifluoroethyl)piperidin-4-yl)-1H-imidazol-4-yl)-2-phenylpyridine; 5-(2-(1-benzylpiperidin-4-yl)-1H-imidazol-4-yl)-2-phenylpyridine; 5-(2-(1-benzylpiperidin-4-yl)-5-methyl-1H-imidazol-4-yl)-2-phenylpyridine; 5-(2-(1-benzylpiperidin-4-yl)-1-methyl-1H-imidazol-4-yl)-2-phenylpyridine; 5-(2-(1-benzylpiperidin-4-yl)-1-methyl-1H-imidazol-5-yl)-2-phenylpyridine; 5-(2-(1-(cyclopropylmethyl)piperidin-4-yl)-1H-imidazol-4-yl)-2-phenylpyridine; 3-(4-(4-(6-phenylpyridin-3-yl)-1H-imidazol-2-yl)piperidin-1-yl)pyridazine; 5-(2-(1-(1-methyl-1H-tetrazol-5-yl)piperidin-4-yl)-1H-imidazol-4-yl)-2-phenylpyridine; N-methyl-4-(4-(6-phenylpyridin-3-yl)-1H-imidazol-2-yl)piperidine-1-carboxamide; ethyl 4-(4-(6-phenylpyridin-3-yl)-1H-imidazol-2-yl)piperidine-1-carboxylate; 1-(4-(4-(6-phenylpyridin-3-yl)-1H-imidazol-2-yl)piperidin-1-yl)butan-1-one; 2-phenyl-5-(2-((1-(2,2,2-trifluoroethyl)piperidin-4-yl)methyl)-1H-imidazol-4-yl)pyridine; 2-phenyl-5-(2-(1-(2,2,2-trifluoroethyl)piperidin-3-yl)-1H-imidazol-4-yl)pyridine; 5-(5-methyl-2-(1-(2,2,2-trifluoroethyl)piperidin-3-yl)-1H-imidazol-4-yl)-2-phenylpyridine; (R)-5-(5-methyl-2-(1-(2,2,2-trifluoroethyl)piperidin-3-yl)-1H-imidazol-4-yl)-2-phenylpyridine; (S)-5-(5-methyl-2-(1-(2,2,2-trifluoroethyl)piperidin-3-yl)-1H-imidazol-4-yl)-2-phenylpyridine; (R)-2-phenyl-5-(2-(1-(2,2,2-trifluoroethyl)piperidin-3-yl)-1H-imidazol-4-yl)pyridine; (S)-2-phenyl-5-(2-(1-(2,2,2-trifluoroethyl)piperidin-3-yl)-1H-imidazol-4-yl)pyridine; 5-(2-(1-benzylpiperidin-3-yl)-1H-imidazol-4-yl)-2-phenylpyridine; (R)-5-(2-(1-benzylpiperidin-3-yl)-1H-imidazol-4-yl)-2-phenylpyridine; (S)-5-(2-

(1-benzylpiperidin-3-yl)-1H-imidazol-4-yl)-2-phenylpyridine; N-cyclopropyl-3-(4-(6-phenylpyridin-3-yl)-1H-imidazol-2-yl)piperidine-1-carboxamide; (R)-N-cyclopropyl-3-(4-(6-phenylpyridin-3-yl)-1H-imidazol-2-yl) piperidine-1-carboxamide; (S)-N-cyclopropyl-3-(4-(6-phenylpyridin-3-yl)-1H-imidazol-2-yl)piperidine-1-carboxamide; 2-phenyl-5-(2-(1-(2,2,2-trifluoroethyl)piperidin-2-yl)-1H-imidazol-4-yl)pyridine; (S)-2-phenyl-5-(2-(1-(2,2,2-trifluoroethyl)piperidin-2-yl)-1H-imidazol-4-yl)pyridine; and (R)-2-phenyl-5-(2-(1-(2,2,2-trifluoroethyl)piperidin-2-yl)-1H-imidazol-4-yl)pyridine; or an equivalent thereof, or an N-oxide thereof, or a pharmaceutically acceptable salt or solvate thereof.

Another exemplary embodiment may be a compound selected from the group consisting of: 2-phenyl-5-(2-(1-(2,2,2-trifluoroethyl)pyrrolidin-3-yl)-1H-imidazol-4-yl)pyridine; (R)-2-phenyl-5-(2-(1-(2,2,2-trifluoroethyl)pyrrolidin-3-yl)-1H-imidazol-4-yl)pyridine; (S)-2-phenyl-5-(2-(1-(2,2,2-trifluoroethyl)pyrrolidin-3-yl)-1H-imidazol-4-yl)pyridine; 5-(5-methyl-2-(1-(2,2,2-trifluoroethyl)pyrrolidin-3-yl)-1H-imidazol-4-yl)-2-phenylpyridine; (R)-5-(5-methyl-2-(1-(2,2,2-trifluoroethyl)pyrrolidin-3-yl)-1H-imidazol-4-yl)-2-phenylpyridine; (S)-5-(5-methyl-2-(1-(2,2,2-trifluoroethyl)pyrrolidin-3-yl)-1H-imidazol-4-yl)-2-phenylpyridine; 5-(2-(1-benzylpyrrolidin-3-yl)-5-methyl-1H-imidazol-4-yl)-2-phenylpyridine; 5-(2-(1-benzylpyrrolidin-3-yl)-1-methyl-1H-imidazol-4-yl)-2-phenylpyridine; 5-(2-(1-benzylpyrrolidin-3-yl)-1-methyl-1H-imidazol-5-yl)-2-phenylpyridine; (R)-5-(2-(1-benzylpyrrolidin-3-yl)-5-methyl-1H-imidazol-4-yl)-2-phenylpyridine; (R)-5-(2-(1-benzylpyrrolidin-3-yl)-1-methyl-1H-imidazol-4-yl)-2-phenylpyridine; (R)-5-(2-(1-benzylpyrrolidin-3-yl)-1-methyl-1H-imidazol-5-yl)-2-phenylpyridine; (S)-5-(2-(1-benzylpyrrolidin-3-yl)-5-methyl-1H-imidazol-4-yl)-2-phenylpyridine; (S)-5-(2-(1-benzylpyrrolidin-3-yl)-1-methyl-1H-imidazol-4-yl)-2-phenylpyridine; (S)-5-(2-(1-benzylpyrrolidin-3-yl)-1-methyl-1H-imidazol-5-yl)-2-phenylpyridine; ethyl 3-(4-(6-phenylpyridin-3-yl)-1H-imidazol-2-yl)pyrrolidine-1-carboxylate; (R)-ethyl 3-(4-(6-phenylpyridin-3-yl)-1H-imidazol-2-yl)pyrrolidine-1-carboxylate; (S)-ethyl 3-(4-(6-phenylpyridin-3-yl)-1H-imidazol-2-yl)pyrrolidine-1-carboxylate; N-methyl-3-(4-(6-phenylpyridin-3-yl)-1H-imidazol-2-yl)pyrrolidine-1-carboxamide; (R)-N-methyl-3-(4-(6-phenylpyridin-3-yl)-1H-imidazol-2-yl)pyrrolidine-1-carboxamide; (S)-N-methyl-3-(4-(6-phenylpyridin-3-yl)-1H-imidazol-2-yl)pyrrolidine-1-carboxamide; 2-phenyl-5-(2-(1-(2,2,2-trifluoroethyl)pyrrolidin-2-yl)-1H-imidazol-4-yl)pyridine; (S)-2-phenyl-5-(2-(1-(2,2,2-trifluoroethyl)pyrrolidin-2-yl)-1H-imidazol-4-yl)pyridine; (R)-2-phenyl-5-(2-(1-(2,2,2-trifluoroethyl)pyrrolidin-2-yl)-1H-imidazol-4-yl)pyridine; 2-phenyl-5-(2-(1-(2,2,2-trifluoroethyl)azetidin-3-yl)-1H-imidazol-4-yl)pyridine; 5-(2-(1-benzylazetidin-3-yl)-1H-imidazol-4-yl)-2-phenylpyridine; and 1-(3-(4-(6-phenylpyridin-3-yl)-1H-imidazol-2-yl)azetidin-1-yl)butan-1-one; or an equivalent thereof, or an N-oxide thereof, or a pharmaceutically acceptable salt or solvate thereof.

Another exemplary embodiment may be a compound selected from the group consisting of: 2-(3-fluorophenyl)-5-(2-phenyl-1H-imidazol-4-yl)pyrimidine; 2-(3-fluorophenyl)-5-(2-(2-fluorophenyl)-1H-imidazol-4-yl)pyrimidine; 2-(3-fluorophenyl)-5-(2-(3-fluorophenyl)-1H-imidazol-4-yl)pyrimidine; 2-(3-fluorophenyl)-5-(2-(4-fluorophenyl)-1H-imidazol-4-yl)pyrimidine; 2-(3-fluorophenyl)-5-(2-(pyridin-2-yl)-1H-imidazol-4-yl)pyrimidine; 2-(3-fluorophenyl)-5-(2-(pyridin-3-yl)-1H-imidazol-4-yl)pyrimidine; 2-(3-fluorophenyl)-5-(2-(pyridin-4-yl)-1H-imidazol-4-yl)pyrimidine; 5-(2-benzyl-1H-imidazol-4-yl)-2-(3-fluorophenyl)pyrimidine; 5-(2-(2-fluorobenzyl)-1H-imidazol-4-yl)-2-(3-fluorophenyl)pyrimidine; 5-(2-(3-fluorobenzyl)-1H-imidazol-4-yl)-2-(3-fluorophenyl) pyrimidine; 5-(2-(4-fluorobenzyl)-1H-imidazol-4-yl)-2-(3-fluorophenyl)pyrimidine; 2-(3-fluorophenyl)-5-(2-(pyridin-2-ylmethyl)-1H-imidazol-4-yl)pyrimidine; 2-(3-fluorophenyl)-5-(2-(pyridin-3-ylmethyl)-1H-imidazol-4-yl)pyrimidine; 2-(3-fluorophenyl)-5-(2-(pyridin-4-ylmethyl)-1H-imidazol-4-yl)pyrimidine; 2-(3-fluorophenyl)-5-(5-methyl-2-phenyl-1H-imidazol-4-yl)pyrimidine; 2-(3-fluorophenyl)-5-(1-methyl-2-phenyl-1H-imidazol-5-yl)pyrimidine; 2-(3-fluorophenyl)-5-(1-methyl-2-phenyl-1H-imidazol-4-yl)pyrimidine; 2-(3-fluorophenyl)-5-(5-methyl-2-(pyridin-3-yl)-1H-imidazol-4-yl)pyrimidine; 2-(3-fluorophenyl)-5-(1-methyl-2-(pyridin-3-yl)-1H-imidazol-5-yl)pyrimidine; and 2-(3-fluorophenyl)-5-(1-methyl-2-(pyridin-3-yl)-1H-imidazol-4-yl)pyrimidine; or an equivalent thereof, or an N-oxide thereof, or a pharmaceutically acceptable salt or solvate thereof.

Another exemplary embodiment may be a compound selected from the group consisting of: 2-(3-fluorophenyl)-5-(2-(1-(2,2,2-trifluoroethyl)piperidin-4-yl)-1H-imidazol-4-yl)pyrimidine; 2-(3-fluorophenyl)-5-(5-methyl-2-(1-(2,2,2-trifluoroethyl)piperidin-4-yl)-1H-imidazol-4-yl)pyridine; 5-(2-(1-benzylpiperidin-4-yl)-1H-imidazol-4-yl)-2-(3-fluorophenyl)pyrimidine; 5-(2-(1-benzylpiperidin-4-yl)-5-methyl-1H-imidazol-4-yl)-2-(3-fluorophenyl)pyridine; 5-(2-(1-benzylpiperidin-4-yl)-1-methyl-1H-imidazol-4-yl)-2-(3-fluorophenyl)pyridine; 5-(2-(1-benzylpiperidin-4-yl)-1-methyl-1H-imidazol-5-yl)-2-(3-fluorophenyl)pyridine; 5-(2-(1-(cyclopropylmethyl)piperidin-4-yl)-1H-imidazol-4-yl)-2-(3-fluorophenyl)pyrimidine; 3-(4-(4-(2-(3-fluorophenyl)pyrimidin-5-yl)-1H-imidazol-2-yl)piperidin-1-yl) pyridazine; 2-(3-fluorophenyl)-5-(2-(1-(1-methyl-1H-tetrazol-5-yl)piperidin-4-yl)-1H-imidazol-4-yl)pyrimidine; 4-(4-(2-(3-fluorophenyl)pyrimidin-5-yl)-1H-imidazol-2-yl)-N-methylpiperidine-1-carboxamide; ethyl 4-(4-(6-(3-fluorophenyl)pyridin-3-yl)-1H-imidazol-2-yl)piperidine-1-carboxylate; 1-(4-(4-(6-(3-fluorophenyl)pyridin-3-yl)-1H-imidazol-2-yl)piperidin-1-yl)butan-1-one; 2-(3-fluorophenyl)-5-(2-((1-(2,2,2-trifluoroethyl)piperidin-4-yl)methyl)-1H-imidazol-4-yl)pyrimidine; 2-(3-fluorophenyl)-5-(2-(1-(2,2,2-trifluoroethyl)piperidin-3-yl)-1H-imidazol-4-yl)pyridine; (R)-2-(3-fluorophenyl)-5-(2-(1-(2,2,2-trifluoroethyl)piperidin-3-yl)-1H-imidazol-4-yl)pyridine; (S)-2-(3-fluorophenyl)-5-(2-(1-(2,2,2-trifluoroethyl)piperidin-3-yl)-1H-imidazol-4-yl)pyridine; 5-(2-(1-benzylpiperidin-3-yl)-1H-imidazol-4-yl)-2-(3-fluorophenyl)pyridine; (R)-5-(2-(1-benzylpiperidin-3-yl)-1H-imidazol-4-yl)-2-(3-fluorophenyl)pyridine; (S)-5-(2-(1-benzylpiperidin-3-yl)-1H-imidazol-4-yl)-2-(3-fluorophenyl)pyridine; N-cyclopropyl-3-(4-(6-(3-fluorophenyl)pyridin-3-yl)-1H-imidazol-2-yl)piperidine-1-carboxamide; (R)-N-cyclopropyl-3-(4-(6-(3-fluorophenyl)pyridin-3-yl)-1H-imidazol-2-yl)piperidine-1-carboxamide; (R)-N-carboxamide; (S)-N-cyclopropyl-3-(4-(6-(3-fluorophenyl)pyridin-3-yl)-1H-imidazol-2-yl)piperidine-1-carboxamide; 2-(3-fluorophenyl)-5-(2-(1-(2,2,2-trifluoroethyl)piperidin-2-yl)-1H-imidazol-4-yl)pyridine; (S)-2-(3-fluorophenyl)-5-(2-(1-(2,2,2-trifluoroethyl)piperidin-2-yl)-1H-imidazol-4-yl)pyridine; and (R)-2-(3-fluorophenyl)-5-(2-(1-(2,2,2-trifluoroethyl)piperidin-2-yl)-1H-imidazol-4-yl)pyridine; or an equivalent thereof, or an N-oxide thereof, or a pharmaceutically acceptable salt or solvate thereof.

Another exemplary embodiment may be a compound selected from the group consisting of: 2-(3-fluorophenyl)-5-

(2-(1-(2,2,2-trifluoroethyl)pyrrolidin-3-yl)-1H-imidazol-4-yl)pyridine; (R)-2-(3-fluorophenyl)-5-(2-(1-(2,2,2-trifluoroethyl)pyrrolidin-3-yl)-1H-imidazol-4-yl)pyridine; (S)-2-(3-fluorophenyl)-5-(2-(1-(2,2,2-trifluoroethyl)pyrrolidin-3-yl)-1H-imidazol-4-yl)pyridine; 5-(2-(1-benzylpyrrolidin-3-yl)-1H-imidazol-4-yl)-2-(3-fluorophenyl)pyridine; (R)-5-(2-(1-benzylpyrrolidin-3-yl)-1H-imidazol-4-yl)-2-(3-fluorophenyl)pyridine; (S)-5-(2-(1-benzylpyrrolidin-3-yl)-1H-imidazol-4-yl)-2-(3-fluorophenyl)pyridine; 5-(2-(1-benzylpyrrolidin-3-yl)-5-methyl-1H-imidazol-4-yl)-2-(3-fluorophenyl)pyridine; (R)-5-(2-(1-benzylpyrrolidin-3-yl)-5-methyl-1H-imidazol-4-yl)-2-(3-fluorophenyl)pyridine; (S)-5-(2-(1-benzylpyrrolidin-3-yl)-5-methyl-1H-imidazol-4-yl)-2-(3-fluorophenyl)pyridine; 5-(2-(1-benzylpyrrolidin-3-yl)-1-methyl-1H-imidazol-4-yl)-2-(3-fluorophenyl)pyridine; (R)-5-(2-(1-benzylpyrrolidin-3-yl)-1-methyl-1H-imidazol-4-yl)-2-(3-fluorophenyl)pyridine; (S)-5-(2-(1-benzylpyrrolidin-3-yl)-1-methyl-1H-imidazol-4-yl)-2-(3-fluorophenyl)pyridine; 5-(2-(1-benzylpyrrolidin-3-yl)-1-methyl-1H-imidazol-5-yl)-2-(3-fluorophenyl)pyridine; (R)-5-(2-(1-benzylpyrrolidin-3-yl)-1-methyl-1H-imidazol-5-yl)-2-(3-fluorophenyl)pyridine; (S)-5-(2-(1-benzylpyrrolidin-3-yl)-1-methyl-1H-imidazol-5-yl)-2-(3-fluorophenyl)pyridine; ethyl 3-(4-(2-(3-fluorophenyl)pyrimidin-5-yl)-1H-imidazol-2-yl)pyrrolidine-1-carboxylate; (R)-ethyl 3-(4-(2-(3-fluorophenyl)pyrimidin-5-yl)-1H-imidazol-2-yl)pyrrolidine-1-carboxylate; (S)-ethyl 3-(4-(2-(3-fluorophenyl)pyrimidin-5-yl)-1H-imidazol-2-yl)pyrrolidine-1-carboxylate; 3-(4-(6-(3-fluorophenyl)pyridin-3-yl)-1H-imidazol-2-yl)-N-methylpyrrolidine-1-carboxamide; (R)-3-(4-(6-(3-fluorophenyl)pyridin-3-yl)-1H-imidazol-2-yl)-N-methylpyrrolidine-1-carboxamide; (S)-3-(4-(6-(3-fluorophenyl)pyridin-3-yl)-1H-imidazol-2-yl)-N-methylpyrrolidine-1-carboxamide; 2-(3-fluorophenyl)-5-(2-(1-(2,2,2-trifluoroethyl)pyrrolidin-2-yl)-1H-imidazol-4-yl)pyridine; (S)-2-(3-fluorophenyl)-5-(2-(1-(2,2,2-trifluoroethyl)pyrrolidin-2-yl)-1H-imidazol-4-yl)pyridine; (R)-2-(3-fluorophenyl)-5-(2-(1-(2,2,2-trifluoroethyl)pyrrolidin-2-yl)-1H-imidazol-4-yl)pyridine; 2-(3-fluorophenyl)-5-(2-(1-(2,2,2-trifluoroethyl)azetidin-3-yl)-1H-imidazol-4-yl)pyridine; 5-(2-(1-benzylazetidin-3-yl)-1H-imidazol-4-yl)-2-(3-fluorophenyl)pyridine; 5-(2-(1-benzylazetidin-3-yl)-5-methyl-1H-imidazol-4-yl)-2-(3-fluorophenyl)pyridine; and 1-(3-(4-(6-(3-fluorophenyl)pyridin-3-yl)-1H-imidazol-2-yl)azetidin-1-yl)butan-1-one; or an equivalent thereof, or an N-oxide thereof, or a pharmaceutically acceptable salt or solvate thereof.

Another exemplary embodiment may be a compound selected from the group consisting of: 2-phenoxy-5-(2-phenyl-1H-imidazol-4-yl)pyrimidine; 5-(2-(3-fluorophenyl)-1H-imidazol-4-yl)-2-phenoxypyrimidine; 2-phenoxy-5-(2-(pyridin-3-yl)-1H-imidazol-4-yl)pyrimidine; 5-(5-methyl-2-(pyridin-3-yl)-1H-imidazol-4-yl)-2-phenoxypyrimidine; 5-(1-methyl-2-(pyridin-3-yl)-1H-imidazol-4-yl)-2-phenoxypyrimidine; 5-(1-methyl-2-(pyridin-3-yl)-1H-imidazol-5-yl)-2-phenoxypyrimidine; 5-(2-(1-benzylpiperidin-4-yl)-5-methyl-1H-imidazol-4-yl)-2-phenoxypyrimidine; 5-(2-(1-benzylpiperidin-4-yl)-1-methyl-1H-imidazol-4-yl)-2-phenoxypyrimidine; 5-(2-(1-benzylpiperidin-4-yl)-1-methyl-1H-imidazol-5-yl)-2-phenoxypyrimidine; 5-(5-methyl-2-(pyridin-3-yl)-1H-imidazol-4-yl)-2-phenoxypyridine; 5-(1-methyl-2-(pyridin-3-yl)-1H-imidazol-4-yl)-2-phenoxypyridine; 5-(1-methyl-2-(pyridin-3-yl)-1H-imidazol-5-yl)-2-phenoxypyridine; 5-(2-(1-benzylpiperidin-4-yl)-5-methyl-1H-imidazol-4-yl)-2-phenoxypyridine; 5-(2-(1-benzylpiperidin-4-yl)-1-methyl-1H-imidazol-4-yl)-2-phenoxypyridine; 5-(2-(1-benzylpiperidin-4-yl)-1-methyl-1H-imidazol-5-yl)-2-phenoxypyridine; 5-(2-benzyl-1H-imidazol-4-yl)-2-phenoxypyrimidine; 2-phenoxy-5-(2-(1-(2,2,2-trifluoroethyl)piperidin-4-yl)-1H-imidazol-4-yl)pyrimidine; 5-(2-(1-benzylpiperidin-4-yl)-1H-imidazol-4-yl)-2-phenoxypyrimidine; 5-(2-(1-(cyclopropylmethyl)piperidin-4-yl)-1H-imidazol-4-yl)-2-phenoxypyrimidine; 3-(4-(4-(2-phenoxypyrimidin-5-yl)-1H-imidazol-2-yl)piperidin-1-yl)pyridazine; 5-(2-(1-(1-methyl-1H-tetrazol-5-yl)piperidin-4-yl)-1H-imidazol-4-yl)-2-phenoxypyrimidine; N-methyl-4-(4-(2-phenoxypyrimidin-5-yl)-1H-imidazol-2-yl)piperidine-1-carboxamide; 2-phenoxy-5-(2-((1-(2,2,2-trifluoroethyl)piperidin-4-yl)methyl)-1H-imidazol-4-yl)pyrimidine; ethyl 3-(4-(2-phenoxypyrimidin-5-yl)-1H-imidazol-2-yl)pyrrolidine-1-carboxylate; (R)-ethyl 3-(4-(2-phenoxypyrimidin-5-yl)-1H-imidazol-2-yl)pyrrolidine-1-carboxylate; (S)-ethyl 3-(4-(2-phenoxypyrimidin-5-yl)-1H-imidazol-2-yl)pyrrolidine-1-carboxylate; 5-(5-methyl-2-phenyl-1H-imidazol-4-yl)-2-phenoxypyrimidine; 5-(5-methyl-2-(1-(2,2,2-trifluoroethyl)piperidin-4-yl)-1H-imidazol-4-yl)-2-phenoxypyrimidine; and 5-(5-methyl-2-(1-(2,2,2-trifluoroethyl)piperidin-4-yl)-1H-imidazol-4-yl)-2-phenoxypyridine; or an equivalent thereof, or an N-oxide thereof, or a pharmaceutically acceptable salt or solvate thereof.

Another exemplary embodiment may be a compound selected from the group consisting of: 2-phenyl-5-(5-phenyl-1H-pyrazol-3-yl)pyrimidine; 5-(5-(3-fluorophenyl)-1H-pyrazol-3-yl)-2-phenylpyrimidine; 2-phenyl-5-(5-(pyridin-3-yl)-1H-pyrazol-3-yl)pyrimidine; 5-(5-benzyl-1H-pyrazol-3-yl)-2-phenylpyrimidine; 2-phenyl-5-(5-(1-(2,2,2-trifluoroethyl)piperidin-4-yl)-1H-pyrazol-3-yl)pyrimidine; 5-(5-(1-benzylpiperidin-4-yl)-1H-pyrazol-3-yl)-2-phenylpyrimidine; 5-(5-(1-(cyclopropylmethyl)piperidin-4-yl)-1H-pyrazol-3-yl)-2-phenylpyrimidine; 3-(4-(3-(2-phenylpyrimidin-5-yl)-1H-pyrazol-5-yl)piperidin-1-yl)pyridazine; 5-(5-(1-(1-methyl-1H-tetrazol-5-yl)piperidin-4-yl)-1H-pyrazol-3-yl)-2-phenylpyrimidine; N-methyl-4-(3-(2-phenylpyrimidin-5-yl)-1H-pyrazol-5-yl)piperidine-1-carboxamide; 2-phenyl-5-(5-((1-(2,2,2-trifluoroethyl)piperidin-4-yl)methyl)-1H-pyrazol-3-yl)pyrimidine; ethyl 3-(3-(2-phenylpyrimidin-5-yl)-1H-pyrazol-5-yl)pyrrolidine-1-carboxylate; (R)-ethyl 3-(3-(2-phenylpyrimidin-5-yl)-1H-pyrazol-5-yl)pyrrolidine-1-carboxylate; (S)-ethyl 3-(3-(2-phenylpyrimidin-5-yl)-1H-pyrazol-5-yl)pyrrolidine-1-carboxylate; and 5-(4-methyl-5-phenyl-1H-pyrazol-3-yl)-2-phenylpyrimidine; or an equivalent thereof, or an N-oxide thereof, or a pharmaceutically acceptable salt or solvate thereof.

Another exemplary embodiment may be a compound selected from the group consisting of: 3-(2-phenylpyrimidin-5-yl)-1H-pyrazole-5-carboxylic acid; methyl 3-(2-phenylpyrimidin-5-yl)-1H-pyrazole-5-carboxylate; ethyl 3-(2-phenylpyrimidin-5-yl)-1H-pyrazole-5-carboxylate; (4-methylpiperazin-1-yl)(3-(2-phenylpyrimidin-5-yl)-1H-pyrazol-5-yl)methanone; ethyl 3-(6-phenylpyridin-3-yl)-1H-pyrazole-5-carboxylate; (4-methylpiperazin-1-yl)(3-(6-phenylpyridin-3-yl)-1H-pyrazol-5-yl)methanone; ethyl 3-(2-(3-fluorophenyl)pyrimidin-5-yl)-1H-pyrazole-5-carboxylate; (3-(2-(3-fluorophenyl)pyrimidin-5-yl)-1H-pyrazol-5-yl)(4-methylpiperazin-1-yl)methanone; ethyl 3-(6-(3-fluorophenyl)pyridin-3-yl)-1H-pyrazole-5-carboxylate; (3-(6-(3-fluorophenyl)pyridin-3-yl)-1H-pyrazol-5-yl)(4-methylpiperazin-1-yl)methanone; ethyl 4-methyl-3-(2-phenylpyrimidin-5-yl)-1H-pyrazole-5-carboxylate; (4-methyl-3-(2-phenylpyrimidin-5-yl)-1H-pyrazol-5-yl)(4-methylpiperazin-1-yl)methanone; ethyl 1-methyl-3-(2-phenylpyrimidin-5-yl)-1H-pyrazole-5-carboxylate; (1-methyl-3-(2-phenylpyrimidin-5-yl)-1H-pyrazol-5-yl)(4-methylpiperazin-1-yl)methanone; ethyl 1-methyl-5-(2-phenylpyrimidin-5-yl)-1H-pyrazole-3-carboxylate; (1-methyl-5-(2-phenylpyrimidin-5-yl)-1H-pyrazol-3-yl)(4-methylpiperazin-1-yl)methanone; methyl 3-(2-phenoxypyrimidin-5-yl)-1H-pyrazole-5-carboxylate; ethyl 3-(2-phenoxypyrimidin-5-yl)-1H-pyrazole-5-carboxylate; (3-(2-benzoylpyrimidin-5-yl)-1H-pyrazol-5-yl)(4-methylpiperazin-1-yl)methanone; (3-(6-benzoylpyridin-3-yl)-1H-pyrazol-5-yl)(4-methylpiperazin-1-yl)methanone; and (4-methylpiperazin-1-yl)(3-(2-phenoxypyrimidin-5-yl)-1H-pyrazol-5-yl)methanone; or an equivalent thereof, or an N-oxide thereof, or a pharmaceutically acceptable salt or solvate thereof.

Another exemplary embodiment may be a compound selected from the group consisting of: 2-phenyl-5-(1-(1-(2,2,2-trifluoroethyl)piperidin-4-yl)-1H-imidazol-4-yl)pyrimidine; 5-(1-(1-benzylpiperidin-4-yl)-1H-imidazol-4-yl)-2-phenylpyrimidine; 5-(1-(1-benzylpiperidin-4-yl)-1H-imidazol-4-yl)-2-phenylpyridine; 5-(1-(1-benzylpiperidin-4-yl)-1H-imidazol-4-yl)-2-phenoxypyrimidine; 5-(1-(1-benzylpiperidin-4-yl)-1H-imidazol-4-yl)-2-phenoxypyridine; 2-phenyl-5-(1-(pyridin-3-ylmethyl)-1H-imidazol-4-yl)pyrimidine; 5-(1-benzyl-1H-imidazol-4-yl)-2-phenylpyrimidine; tert-butyl 4-(2-methyl-4-(2-phenylpyrimidin-5-yl)-1H-imidazol-1-yl)piperidine-1-carboxylate; 5-(1-benzyl-2-methyl-1H-imidazol-4-yl)-2-phenylpyrimidine; 2-phenyl-5-(1-(pyridin-3-yl)-1H-imidazol-4-yl)pyrimidine; 2-(3-fluorophenyl)-5-(1-(pyridin-3-ylmethyl)-1H-imidazol-4-yl)pyrimidine; and N-cyclopropyl-3-(4-(2-(3-fluorophenyl)pyrimidin-5-yl)-1H-imidazol-1-yl)pyrrolidine-1-carboxamide; or an equivalent thereof, or an N-oxide thereof, or a pharmaceutically acceptable salt or solvate thereof.

Another exemplary embodiment may be a compound selected from the group consisting of: 2-phenyl-5-(5-(pyridin-3-yl)-4H-1,2,4-triazol-3-yl)pyrimidine; 2-phenyl-5-(5-(pyridin-3-yl)-4H-1,2,4-triazol-3-yl)pyridine; 5-(1-methyl-5-(pyridin-3-yl)-1H-1,2,4-triazol-3-yl)-2-phenylpyrimidine; 5-(1-methyl-5-(pyridin-3-yl)-1H-1,2,4-triazol-3-yl)-2-phenylpyridine; 2-phenoxy-5-(5-(pyridin-3-yl)-4H-1,2,4-triazol-3-yl)pyrimidine; 2-phenoxy-5-(5-(pyridin-3-yl)-4H-1,2,4-triazol-3-yl)pyridine; 2-phenyl-5-(5-(1-(2,2,2-trifluoroethyl)piperidin-4-yl)-4H-1,2,4-triazol-3-yl)pyrimidine; and 2-phenyl-5-(5-(1-(2,2,2-trifluoroethyl)piperidin-4-yl)-4H-1,2,4-triazol-3-yl)pyridine; or an equivalent thereof, or an N-oxide thereof, or a pharmaceutically acceptable salt or solvate thereof.

Another exemplary embodiment may be a compound selected from the group consisting of: (5-(2-(3-fluorophenyl)-1H-imidazol-4-yl)pyrimidin-2-yl)(phenyl)methanone; phenyl(5-(2-(pyridin-3-yl)-1H-imidazol-4-yl)pyrimidin-2-yl)methanone; (5-(2-(1-benzylpiperidin-4-yl)-1H-imidazol-4-yl)pyrimidin-2-yl)(phenyl)methanone; (5-(2-(3-fluorophenyl)-5-methyl-1H-imidazol-4-yl)pyrimidin-2-yl)(phenyl)methanone; (5-(5-methyl-2-(pyridin-3-yl)-1H-imidazol-4-yl)pyrimidin-2-yl)(phenyl)methanone; (5-(2-(1-benzylpiperidin-4-yl)-5-methyl-1H-imidazol-4-yl)pyrimidin-2-yl)(phenyl)methanone; (5-(2-(3-fluorophenyl)-1-methyl-1H-imidazol-4-yl)pyrimidin-2-yl)(phenyl)methanone; (5-(1-methyl-2-(pyridin-3-yl)-1H-imidazol-4-yl)pyrimidin-2-yl)(phenyl)methanone; and (5-(2-(1-benzylpiperidin-4-yl)-1-methyl-1H-imidazol-4-yl)pyrimidin-2-yl)(phenyl)methanone; or an equivalent thereof, or an N-oxide thereof, or a pharmaceutically acceptable salt or solvate thereof.

Another exemplary embodiment may be a compound selected from the group consisting of: 4-methyl-2-phenyl-5-(2-(pyridin-3-yl)-1H-imidazol-5-yl)thiazole; 2-(3-fluorophenyl)-4-methyl-5-(2-(pyridin-3-yl)-1H-imidazol-5-yl)thiazole; 4-methyl-2-phenyl-5-(2-(1-(2,2,2-trifluoroethyl)piperidin-4-yl)-1H-imidazol-5-yl)thiazole; 4-methyl-2-phenyl-5-(2-(1-(pyridazin-3-yl)piperidin-1-yl)-1H-imidazol-5-yl)thiazole; 4-methyl-2-phenyl-5-(2-(1-(2,2,2-trifluoroethyl)piperidin-3-yl)-1H-imidazol-5-yl)thiazole; and 5-(2-(1-benzylpyrrolidin-3-yl)-1H-imidazol-5-yl)-4-methyl-2-phenylthiazole; or an equivalent thereof, or an N-oxide thereof, or a pharmaceutically acceptable salt or solvate thereof.

The exemplary embodiments may also be directed to a method of preventing or treating a disease or condition mediated at least in part by prostaglandin $D_2$ produced by H-PGDS, in a subject in need of such treatment, comprising administering to the subject a therapeutically effective amount of a compound of formula (I) or (II), or an equivalent thereof, or an N-oxide thereof, or a pharmaceutically acceptable salt or solvate thereof; the use of a compound of formula (I) or (II), or an equivalent thereof, or an N-oxide thereof, or a pharmaceutically acceptable salt or solvate thereof, for the manufacture of a medicament for preventing or treating a disease or condition mediated at least in part by prostaglandin $D_2$ produced by H-PGDS; a compound of formula (I) or (II), or an equivalent thereof, or an N-oxide thereof, or a pharmaceutically acceptable salt or solvate thereof, for use as a medicament; a compound of formula (I) or (II), or an equivalent thereof, or an N-oxide thereof, or a pharmaceutically acceptable salt or solvate thereof, for use in the prevention or treatment of a disease or condition mediated at least in part by prostaglandin $D_2$ produced by H-PGDS; a pharmaceutical composition comprising a compound of formula (I) or (II), or an equivalent thereof, or an N-oxide thereof, or a pharmaceutically acceptable salt or solvate thereof, and a pharmaceutically acceptable excipient; a pharmaceutical composition for the prevention and treatment of a disease or condition mediated at least in part by prostaglandin $D_2$ produced by H-PGDS comprising a compound of formula (I) or (II), or an equivalent thereof, or an N-oxide thereof, or a pharmaceutically acceptable salt or solvate thereof.

The diseases and conditions mediated at least in part by prostaglandin $D_2$ produced by H-PGDS may include allergy and allergic inflammation. Diseases and conditions of this kind may be allergic respiratory conditions such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, airways disease that may be associated with pulmonary hypertension, acute lung injury, bronchiectasis, sinusitis, allergic conjunctivitis, or atopic dermatitis, particularly asthma or chronic obstructive pulmonary disease.

Types of asthma may include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, exertion asthma, allergen-induced asthma, cold air induced asthma, occupational asthma, infective asthma caused by bacterial, fungal, protozoal, or viral infection, non-allergic asthma, incipient asthma, wheezy infant syndrome, and bronchiolytis.

Included in the use of the compounds of formula (I) and (II) for the treatment of asthma, may be palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

Other diseases and conditions that may be mediated, at least in part, by prostaglandin D2 produced by H-PGDS are arthritis (especially rheumatoid arthritis), irritable bowel diseases (such as Crohns disease and ulcerative colitis), irritable bowel syndrome, inflammatory pain, chronic pain, muscular necrosis (such as Duchenne muscular dystrophy), skin inflammation and irritation (such as eczema), niacin-induced skin flushing, cealic type disease (e.g. as a result of lactose intolerance), wound healing, and dermal scarring (Kapoor, M., Kojima, F., Yang, L., and Crofford, L. J. *Prostaglandins Leukot. Essent. Fatty Acids,* 76(2), 2007, 103-112). Chronic pain conditions may include neuropathic pain conditions (such as painful diabetic neuropathy and postherpetic neuralgia), carpel tunnel syndrome, back pain, headache, cancer pain, arthritic pain and chronic post-surgical pain.

The exemplary embodiments may also be directed to any of the uses, methods, or compositions as defined above wherein the compound of formula (I) or (II), or an equivalent thereof, or an N-oxide thereof, or a pharmaceutically acceptable salt or solvate thereof, that is used in combination with another pharmacologically active compound. Specific combinations useful according to the exemplary embodiments may include combinations comprising a compound of formula (I) or (II), or an equivalent thereof, or an N-oxide thereof, or a pharmaceutically acceptable salt or solvate thereof., and (i) a glucocorticosteroid or DAGR (dissociated agonist of the corticoid receptor); (ii) a $\beta_2$ agonist, an example of which is a long-acting $\beta_2$ agonist; (iii) a muscarinic M3 receptor antagonist or anticholinergic agent; (iv) a histamine receptor antagonist or inverse agonist, which may be an H1 or an H3 antagonist or inverse agonist; (v) a 5-lipoxygenase inhibitor; (vi) a thromboxane inhibitor; (vii) an $LTD_4$ inhibitor; (viii) a kinase inhibitor; or (ix) a vaccine. Generally, the compounds of the combination may be administered together as a formulation in association with one or more pharmaceutically acceptable excipients.

Besides being useful for human treatment, compounds of formula (I) or (II) may also be useful for veterinary treatment of companion animals, exotic animals, and farm animals.

When used in the present application, the following abbreviations have the meaning set out below: Ac is acetyl; ACN is acetonitrile; $BBr_3$ is boron tribromide; Bn is benzyl; $BnNH_2$ is benzylamine; BSA is bovine serum albumin; $CH_2Cl_2$ is dichloromethane; $CHCl_3$ is chloroform; $CDCl_3$ is deuterochloroform; dba is dibenzylideneacetone; DCC is N,N'-dicyclohexylcarbodiimide; DCM is dichloromethane; DME is 1,2-dimethoxyethane; DMF is N,N-dimethylformamide; DMSO is dimethyl sulfoxide; DBU is 1,8-diazabicyclo [5.4.0]undec-7-ene; EDC/EDAC is N-(3-dimethylaminopropyl)-N-ethylcarbodiimide hydrochloride; EDTA is ethylenediaminetetraacetic acid; EIA is enzyme immunoassay; Et is ethyl; $Et_3N$ is triethylamine; HCl is hydrogen chloride; HOBt is 1-hydroxybenzotriazole; Me is methyl; MTBE is methyl tert-butyl ether; NaOMe is sodium methoxide; NMP is 1-methyl-2-pyrrolidinone; PG represents a chemical protecting group; Ph is phenyl; $Pd(PPh_3)_4$ is tetrakis(triphenylphosphine)palladium; $PhB(OH)_2$ is benzeneboronic acid, also known as phenylboronic acid; PhMe is toluene; rt is room temperature; TBAB is tetrabutylammonium bromide; t-Bu is tert-butyl; THF is tetrahydrofuran; TLC is thin layer chromatography; and Tris-HCl is 2-amino-2-(hydroxymethyl)-1,3-propanediol hydrochloride.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

The phrase "therapeutically effective" is intended to qualify the amount of compound or pharmaceutical composition, or the combined amount of active ingredients in the case of combination therapy. This amount or combined amount may achieve the goal of treating the relevant condition.

The term "treatment," as used herein to describe the exemplary embodiments and unless otherwise qualified, means administration of the compound, pharmaceutical composition, or combination to effect preventative, palliative, supportive, restorative, or curative treatment. The term treatment encompasses any objective or subjective improvement in a subject with respect to a relevant condition or disease.

The term "preventative treatment," as used herein to describe the exemplary embodiments, means that the compound, pharmaceutical composition, or combination may be administered to a subject to inhibit or stop the relevant condition from occurring in a subject, particularly in a subject or member of a population that may be significantly predisposed to the relevant condition.

The term "palliative treatment," as used herein to describe the exemplary embodiments, means that the compound, pharmaceutical composition, or combination may be administered to a subject to remedy signs and/or symptoms of a condition, without necessarily modifying the progression of, or underlying etiology of, the relevant condition.

The term "supportive treatment," as used herein to describe the exemplary embodiments, means that the compound, pharmaceutical composition, or combination may be administered to a subject as part of a regimen of therapy, but that such therapy is not limited to administration of the compound, pharmaceutical composition, or combination. Unless otherwise expressly stated, supportive treatment may embrace preventative, palliative, restorative, or curative treatment, particularly when the compounds or pharmaceutical compositions are combined with another component of supportive therapy.

The term "restorative treatment," as used herein to describe the exemplary embodiments, means that the compound, pharmaceutical composition, or combination may be administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, a reduction in relapses, improvement in quality of life, and the like.

The term "curative treatment," as used herein to describe the exemplary embodiments, means that the compound, pharmaceutical composition, or combination may be administered to a subject for the purpose of bringing the disease or disorder into complete remission, or that the disease or disorder in undetectable after such treatment.

The term "alkyl," alone or in combination, means an acyclic radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, heptyl, octyl, and the like. Where no specific substitution is specified, alkyl radicals may be optionally substituted with groups consisting of hydroxy, sulfhydryl, methoxy, ethoxy, amino, cyano, chloro, and fluoro. Examples of such substituted alkyl radicals include chloroethyl, hydroxyethyl, cyanobutyl, aminopentyl and the like.

The carbon atom content of various hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, '($C_1$-$C_6$)-alkyl' refers to alkyl of one to six carbon atoms, inclusive.

The terms "hydroxy" and "hydroxyl," as used herein, mean an OH radical.

The term "sulfhydryl," as used herein, means an SH radical.

The term "oxo" means a doubly bonded oxygen.

The term "alkoxy" means a radical comprising an alkyl radical that is bonded to an oxygen atom, such as a methoxy radical. Preferred alkoxy radicals have one to about six carbon atoms. Examples of such radicals include methoxy, ethoxy, propoxy, isopropoxy, butoxy, and tert-butoxy.

The term "aryl" means a fully unsaturated mono-or multi-ring cycloalkyl having a cyclic array of p-orbitals containing 4n+2 electrons, including, but not limited to, substituted or unsubstituted phenyl, naphthyl, or anthracenyl optionally fused to a carbocyclic radical wherein aryl may be optionally substituted with one or more substituents from the group consisting of halo, methoxy, ethoxy, ($C_1$-$C_6$)-alkyl, phenyl, O-phenyl, cyano, nitro, hydroxyl, sulfhydryl, or trifluoromethyl.

The term "halo," as used herein, means one of the following group consisting of fluoro, chloro, bromo, or iodo.

The terms "heterocycle", "heterocyclic ring system," and "heterocyclyl" refer to a saturated or unsaturated mono- or multi-ring cycloalkyl wherein one or more carbon atoms is replaced by N, S, or O. The terms "heterocycle", "heterocyclic ring system," and "heterocyclyl" include fully saturated ring structures such as azetidinyl, piperazinyl, dioxanyl, tetrahydrofuranyl, oxiranyl, aziridinyl, morpholinyl, pyrrolidinyl, piperidinyl, thiazolidinyl, and others. The terms "heterocycle", "heterocyclic ring system," and "heterocyclyl" also include partially unsaturated ring structures such as dihydrofuranyl, pyrazolinyl, imidazolinyl, pyrrolinyl, chromanyl, dihydrothiphenyl, and others.

A preferred non-aromatic heterocyclic group is a five- or six-membered saturated or partially unsaturated heterocyclic group containing one or two nitrogen or oxygen groups, optionally substituted by one or more of ($C_1$-$C_6$)-alkyl, ($C_1$-$C_6$)-fluoroalkyl, ($C_3$-$C_6$)-cycloalkyl, hydroxy($C_3$-$C_6$)-cycloalkyl, ($C_2$-$C_6$)-alkenyl, ($C_2$-$C_6$)-alkynyl, halo, oxo, hydroxyl, —$(CH_2)_p$OH, —$OR^8$, —$(CH_2)_p OR^8$, sulfhydryl, —$(CH_2)_p$SH, —$SR^8$, —$(CH_2)_p SR^8$, —$NR^8R^9$, —$(CH_2)_p NR^8R^9$, —$CO_2R^8$, —$(CH_2)_p CO_2R^8$, —$CONR^8R^9$, —$(CH_2)_p CONR^8R^9$, cyano, or —$(CH_2)_p CN$, wherein p is 1, 2, or 3 and each $R^8$ and $R^9$ is independently hydrogen or ($C_1$-$C_6$)-alkyl optionally substituted with —OH or —O—(($C_1$-$C_6$)-alkyl). Preferred examples of non-aromatic heterocyclic groups include azetidinyl, pyrrolidinyl, tetrahydrofuranyl, piperidinyl, piperazinyl and morpholinyl (optionally substituted as specified above).

The term "heteroaryl" refers to an aromatic heterocyclic group. Heteroaryl is preferably: (a) a five-membered aromatic heterocyclic group containing either (i) 1-4 nitrogen atoms or (ii) 0-3 nitrogen atoms and 1 oxygen or 1 sulfur atom; (b) a six-membered aromatic heterocyclic group containing 1-3 nitrogen atoms; (c) a nine-membered bicyclic heterocyclic group containing either (i) 1-5 nitrogen atoms or (ii) 0-4 nitrogen atoms and 1 oxygen or 1 sulfur atom; or (d) a ten-membered bicyclic aromatic heterocyclic group containing 1-6 nitrogen atoms; each of said groups (a)-(d) being optionally substituted by one or more of ($C_1$-$C_6$)-alkyl, ($C_1$-$C_6$)-fluoroalkyl, ($C_3$-$C_6$)-cycloalkyl, hydroxy($C_3$-$C_6$)-cycloalkyl, ($C_2$-$C_6$)-alkenyl, ($C_2$-$C_6$)-alkynyl, halo, oxo, hydroxyl, —$(CH_2)_p$OH, —$OR^8$, —$(CH_2)_p OR^8$, sulfhydryl, —$(CH_2)_p$SH, —$SR^8$, —$(CH_2)_p SR^8$, —$NR^8R^9$, —$(CH_2)_p NR^8R^9$, —$CO_2R^8$, —$(CH_2)_p CO_2R^8$, —$CONR^8R^9$, —$(CH_2)_p CONR^8R^9$, cyano, or —$(CH_2)_p CN$; wherein p is 1, 2, or 3 and each $R^8$ and $R^9$ is independently hydrogen or ($C_1$-$C_6$)-alkyl optionally substituted with —OH or —O—(($C_1$-$C_6$)-alkyl). Examples of "heteroaryl" include pyridyl, pyrimidinyl, pyridazinyl, pyrazinyl, thionyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted as specified above.

In "heterocycle" or "heteroaryl," the point of attachment to the molecule of interest may be at a heteroatom or elsewhere within the ring.

The term "cycloalkyl" means a mono- or multi-ringed cycloalkyl wherein each ring contains three to ten carbon atoms, preferably three to six carbon atoms. "Cycloalkyl" is preferably a monocyclic cycloalkyl containing from three to six carbon atoms. Examples include cyclopropyl, cyclobutyl, cyclopentyl, and cyclohexyl.

The symbols

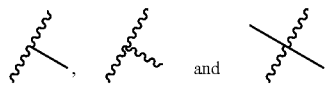

denote the point of attachment of a substituent.

The wavy line attached to a double bond, as denoted here:

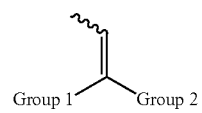

represents undefined double bond geometry, in that the symbol allows for either cis (Z) or trans (E) geometry.

As used herein, the terms "co-administration," "co-administered," and "in combination with," referring to a combination of a compound of formula (I) or (II) and one or more other therapeutic agents, is intended to mean, and does refer to and include the following:

(i) simultaneous administration of such combination of a compound of formula (I) or (II) and a further therapeutic agent to a patient in need of treatment, when such components are formulated together into a single dosage form which releases said components at substantially the same time to said patient;

(ii) substantially simultaneous administration of such a combination of a compound of formula (I) or (II) and a further therapeutic agent to a patient in need of treatment, when such components are formulated apart from each other into separate dosage forms which are taken at substantially the same time by said patient, whereupon said components are released at substantially the same time to said patient;

(iii) sequential administration of such a combination of a compound of formula (I) or (II) and a further therapeutic agent to a patient in need of treatment, when such components are formulated apart from each other into separate dosage forms which are taken at consecutive times by said patient with a significant time interval between each administration, whereupon said components are released at substantially different times to said patient; and (iv) sequential administration of such a combination of a compound of formula (I) or (II) and a further therapeutic agent to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

The term "excipient" is used herein to describe any ingredient other than a compound of formula (I) or (II). The choice of excipient will to a large extent depend on factors such as the particular mode of administration, the effect of the excipient on solubility and stability, and the nature of the dosage form. The term "excipient" encompasses diluents, carrier, or adjuvant.

Pharmaceutically acceptable salts of the compounds of formula (I) or (II) include the acid addition and base salts thereof.

Suitable acid addition salts are formed by acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, propionate, pyroglutamate, saccharate, stearate, succinate, tannate, tartrate, tosylate, trifluoroacetate, naphthalene-1,5-disulfonic acid, and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulfate and hemicalcium salts. For a review on suitable salts, see *Handbook of Pharmaceutical Salts: Properties, Selection, and Use*, by Stahl and Wermuth (Wiley-VCH, 2002).

Pharmaceutically acceptable salts of compounds of formulas (I) or (II) may be prepared by one or more of three methods:

(i) by reacting the compound of formula (I) or (II) with the desired acid or base;

(ii) by removing an acid- or base-labile protecting group from a suitable precursor of the compound of formula (I) or (II) or by a ring-opening a suitable cyclic precursor, for example, a lactone or lactam, using the desired acid or base; or (iii) by converting one salt of the compound of formula (I) or (II) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of formula (I) or (II) may also exist in unsolvated and solvated forms. The term "solvate" is used herein to describe a molecular complex comprising the compound of formula (I) or (II), or a pharmaceutically acceptable salt thereof, and one or more pharmaceutically acceptable solvent molecules, for example, ethanol or water. The term "hydrate" is employed when said solvent is water.

Also included herein are multi-component complexes other than salts and solvates wherein the compound of formula (I) or (II) and at least one other component are present in stoichiometric or non-stoichiometric amounts.

The compounds of formula (I) or (II) may exist in a continuum of solid states ranging from fully amorphous to fully crystalline.

The compounds of formula (I) or (II) may also exist in a mesomorphic state (mesophase or liquid crystal) when subjected to suitable conditions. The mesomorphic state is intermediate between the true crystalline state and the true liquid state (either melt or solution).

Hereinafter all references to compounds of formula (I) or (II) (also referred to as compounds of the invention) include references to salts, solvates, multi-component complexes, and liquid crystals thereof and to solvates, multi-component complexes, and liquid crystals of salts thereof.

Also included herein are all polymorphs and crystal habits of compounds of formula (I) or (II), prodrugs, and isomers thereof (including optical, geometric, and tautomeric isomers) and isotopically-labeled forms thereof.

As indicated, so-called 'prodrugs' of the compounds of formulas (I) and (II) are also within the scope of the invention. Thus certain derivatives of a compound of formula (I) or (II) which may have little or no pharmacological activity themselves can, when administered into or onto the body, be converted into a compound of formula (I) or (II) having the desired activity, for example, by hydrolytic cleavage. Such derivatives are referred to as 'prodrugs.' Further information on the use of prodrugs may be found in *Prodrugs as Novel Delivery Systems*, Vol. 14, ACS Symposium Series (T. Higuchi and W, Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formulas (I) and (II) with certain moieties known to those skilled in the art as 'promoieties' as described, for example, in *Design of Prodrugs*, by H. Bundgaard (Elsevier, 1985).

Some examples of prodrugs in accordance with the exemplary embodiments include:

(i) where a compound of formulas (I) or (II) contains a carboxylic acid functionality (—$CO_2H$), an ester thereof; for example, a compound wherein the hydrogen of the carboxylic acid functionality of the compound of formula (I) or (II) is replaced by ($C_1$-$C_8$)-alkyl;

(ii) where a compound of formulas (I) or (II) contains an alcohol functionality (—OH), an ether thereof; for example, a compound wherein the hydrogen of the alcohol functionality of the compound of formula (I) or (II) is replaced by ($C_1$-$C_6$)-alkanoyloxymethyl; and (iii) where a compound of formulas (I) or (II) contains a primary or secondary amino functionality (—$NH_2$ or —NHR where R is not H), an amide thereof; for example, a compound wherein, as the case may be, one or both hydrogens of the amino functionality of the compound of formula (I) or (II) is/are replaced by ($C_1$-$C_{10}$)-alkanoyl.

Further examples of replacement groups in accordance with the foregoing examples and examples of other prodrug types may be found in the aforementioned references.

Moreover, certain compounds of formulas (I) and (II) may themselves act as prodrugs of other compounds of formulas (I) and (II), respectively.

Also included within the scope of the invention are metabolites of compounds of formulas (I) and (II), that is, compounds formed in vivo upon administration of the drug.

Also included within the scope of the invention are compounds of formulas (I) and (II) that are all pharmaceutically acceptable isotopically labeled compounds of formulas (I) and (II) wherein one or more atoms are replaced by atoms having the same atomic number, but an atomic mass or mass number different from the atomic mass or mass number which predominates in nature; for example, a compound of formula (I) or (II) for which one of the hydrogen atoms ($^1H$) is replaced with a deuterium (D, or $^2H$) or tritium (T, or $^3H$) isotope. Another example includes a compound of formula (I) or (II) for which one of the carbon-12 atoms ($^{12}C$) is replaced with a carbon-14 ($^{14}C$) isotope. Isotopically labeled compounds of formulas (I) and (II) can generally be prepared by conventional techniques known to those ordinarily skilled in the art or by processes analogous to those described in the accompanying Examples using an appropriately isotopically labeled reagent in place of the non-labeled reagent previously employed.

Also included within the scope of the invention are all stereoisomers, geometric isomers and tautomeric forms of the compounds of formulas (I) and (II), including compounds that exhibit more than one type of isomerism, and mixtures of one or more thereof.

Cis/trans isomers may be separated by conventional techniques well known to those ordinarily skilled in the art; for example, chromatography and fractional crystallization.

Conventional techniques for preparation and isolation of individual enantiomers include chiral synthesis from a suitable optically pure precursor or resolution of the racemate (or the racemate salt or derivative) using, for example, chiral high pressure liquid chromatography (HPLC). Alternatively, the racemate (or racemic precursor) may be reacted with a suitable optically active compound, for example, an alcohol, or, in the case where the compound of formula (I) or (II) contains an acidic or basic moiety, a base or an acid such as 1-phenethylamine or tartaric acid. The resulting diastereomeric mixture may be separated by chromatography and/or fractional crystallization and one or both of the diastereomers converted into the corresponding pure enantiomer(s) by means well known to those ordinarily skilled in the art.

Compounds of the exemplary embodiments of formulas (I) and (II) may be administered orally, topically, transdermally, intranasally, by inhalation, directly into the bloodstream, into muscle, into an internal organ, into the eye, into the ear, into the rectum, or by other means.

The compounds herein, their methods of preparation and their biological activity will appear more clearly from the examination of the following examples that are presented as an illustration only and are not to be considered as limiting the invention in its scope. Compounds herein are identified, for example, by the following analytical methods.

Mass spectra (MS) methods include positive electrospray ionization ($ESI^+$), negative electrospray ionization ($ESI^-$), positive atmospheric pressure chemical ionization ($APCI^+$), or negative atmospheric pressure chemical ionization ($APCI^-$).

400 MHz proton nuclear magnetic resonance spectra ($^1H$ NMR) are recorded at ambient temperature using either a Bruker (300 MHz) or a Varian INOVA (400 MHz) nuclear magnetic resonance spectrometer. In the $^1H$ NMR chemical shifts (δ) are indicated in parts per million (ppm) with reference to tetramethylsilane (TMS) as the internal standard.

EXAMPLES

Examples 1-13, 32-33, and 44 are imidazole compounds that may be prepared according to the general synthetic route illustrated in Scheme 1. Palladium-assisted coupling of 5-bromo-2-iodopyridine or 5-bromo-2-iodopyrimidine (1) with the appropriate arylboronic acid (2) provided the corresponding 2-aryl-5-bromopyridine or 2-aryl-5-bromopyrimidine intermediate (3). A subsequent palladium-assisted coupling of an intermediate (3) with a 1-benzyl-2-$R^2$-substituted imidazole intermediate (4), which was prepared as illustrated in Scheme 2, provides the corresponding intermediate generally illustrated as structure (5). Debenzylation catalyzed with palladium on carbon affords the corresponding 5-(imidazol-4-yl)-pyridine or 5-(imidazol-4-yl)-pyrimidine (6).

For each of the examples and schemes below, temperatures, measurements, and time references are approximations and are not intended to be limited to the actual values listed.

Scheme 1: General synthesis of 5-(imidazol-4-yl)-pyridines and 5-(imidazol-4-yl)-pyrimidines

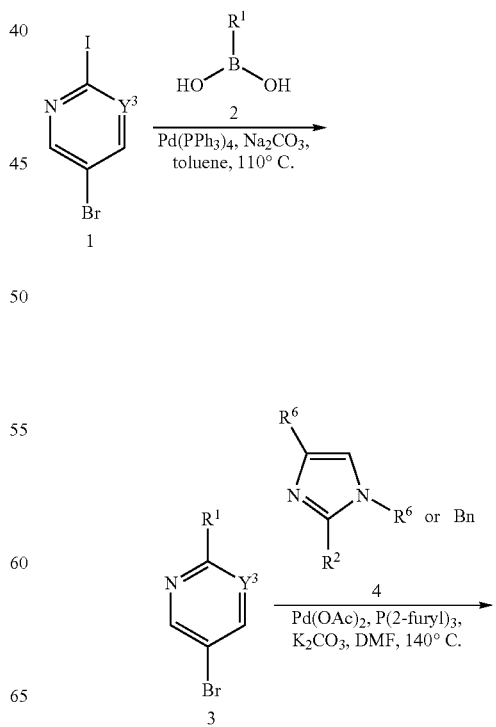

-continued

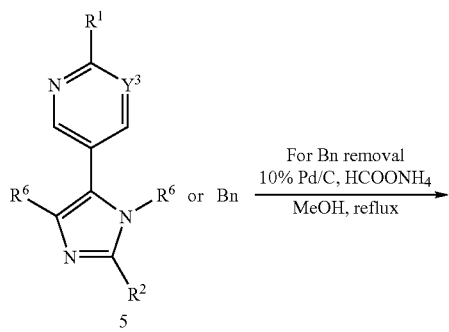

5

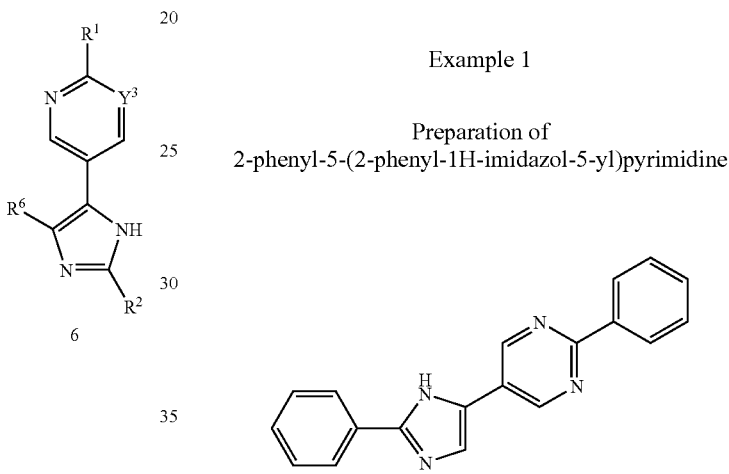

| Ex. | R$^6$ | R$^7$ | Y$^3$ | H-PGDS FPBA IC$_{50}$ (μM) | H-PGDS Inhibitor EIA IC$_{50}$ (μM) |
|---|---|---|---|---|---|
| 1 | H | H | N | 0.25 | 0.012 |
| 2 | H | H | CH | 0.48 | 0.097 |
| 3 | H | Me | N | 0.625 | 0.25 |
| 4 | Me | H | N | 0.45 | 0.082 |

Example 1

Preparation of 2-phenyl-5-(2-phenyl-1H-imidazol-5-yl)pyrimidine

Step A: Preparation of 5-bromo-2-phenylpyrimidine

A mixture consisting of 5-bromo-2-iodopyrimidine (Bridge Organics, 10.0 g, 35.1 mmol), benzene boronic acid (Alfa Aesar, 4.25 g, 35.1 mmol), tetrakis(triphenylphosphine) palladium (Strem, 0.405 g, 0.351 mmol), toluene (150 mL), and a 2 M aqueous sodium carbonate solution (35 mL) was stirred at 115° C. (degrees Celsius) under a nitrogen atmosphere for 16 hours. After cooling to room temperature, the mixture was partitioned between chloroform (250 mL) and brine (200 mL). The phases were separated and the organic phase was dried over anhydrous magnesium sulfate, and concentrated under reduced pressure to give an orange oil (9.1 g). The crude product was purified by flash silica column chromatography. Elution through a 500-g Analogix® flash silica cartridge with 100% hexanes afforded the title intermediate as a white solid (3.15 g, 38% yield). R$_f$ 0.69 with 9:1 v/v Scheme 2: General synthesis of 1-benzyl-2-R$^2$-substituted imidazole intermediates

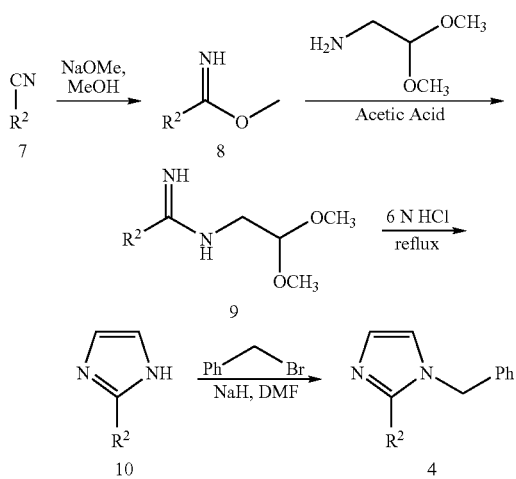

hexanes-ethyl acetate; $^1$H-NMR (400 MHz; CDCl$_3$) δ 8.83 (s, 2H), 8.44-8.38 (m, 2H), 7.52-7.46 (m, 3H); MS (APCI$^+$) m/z 236.9 (M+1).

Step B: Preparation of
1-benzyl-2-phenyl-1H-imidazole

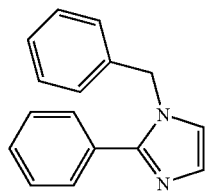 [SMILES: c1ccc(Cn2ccnc2-c2ccccc2)cc1]

To a mixture consisting of 2-phenylimidazole (TCI America, 3.0 g, 21 mmol) and N,N-dimethylformamide (40 mL) was added 60% sodium hydride in mineral oil (0.92 g, 23 mmol). After stirring for one hour at room temperature, a solution consisting of benzyl bromide (Aldrich, 2.73 mL, 22.9 mmol) in N,N-dimethylformamide (5 mL) was added dropwise while stirring. After stirring at room temperatures for 12 hours the reaction was complete as observed by TLC. The reaction mixture was partitioned between ethyl acetate (150 mL) and water (100 mL). The phases were separated and the organic layer was washed with brine (150 mL), and was subsequently dried over anhydrous magnesium sulfate. Concentration under reduced pressure afforded the crude product as an orange oil (4.2 g). The product was purified by flash silica column chromatography. Elution through a 80-g Silicycle® flash silica cartridge with gradient of 5% to 30% ethyl acetate in hexanes afforded the title intermediate as a colorless oil (3.21 g, 66% yield); R$_f$ 0.65 with 9:1 v/v dichloromethane-methanol; $^1$H-NMR (400 MHz; CDCl$_3$) δ 7.57-7.53 (m, 2H), 7.42-7.28 (m, 6H), 7.19 (d, 1H), 7.11-7.07 (m, 2H), 6.97 (d, 1H), 5.22 (s, 2H).

Step C: Preparation of 5-(1-benzyl-2-phenyl-1H-imidazol-5-yl)-2-phenylpyrimidine

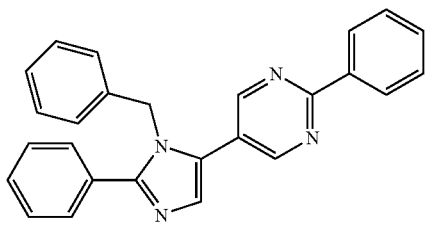 [SMILES: c1ccc(Cn2c(-c3cnc(-c4ccccc4)nc3)cnc2-c2ccccc2)cc1]

To a mixture consisting of 5-bromo-2-phenylpyrimidine (1.2 g, 5.1 mmol), palladium (II) acetate (Strem, 0.048 g, 0.21 mmol), tris(2-furyl)phosphine (TCI America, 0.098 g, 0.43 mmol) and potassium carbonate (1.17 g, 8.52 mmol) was added a solution consisting of 1-benzyl-2-phenyl-1H-imidazole (1.0 g, 4.3 mmol) in N,N-dimethylformamide (10 mL). The reaction mixture was brought to reflux at 140° C. (degrees Celsius) while under a N$_2$ atmosphere. After stirring for 16 hours at reflux the solution was cooled to room temperature. The reaction mixture was partitioned between ethyl acetate (250 mL) and saturated aqueous ammonium chloride (100 mL). The phases were separated and the organic layer was washed with brine (150 mL), and was subsequently dried over anhydrous magnesium sulfate. Concentration under reduced pressure affords the crude product as an orange oil (0.658 g). The product was purified by flash silica column chromatography. Elution through a 80-g Silicycle® flash silica cartridge with gradient of 5% to 30% ethyl acetate in hexanes afforded the title intermediate (0.495 g, 30% yield); R$_f$ 0.38 with 1:1 v/v ethyl acetate-hexane; $^1$H-NMR (400 MHz; CDCl$_3$) δ 8.7 (s, 2H), 8.4 (m, 2H), 7.6 (m, 2H), 7.5-7.25 (m, 10H), 6.9 (m, 2H), 5.32 (s, 2H); MS (ESI$^+$) m/z 389.2 (M+1); H-PGDS FPBA IC$_{50}$: 15 μM.

Step D: Preparation of
2-phenyl-5-(2-phenyl-1H-imidazol-5-yl)pyrimidine

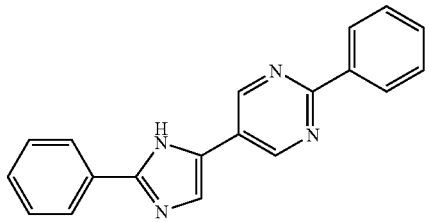

To a solution consisting of 5-(1-benzyl-2-phenyl-1H-imidazol-5-yl)-2-phenylpyrimidine (0.495 g, 1.27 mmol) in methanol (100 mL) was added ammonium formate (Aldrich, 0.804 g, 12.7 mmol) and 10% palladium on carbon (Alfa Aesar, 0.500 g). The reaction mixture was brought to reflux at 70° C. for 16 hours. After cooling the solution to room temperature, the crude reaction mixture was filtered over a bed of Celite, which was rinsed with additional methanol (300 mL). Concentration of the filtrate afforded an off-white solid. The product was purified by flash silica column chromatography. Elution through a 40-g Silicycle® flash silica cartridge with gradient of 100% dichloromethane to 5% methanol in dichloromethane afforded the title compound as a white solid (0.218 g, 57% yield); R$_f$ 0.56 with 95:5 v/v dichloromethane-methanol; melting point 253° C.; $^1$H-NMR (400 MHz; DMSO-d$_6$) δ 9.3 (s, 2H), 8.4 (m, 2H), 8.05 (m, 3H), 7.55-7.35 (m, 6H); MS (ESI$^+$) m/z 299.1 (M+1); H-PGDS FPBA IC$_{50}$: 0.25 μM; H-PGDS inhibitor EIA IC$_{50}$: 0.012 μM.

Examples 2-12 were generally prepared according to the procedures described in Example 1. Exceptions are noted in each Example.

Example 2

Preparation of
2-phenyl-5-(2-phenyl-1H-imidazol-5-yl)pyridine

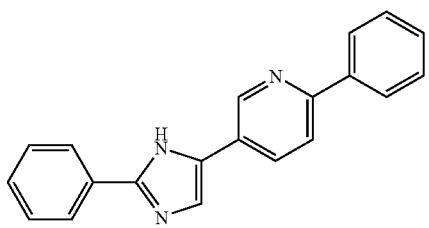

The title compound was prepared by the method described in Example 1, except that commercially available 2-iodo-5- bromopyridine was used instead of 2-iodo-5-bromopyrimidine in Step A; $R_f$ 0.53 with 95:5 v/v dichloromethane-methanol; melting point 206° C.; $^1$H-NMR (400 MHz; DMSO-$d_6$) δ 9.15 (s, 2H), 8.26 (dd, 2H), 8.14-7.94 (m, 5H), 7.52-7.34 (m, 5H); MS (ESI$^+$) m/z 298.1 (M+1); H-PGDS FPBA IC$_{50}$: 0.48 μM; H-PGDS inhibitor EIA IC$_{50}$: 0.097 μM.

Example 3

Preparation of 5-(1-methyl-2-phenyl-1H-imidazol-5-yl)-2-phenylpyrimidine

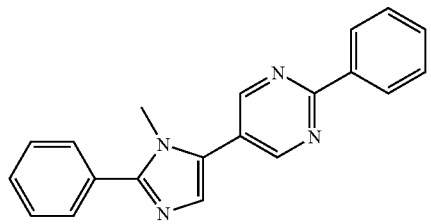 [SMILES: Cn1c(-c2cnc(-c3ccccc3)nc2)cnc1-c1ccccc1]

The title compound was prepared by the method described in Example 1, Steps A-C, except that iodomethane was used instead of benzyl bromide in Step B; $R_f$ 0.36 with 1:1 v/v ethyl acetate-hexane; melting point 211° C.; $^1$H-NMR (400 MHz; DMSO-$d_6$) δ 9.17 (s, 2H), 8.41 (m, 2H), 7.75 (dd, 2H), 7.6-7.27 (m, 7H); MS (ESI$^+$) m/z 313.2 (M+1); H-PGDS FPBA IC$_{50}$: 0.625 μM; H-PGDS inhibitor EIA IC$_{50}$: 0.25 μM.

Example 4

Preparation of 5-(4-methyl-2-phenyl-1H-imidazol-5-yl)-2-phenylpyrimidine

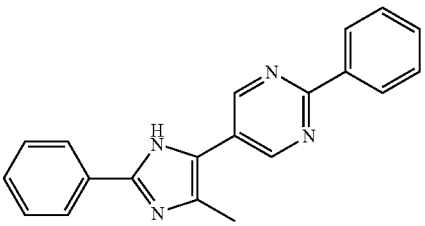 [SMILES: Cc1nc(-c2ccccc2)[nH]c1-c1cnc(-c2ccccc2)nc1]

The title compound was prepared by the method described in Example 1, except that commercially available 4-methyl-2-phenyl-1H-imidazole (TCI America) was used instead of 2-phenylimidazole in Step B; $R_f$ 0.73 with 95:5 v/v dichloromethane-methanol; melting point 138° C.; $^1$H-NMR (400 MHz; DMSO-$d_6$) δ 9.28 (s, 2H), 8.52-8.46 (m, 2H), 8.05 (d, 2H), 7.64-7.52 (m, 5H), 7.44 (m, 1H), 2.64 (s, 3H); MS (ESI$^+$) m/z 313.0 (M+1); H-PGDS FPBA IC$_{50}$: 0.45 μM; H-PGDS inhibitor EIA IC$_{50}$: 0.082 μM.

| Ex. | R$^2$ | R$^1$ | H-PGDS FPBA IC$_{50}$ (μM) | H-PGDS Inhibitor EIA IC$_{50}$ (μM) |
|---|---|---|---|---|
| 5 | H | Ph | 5 | |
| 6 | Ph | 3-F-Ph | 0.28 | 0.047 |
| 7 | Ph | 3,4-diOMe-Ph | 3.5 | |
| 8 | 3-F-Ph | Ph | 0.188 | 0.004 |
| 9 | 2-pyridyl | Ph | 0.125 | 0.053 |
| 10 | 3-pyridyl | Ph | 0.079 | 0.021 |
| 11 | 3-pyridyl | 3-F-Ph | 0.156 | 0.041 |
| 12 | 3-pyridyl | 3-pyridyl | 1.3 | |
| 13 | 4-pyridyl | Ph | 0.125 | 0.075 |
| 14 | Bn | Ph | 0.625 | 0.059 |
| 15 | (3-pyridyl-CH=CH-) | Ph | 0.15 | 0.023 |
| 16 | (3-pyridyl-CH$_2$CH$_2$-) | Ph | 0.3 | |
| 17 | (N-Boc-piperidin-4-yl) | Ph | 0.15 | |

-continued

| Ex. | R² | R¹ | H-PGDS FPBA IC₅₀ (μM) | H-PGDS Inhibitor EIA IC₅₀ (μM) |
|---|---|---|---|---|
| 18 | 4-piperidinyl (HN-) | Ph | 1.0 | |
| 19 | 1-benzylpiperidin-4-yl | Ph | 0.08 | 0.006 |
| 20 | 1-(pyridine-3-carbonyl)piperidin-4-yl | Ph | 0.45 | |
| 21 | 1-Boc-piperidin-3-yl | Ph | 0.20 | |
| 22 | piperidin-3-yl (HN-) | Ph | 1.25 | |
| 23 | 1-benzylpiperidin-3-yl | Ph | 0.6 | |
| 24 | 1-(2,2,2-trifluoro-1-hydroxyethyl)piperidin-3-yl | Ph | 10 | |
| 25 | 1-(methylcarbamoyl)piperidin-3-yl | Ph | 0.3 | |

-continued
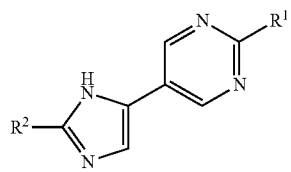
| Ex. | R² | R¹ | H-PGDS FPBA IC$_{50}$ (μM) | H-PGDS Inhibitor EIA IC$_{50}$ (μM) |
|---|---|---|---|---|
| 26 | 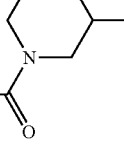 | Ph | | |
| 27 | 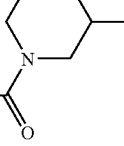 | Ph | 0.09 | |
| 28 | 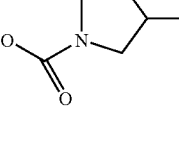 | Ph | 0.15 | |
| 29 | 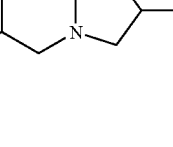 | Ph | | |
| 30 |  | Ph | 2 | |
| 31 | 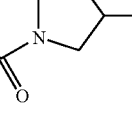 | Ph | | |

Example 5

Preparation of 5-(1H-imidazol-5-yl)-2-phenylpyrimidine

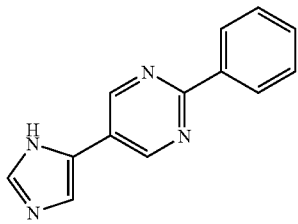 [SMILES: c1ccc(-c2ncc(-c3cnc[nH]3)cn2)cc1]

The title compound was prepared by the method described in Example 1, except that imidazole (Aldrich) was used instead of 2-phenylimidazole in Step B; $R_f$ 0.13 with 95:5 v/v dichloromethane-methanol; melting point 216° C.; $^1$H-NMR (400 MHz; DMSO-$d_6$) δ 9.32 (s, 2H), 8.50-8.43 (m, 2H), 7.99 (s, 1H), 7.91 (s, 1H), 7.62-7.55 (m, 3H); MS (ESI$^+$) m/z 223.0 (M+1); H-PGDS FPBA IC$_{50}$: 5 μM.

Example 6

Preparation of 2-(3-fluorophenyl)-5-(2-phenyl-1H-imidazol-5-yl)pyrimidine

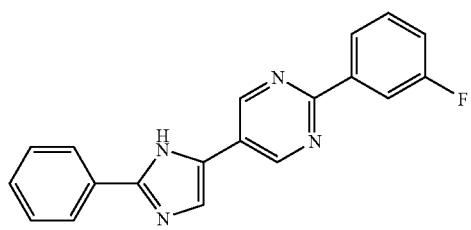 [SMILES: Fc1cccc(-c2ncc(-c3cnc(-c4ccccc4)[nH]3)cn2)c1]

The title compound was prepared by the method described in Example 1, except that commercially available 3-flourobenzene boronic acid was used instead of benzeneboronic acid in Step A; $R_f$ 0.61 with 95:5 v/v dichloromethane-methanol; melting point 240° C; $^1$H-NMR (400 MHz; CDCl$_3$) δ 8.97 (s, 2H), 7.99 (d, 1H), 7.90-7.85 (m, 1H), 7.80-7.75 (m, 2H), 7.31 (s, 1H), 7.22-7.07 (m, 4H), 6.89 (dt, 1H); MS (ESI$^+$) m/z 317.1 (M+1); H-PGDS FPBA IC$_{50}$: 0.28 μM; H-PGDS inhibitor EIA IC$_{50}$: 0.047 μM.

Example 7

Preparation of 2-(3,4-dimethoxyphenyl)-5-(2-phenyl-1H-imidazol-5-yl)pyrimidine

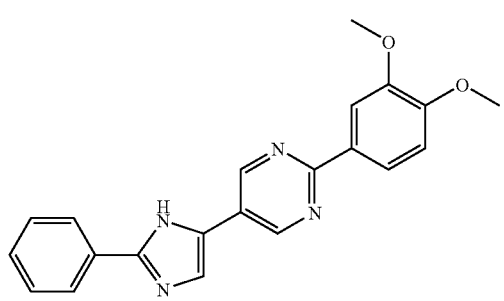 [SMILES: COc1ccc(-c2ncc(-c3cnc(-c4ccccc4)[nH]3)cn2)cc1OC]

The title compound was prepared by the method described in Example 1, except that commercially available 3,4-dimethoxybenzene boronic acid was used instead of benzeneboronic acid in Step A; $R_f$ 0.45 with 95:5 v/v dichloromethane-methanol; melting point 231° C.; $^1$H-NMR (400 MHz; DMSO-$d_6$) δ 9.23 (s, 2H), 8.06-7.94 (m, 5H), 7.48 (m, 2H), 7.38 (m, 1H), 7.08 (d, 1H), 3.84 (s, 3H), 3.82 (s, 3H); MS (ESI$^+$) m/z 359.1 (M+1); H-PGDS FPBA IC$_{50}$: 3.5 μM.

Example 8

Preparation of 5-(2-(3-fluorophenyl)-1H-imidazol-5-yl)-2-phenylpyrimidine

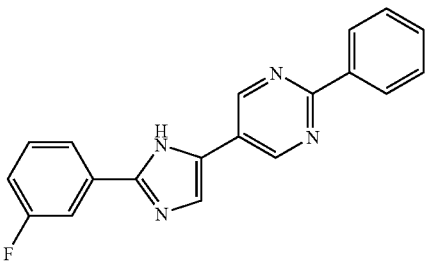

Step A: Preparation of 2-(3-fluorophenyl)-1H-imidazole

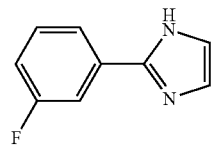

In a flask containing 3-flourobenzonitrile (Matrix Scientific, 3.0 g, 25 mmol) was added methanol (30 mL) and sodium methoxide (Aldrich, 25% by wt. in methanol, 2.83 mL, 12.4 mmol). The reaction mixture was stirred for 1.5 hours and aminoacetaldehyde dimethyl acetal (Alfa Aesar, 2.60 g, 24.8 mmol) and acetic acid (2.83 mL, 49.5 mmol) were subsequently added and the solution was heated at reflux for one hour. After cooling to room temperature, methanol (25 mL) and 6 N HCl (8 mL) was added and the solution was heated at reflux for 16 hours. After cooling the solution to room temperature the residue was taken up in a 1:1 mixture (v/v) of water and ethyl acetate (50 mL). The aqueous layer was separated and the pH of this solution was adjusted to pH 9 with 2 N NaOH, upon which a white precipitate formed in solution. The solid was collected by filtration and dried under high vacuum to provide 2-(3-fluorophenyl)-1H-imidazole as an off-white solid (1.67 g, 41% yield, MS (ESI$^+$) m/z 163.1 (M+1).

Step B: Preparation of 1-benzyl-2-(3-fluorophenyl)-1H-imidazole

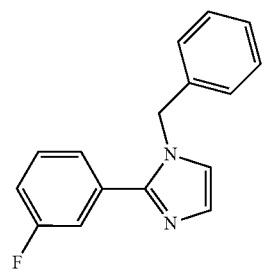 [SMILES: Fc1cccc(-c2nccn2Cc2ccccc2)c1]

To a mixture consisting of 2-(3-fluorophenyl)-1H-imidazole (0.80 g, 4.9 mmol) and N,N-dimethylformamide (10 mL) was added 60% sodium hydride in mineral oil (0.22 g, 5.4 mmol). After stirring for one hour at room temperature, a solution consisting of benzyl bromide (Aldrich, 0.65 mL, 5.4 mmol) in N,N-dimethylformamide (5 mL) was added dropwise while stirring. After stirring at room temperatures for 12 hours the reaction was complete as observed by TLC. The reaction mixture was partitioned between ethyl acetate (150 mL) and water (100 mL). The phases were separated and the organic layer was washed with brine (100 mL), and was subsequently dried over anhydrous magnesium sulfate. Concentration under reduced pressure afforded the crude product as a yellow oil. The product was purified by flash silica column chromatography. Elution through a 40-g Silicycle® flash silica cartridge with gradient of 10% to 30% ethyl acetate in hexane, and subsequently 5% methanol in dichloromethane afforded the title intermediate as a colorless oil (0.408 g, 32% yield); $R_f$ 0.45 with 95:5 v/v dichloromethane-methanol; (ESI$^+$) m/z 253.1 (M+1).

Step C: Preparation of 5-(2-(3-fluorophenyl)-1H-imidazol-5-yl)-2-phenylpyrimidine

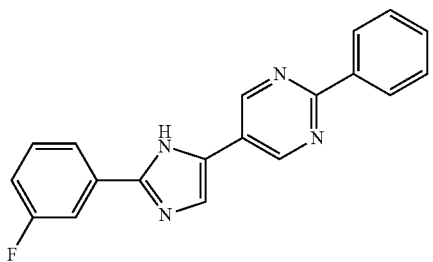 [SMILES: Fc1cccc(-c2ncc(-c3cnc(-c4ccccc4)nc3)[nH]2)c1]

The title compound was prepared by the method described in Example 1, except that 1-benzyl-2-(3-fluorophenyl)-1H-imidazole was used instead of 1-benzyl-2-phenyl-1H-imidazole in Step C; $R_f$ 0.55 with 95:5 v/v dichloromethane-methanol; melting point 221° C.; $^1$H-NMR (400 MHz; DMSO-d$_6$) δ 9.31 (s, 2H), 8.44-8.37 (m, 2H), 8.14-8.06 (m, 1H), 7.88-7.77 (m, 2H), 7.58-7.48 (m, 4H), 7.23 (dt, 1H); MS (ESI$^+$) m/z 317.1 (M+1); H-PGDS FPBA IC$_{50}$: 0.188 µM; H-PGDS inhibitor EIA IC$_{50}$: 0.004 µM.

Example 9

Preparation of 2-phenyl-5-(2-(pyridin-2-yl)-1H-imidazol-5-yl)pyrimidine

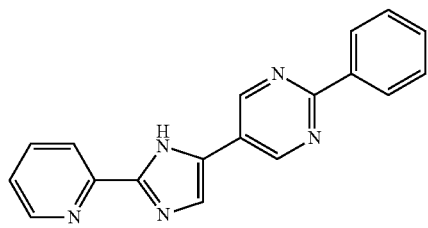 [SMILES: c1ccc(-c2ncc(-c3cnc(-c4ccccn4)[nH]3)cn2)cc1]

The title compound was prepared by the method described in Example 1, except that 2-(1-benzyl-1H-imidazol-2-yl)pyridine (prepared according to Example 8, Step A, except that commercially available 2-cyanopyridine was used instead of 3-fluorobenzonitrile) was used instead of 1-benzyl-2-phenyl-1H-imidazole in Step C; $R_f$ 0.43 with 95:5 v/v dichloromethane-methanol; melting point 262° C.; $^1$H-NMR (400 MHz; DMSO-d$_6$) δ 9.33 (s, 2H), 8.63 (d, 1H), 8.43-8.37 (m, 2H), 8.16 (d, 1H), 8.06 (d, 1H), 7.94 (dt, 1H), 7.54-7.49 (m, 3H), 7.43-7.39 (m, 1H); MS (ESI$^+$) m/z 300.1 (M+1); H-PGDS FPBA IC$_{50}$: 0.125 µM; H-PGDS inhibitor EIA IC$_{50}$: 0.053 µM.

Example 10

Preparation of 2-phenyl-5-(2-(pyridin-3-yl)-1H-imidazol-5-yl)pyrimidine

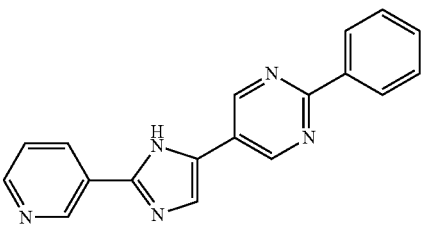 [SMILES: c1ccc(-c2ncc(-c3cnc(-c4cccnc4)[nH]3)cn2)cc1]

The title compound was prepared by the method described in Example 1, except that 3-(1-benzyl-1H-imidazol-2-yl)pyridine was used instead of 1-benzyl-2-phenyl-1H-imidazole in Step C. 3-(1-Benzyl-1H-imidazol-2-yl)pyridine was prepared by the method described in Example 8, Steps A and B except the commercially available 3-cyanopyridine was used instead of 3-fluorobenzonitrile; $R_f$ 0.25 with 95:5 v/v dichloromethane-methanol; melting point 308° C; $^1$H-NMR (400 MHz; DMSO-d$_6$) δ 9.32 (s, 2H), 9.20 (d, 1H), 8.58 (dd, 1H), 8.44-8.31 (m, 3H), 8.12 (m, 1H), 7.57-7.46 (m, 4H); MS (ESI$^+$) m/z 300.1 (M+1); H-PGDS FPBA IC$_{50}$: 0.079 µM; H-PGDS inhibitor EIA IC$_{50}$: 0.021 µM.

Example 11

Preparation of 2-(3-fluorophenyl)-5-(2-(pyridin-3-yl)-1H-imidazol-5-yl)pyrimidine

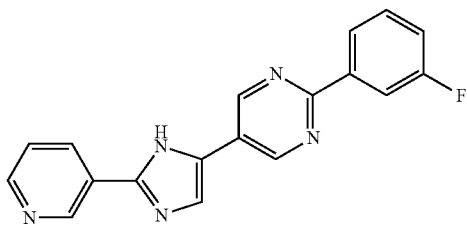 [SMILES: Fc1cccc(-c2ncc(-c3cnc(-c4cccnc4)[nH]3)cn2)c1]

The title compound was prepared by the method described in Example 1, except that (i) commercially available 3-flourobenzene boronic acid was used instead of benzeneboronic acid in Step A, and (ii) 3-(1-benzyl-1H-imidazol-2-yl)pyridine (prepared according to the method described in Example 8, Step A, except that commercially available 3-cyanopyridine was used instead of 3-fluorobenzonitrile) was used in place of the 1-benzyl-2-phenyl-1H-imidazole in Step C; $R_f$ 0.35 with 95:5 v/v dichloromethane-methanol; melting point 309° C; $^1$H-NMR (400 MHz; DMSO-d$_6$) δ 9.40 (s, 2H), 9.27 (d,1H), 8.64 (dd, 1H), 8.40 (dt, 1H), 8.31 (dd, 1H), 8.23 (bs, 1H), 8.18-8.13 (m, 1H), 7.66-7.55 (m, 3H), 7.42 (dt, 1H); MS (ESI+) m/z 318.0 (M+1); H-PGDS FPBA IC$_{50}$: 0.156 µM; H-PGDS inhibitor EIA IC$_{50}$: 0.041 µM.

Example 12

Preparation of 2-(pyridin-3-yl)-5-(2-(pyridin-3-yl)-1H-imidazol-5-yl)pyrimidine

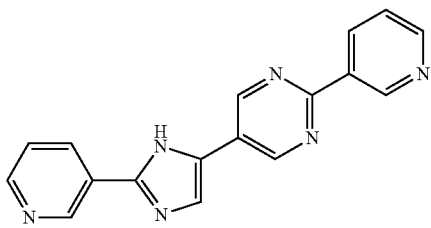 [SMILES: c1cncc(-c2ncc(-c3cnc(-c4cccnc4)[nH]3)cn2)c1]

The title compound was prepared by the method described in Example 1, except that (i) commercially available 3-pyridyl boronic acid was used instead of benzene boronic acid in Step A, and (ii) 3-(1-benzyl-1H-imidazol-2-yl)pyridine was used instead of 1-benzyl-2-phenyl-1H-imidazole in Step C. 3-(1-Benzyl-1H-imidazol-2-yl)pyridine was prepared by the method described in Example 8, Steps A and B except the commercially available 3-cyanopyridine was used instead of 3-fluorobenzonitrile; R$_f$ 0.35 with 92.5:7.5 v/v dichloromethane-methanol; melting point 299° C.; $^1$H-NMR (400 MHz; DMSO-d$_6$) δ 9.52 (s, 1H), 9.35 (s, 2H), 9.21 (s, 1H), 8.72-8.65 (m, 2H), 8.60-8.56 (m, 1H), 8.37-8.32 (m, 1H), 8.15 (s, 1H), 7.58-7.50 (m, 2H); LC/MS (ESI+) m/z 301.1 (M+1); H-PGDS FPBA IC$_{50}$: 1.3 µM.

Example 13

Preparation of 2-phenyl-5-(2-(pyridin-4-yl)-1H-imidazol-5-yl)pyrimidine

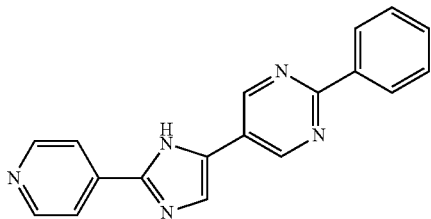 [SMILES: c1ccc(-c2ncc(-c3cnc(-c4ccncc4)[nH]3)cn2)cc1]

The title compound was prepared by the method described in Example 1, except that 4-(1-benzyl-1H-imidazol-2-yl)pyridine (prepared according to Example 8, Step A, except that commercially available 4-cyanopyridine was used instead of 3-fluorobenzonitrile) was used in place of the 1-benzyl-2-phenyl-1H-imidazole in Step C; R$_f$ 0.26 with 95:5 v/v dichloromethane-methanol; melting point 300° C.; $^1$H-NMR (400 MHz; DMSO-d$_6$) δ 9.40 (s, 2H), 8.73 (d, 2H), 8.50-8.45 (m, 2H), 8.25 (bs, 1H), 8.00 (d, 2H), 7.62-7.55 (m, 4H); MS (ESI+) m/z 300.0 (M+1); H-PGDS FPBA IC$_{50}$: 0.125 µM; H-PGDS inhibitor EIA IC$_{50}$: 0.075 µM.

Imidazole compounds of the exemplary embodiments may also be prepared using the general alternative synthetic route illustrated in Scheme 3. Examples 14-31 are imidazole compounds of the exemplary embodiments that were prepared at least in part according to the route illustrated in Scheme 3. Bromopyridines and bromopyrimidines of general structure 3 may be heated with tributyl(1-ethoxyvinyl)stannane in the presence of a palladium catalyst, such as palladium(II) acetate and a ligand, such as triphenylphosphine, in an organic solvent, such as 1,4-dioxane, to form the corresponding ketones of general structure 11, as shown in Scheme 3. Bromination of ketone 11 with a bromination reagent such as tetrabutylammonium tribromide provides the corresponding α-bromoketone of general structure 12. Reaction of an α-bromoketone 12 with a carboxylic acid bearing a desired R$^2$ group or R$^2$ group precursor in the presence of a base, such as cesium carbonate in a solvent, such as tetrahydrofuran (THF) or N,N-dimethylformamide (DMF), provides the corresponding ester-ketone intermediate with the general structure 13. Reaction of an ester-ketone 13 with ammonium acetate in a solvent, such as toluene, with heating, affords the corresponding imidazole compound of general structure 14.

Scheme 3: Alternative general synthesis of 5-(imidazol-4-yl)-pyridines and 5-(imidazol-4-yl)-pyrimidines

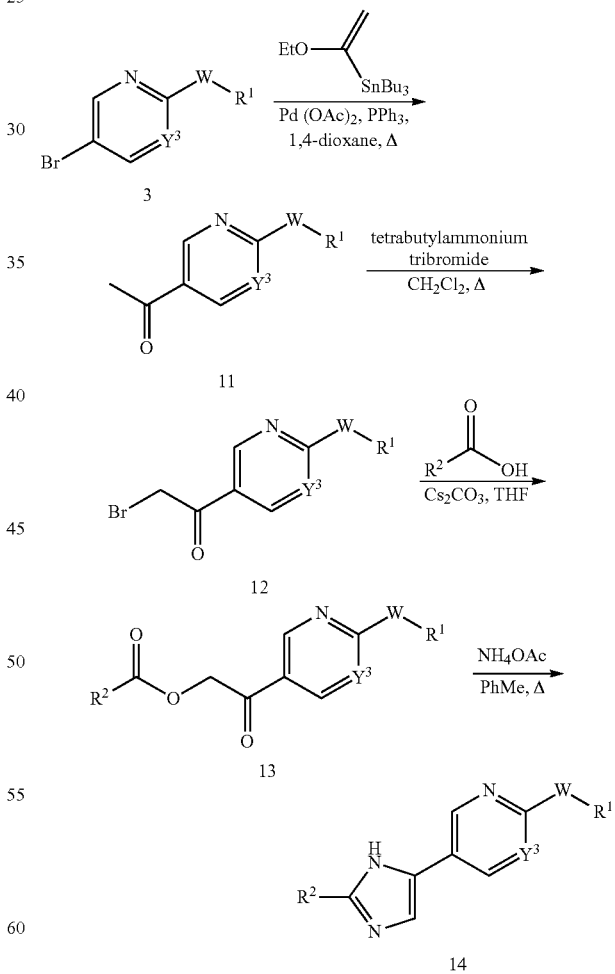

An alternative method, described in Scheme 4, may also be used to prepare ketone intermediates with the general structure 11. Aspects of this methodology may be found in patent application publication WO 2009/080523 (Scheme 2, Steps I and J) and in Han, Ki-Jong; Kim, Misoo; *Letters in Organic Chemistry*, 2007, 4(1), 20-22. Starting from a prepared or commercially available carboxylic acid 15, reaction with triphosgene in the presence of excess amine base forms an activated carbonyl intermediate, which is subsequently reacted with N,O-dimtheylhydroxylamine hydrochloride to provide the Weinreb amide intermediate 16. Reaction of the Weinreb amide with methylmagnesium chloride in THF provides the corresponding acetophenone 11 with good overall yield. Other methods for preparing ketones of this general type are known to those ordinarily skilled in the art.

Scheme 4: General Weinreb amide route to prepare intermediate 11

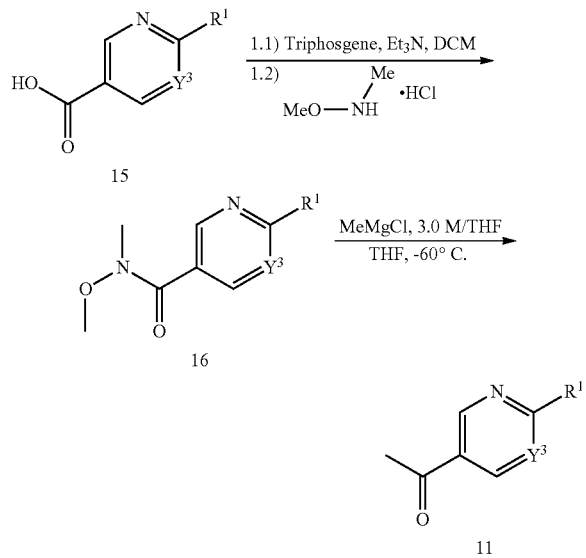

Example 14

Preparation of 5-(2-benzyl-1H-imidazol-5-yl)-2-phenylpyrimidine

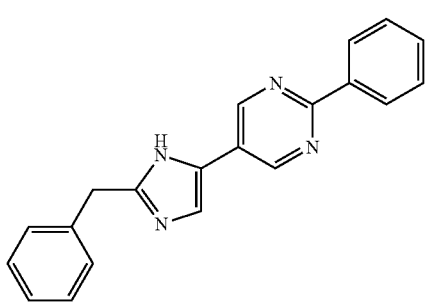 [SMILES: c1ccc(Cc2ncc(-c3cnc(-c4ccccc4)nc3)[nH]2)cc1]

Step A: Preparation of 1-(2-phenylpyrimidin-5-yl)ethanone

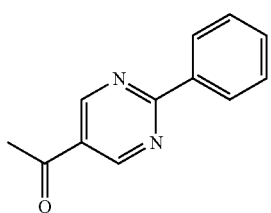

A stirring mixture consisting of palladium(II) acetate (215 mg, 0.32 mmol) and triphenylphosphine (335 mg, 1.28 mmol) in 1,4-dioxane (25 mL) was heated at 80° C. for 30 minutes. The dark reaction mixture was cooled to room temperature, and to this reaction mixture was added a solution consisting of 5-bromo-2-phenylpyrimidine (Example 1A, 3.0 g, 13 mmol) and tributyl(1-ethoxyvinyl)tin (4.74 mL, 14.0 mmol) in 1,4-dioxane (63 mL). The reaction mixture was stirred and heated at 75° C. overnight and was subsequently cooled to room temperature. The reaction progress was monitored by thin layer chromatography (95:5 v/v hexanes-ethyl acetate) until completion. The reaction mixture was treated with 1 N hydrochloric acid (19 mL) for one hour at room temperature and poured into a saturated aqueous sodium bicarbonate solution. The organic material was extracted two times with a mixture of ethyl acetate and hexanes, and the combined organic phase was washed sequentially with water and brine, and was dried over anhydrous magnesium sulfate, filtered through a well packed pad of magnesium sulfate, and concentrated under reduced pressure. The residue was dissolved in dichloromethane (30 mL) and diluted with hexanes (30 mL). The resulting precipitate was filtered to give the title intermediate (872 mg). The filtrate was applied to a 80-g silica column eluted with 1:1:9 v/v/v ethyl acetate-dichloromethane-hexanes to afford 1.01 g of additional title intermediate (1.88 g total, 74%); $R_f$ 0.23 with 9:1 v/v hexanes-ethyl acetate solvent system; $^1$H-NMR (400 MHz; DMSO-$d_6$) δ 9.4 (s, 2H), 8.45-8.50 (m, 2H), 7.5-7.7 (m, 3H), 2.68 (s, 3H); MS (ESI$^+$) m/z 199 (M+1).

Alternative preparation of 1-(2-phenylpyrimidin-5-yl)ethanone

Step i: Preparation of N-methoxy-N-methyl-2-phenylpyrimidine-5-carboxamide

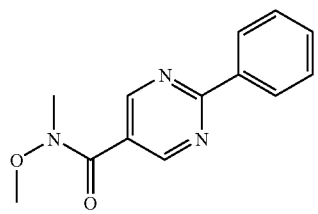

To an ice-cooled solution (0° C.) consisting of 2-phenylpyrimidine-5-carboxylic acid (prepared according to WO 2007/041634 A1 Example 1, 2.10 g, 10.5 mmol) in dichloromethane (40 mL) was added triphosgene (1.55 g, 5.25 mmol) and triethylamine (7.3 mL, 52.45 mmol). Upon addition of triethylamine a yellow precipitate formed in solution. After stirring for five minutes in the ice bath, N,O-dimtheylhydroxylamine hydrochloride (1.02 g, 10.5 mmol) was added and the solution was allowed to slowly warm to room temperature over 30 minutes. The reaction was complete after stirring for three hours at room temperature. The crude solution was filtered and washed with excess dichloromethane. The filtrate was concentrated under reduced pressure to afford an orange solid. The crude product was purified by flash silica column chromatography. Elution through a 40-g Silicylce® flash silica cartridge with 10-30% ethyl acetate in hexanes afforded the title intermediate as a colorless oil (1.85 g, 72% yield); $R_f$ 0.48 with 1:1 v/v hexanes-ethyl acetate; $^1$H-NMR (400 MHz; CDCl$_3$) δ 9.20 (s, 2H), 8.50 (dd, 2H), 7.55 (m, 3H), 3.62 (s, 3H), 3.42 (s, 3H); MS (APCI$^+$) m/z 244.0 (M+1).

Step ii: Preparation of 1-(2-phenylpyrimidin-5-yl)ethanone

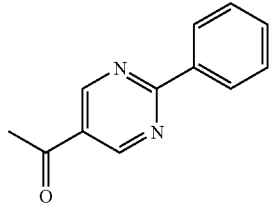

A solution consisting of N-methoxy-N-methyl-2-phenylpyrimidine-5-carboxamide (Step I, 1.80 g, 7.39 mmol) in anhydrous THF (20 mL) was cooled in a −60° C. bath (ethanol, CO$_2$(s)). Methylmagnesium chloride (Aldrich, 3.0 M in THF, 2.75 mL, 8.14 mmol) was subsequently added dropwise to the reaction mixture. The reaction mixture was stirred for 30 minutes in the −60° C. bath and was subsequently allowed to warm to room temperature over one hour. The crude reaction mixture was then poured into a separatory funnel that contained diethyl ether (200 mL) and saturated ammonium chloride (150 mL). The organic layer was separated and the aqueous layer was washed again with diethyl ether (100 mL). The combined organic layer was dried over anhydrous sodium sulfate, filtered, and concentrated under reduced pressure to afford a white solid as the crude product. The crude solid was triturated with a hexane-ethyl acetate (9:1 v/v) mixture (20 mL). The precipitate in solution was filtered to afford the title compound as a white solid (1.15 g, 78% yield); R$_f$ 0.72 with 1:1 v/v hexanes-ethyl acetate; $^1$H-NMR (400 MHz; CDCl$_3$) δ 9.25 (s, 2H), 8.53 (dd, 2H), 7.58 (m, 3H), 2.63 (s, 3H); MS (APCI$^+$) m/z 199.0 (M+1).

Step B: Preparation of 2-bromo-1-(2-phenylpyrimidin-5-yl)ethanone

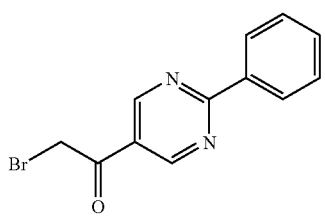 [SMILES: O=C(CBr)c1cnc(-c2ccccc2)nc1]

To a solution consisting of 1-(2-phenylpyrimidin-5-yl)ethanone (Step A, 700 mg, 3.5 mmol) in dichloromethane (25 mL) was added tetrabutylammonium tribromide (1.87 g, 3.90 mmol). The reaction mixture was sealed with a screw top and warmed at 40° C. for 5 hours and allowed to cool to room temperature over a weekend. The pale yellow precipitate formed was collected on a filter and washed with 1:1 dichloromethane-hexane to afford the title intermediate (770 mg, 79%); R$_f$ 0.31 with 9:1 v/v hexanes-ethyl acetate; MS (ESI$^+$) m/z 279, 277 (M+1, Br isotopes).

Step C: Preparation of 5-(2-benzyl-1H-imidazol-5-yl)-2-phenylpyrimidine

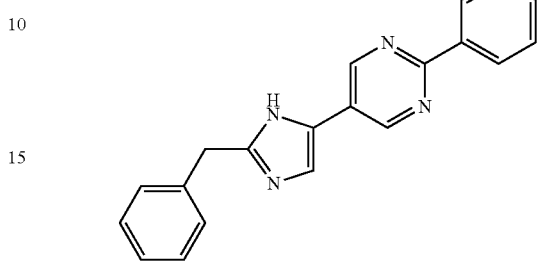

To a solution consisting of phenylacetic acid (27 mg, 0.20 mmol) and cesium carbonate (117 mg, 0.360 mmol) in tetrahydrofuran (1.5 mL) at room temperature was added 2-bromo-1-(2-phenylpyrimidin-5-yl)ethanone (Step B, 50 mg, 0.18 mmol). The reaction mixture was heated at 40° C. for one hour and cooled to room temperature. To the mixture was added water (10 mL) with vigorous stirring and the precipitate was filtered, washed with water, and dried on the suction filter to provide 2-oxo-2-(2-phenylpyrimidin-5-yl) ethyl 2-phenylacetate as a tan solid (34.5 mg, 57% yield) as an isolated intermediate. The tan solid was dissolved in toluene (4 mL) and freshly prepared ammonium acetate under toluene (300 mg wet with toluene) was added and the mixture was stirred vigorously and heated in a capped vial at 112° C. overnight. The brown reaction mixture was poured into aqueous sodium bicarbonate and extracted twice with ethyl acetate. The combined organic phase was dried over anhydrous magnesium sulfate, filtered, and concentrated under reduced pressure to dryness. The brown solid was dissolved in dichloromethane and chromatographed on a 4 g silica column eluted with 1:4:5 to 1:6:3 dichloromethane-ethyl acetate-hexane to afford the title compound as a tan solid; R$_f$ 0.08 with 6:4 v/v hexanes-ethyl acetate and R$_f$ 0.61 with 3:7 v/v hexanes-ethyl acetate; melting point 235° C.; $^1$H-NMR (400 MHz; DMSO-d$_6$) δ 9.21 (s, 2H), 8.3-8.5 (m, 2H), 7.82 (d, 1H), 7.5-7.6 (m, 3H), 7.2-7.4 (m, 5H), 4.08 (s, 2H); MS (ESI$^+$) m/z 313 (M+1); H-PGDS FPBA IC$_{50}$: 0.625 µM; H-PGDS inhibitor EIA IC$_{50}$: 0.059 µM.

Example 15

Preparation of (E)-2-phenyl-5-(2-(2-(pyridin-3-yl) vinyl)-1H-imidazol-5-yl)pyrimidine

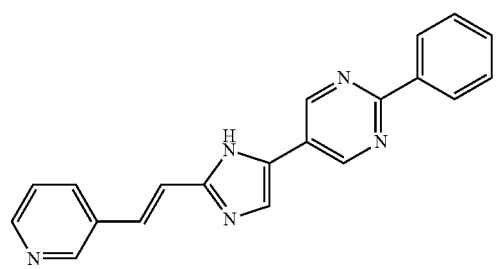 [SMILES: C(=C\c1ncc(-c2cnc(-c3ccccc3)nc2)[nH]1)/c1cccnc1]

To a solution consisting of trans-3-(3-pyridyl)acrylic acid (30 mg, 0.20 mmol) and cesium carbonate (117 mg, 0.360 mmol) in tetrahydrofuran (1.5 mL) was added 2-bromo-1-(2-phenylpyrimidin-5-yl)ethanone (Example 14, Step B, 50 mg, 0.18 mmol). The reaction mixture was warmed at 40° C. for 1.5 hours, cooled to room temperature, and stirred vigorously while water (15 mL) was added quickly. The precipitate was filtered, washed with water, and dried in high vacuum to give crude material (32.5 mg) that was dissolved in of toluene (4 mL). To this solution was added freshly prepared ammonium acetate under toluene (400 mg wet with toluene and acetic acid). The reaction mixture was heated at 112° C. overnight and subsequently cooled to room temperature. The brown precipitate was filtered and the mother liquor was concentrated under reduced pressure and chromatographed on silica (4 g) eluted with ethyl acetate. The product was purified by crystallization from methanol and water to afford the title compound (5.4 mg, 18% yield) as a tan crystalline-like solid; $R_f$ 0.35 with 3:97 v/v ethanol-ethyl acetate; melting point 258° C.; $^1$H-NMR (400 MHz; DMSO-$d_6$) δ 9.29 (s, 2H), 8.78 (d, 1H), 8.45-8.55 (m, 1H), 8.40-8.45 (m, 2H), 8.07-8.12 (m, 1H), 8.03-8.07 (m, 1H), 7.5-7.6 (m, 3H), 7.38-7.44 (m, 2H), 7.29 (d, 1H); MS (ESI$^+$) m/z 326 (M+1); H-PGDS FPBA IC$_{50}$: 0.15 μM; H-PGDS inhibitor EIA IC$_{50}$: 0.023 μM.

Example 16

Preparation of 2-phenyl-5-(2-(2-(pyridin-3-yl)ethyl)-1H-imidazol-5-yl)pyrimidine

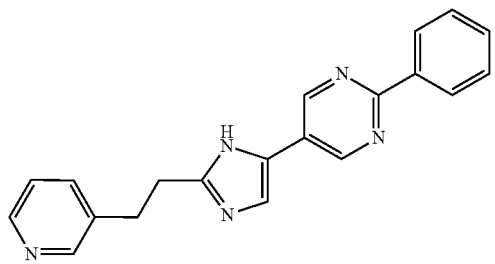 [SMILES: c1ccc(-c2ncc(-c3cnc(CCc4cccnc4)[nH]3)cn2)cc1]

The title compound was prepared by subjecting (E)-2-phenyl-5-(2-(2-(pyridin-3-yl)vinyl)-1H-imidazol-5-yl)pyrimidine (Example 15, 7 mg, 0.02 mmol) to hydrogenation using 10% palladium on carbon (dry, 1 mg) in ethanol (3 mL). After five days, the reaction mixture was filtered through Celite using ethanol to rinse. Evaporation provided the title compound as a brown solid (7 mg, quantitative yield); melting point 113° C.; $^1$H-NMR (400 MHz; CD$_3$OD) δ 9.16 (s, 2H), 8.39-8.44 (m, 4H), 7.64 (s, 1H), 7.52-7.53 (m, 5H)), 3.12-3.19 (m, 4H); LC/MS (ESI$^+$) m/z 328; H-PGDS FPBA IC$_{50}$: 0.3 μM.

Piperidine-, pyrrolidine-, and azetidine-containing compounds of the exemplary embodiments (20a-c) may be prepared according to the general synthetic route illustrated in Scheme 3, wherein R$^2$ is a carbon-bound piperidinyl, pyrrolidinyl, or azetidinyl group as shown in Scheme 5. An α-bromoketone intermediate 12 is reacted with a regioisomer of N-Boc-piperidine-carboxylic acid 17a, N-Boc-pyrrolidine-carboxylic acid 17b, or with N-Boc-azetidin-3-carboxylic acid 17c in the presence of a base, such as cesium carbonate, in a solvent, such as DMF to provide the corresponding ester-ketone intermediates 18a-c. Each intermediate 18a-c may be converted to its corresponding imidazole 19a-c in the presence of ammonium acetate in a solvent, such as toluene, with heating. Removal of the Boc group takes place in the presence of trifluoroacetic acid to afford amine compounds of general structure 20a-c. Examples 17-19, 21-22, 28, and 30 may be prepared according to this general route.

Scheme 5: General preparation of piperidine-, pyrrolidine-, and azetidine-imidazole-pyr(im)idines

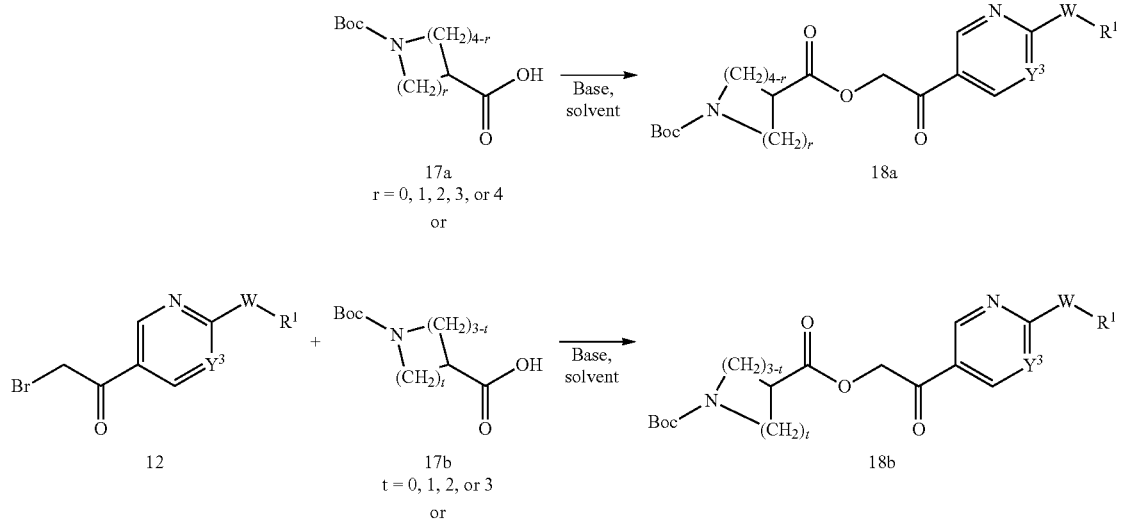

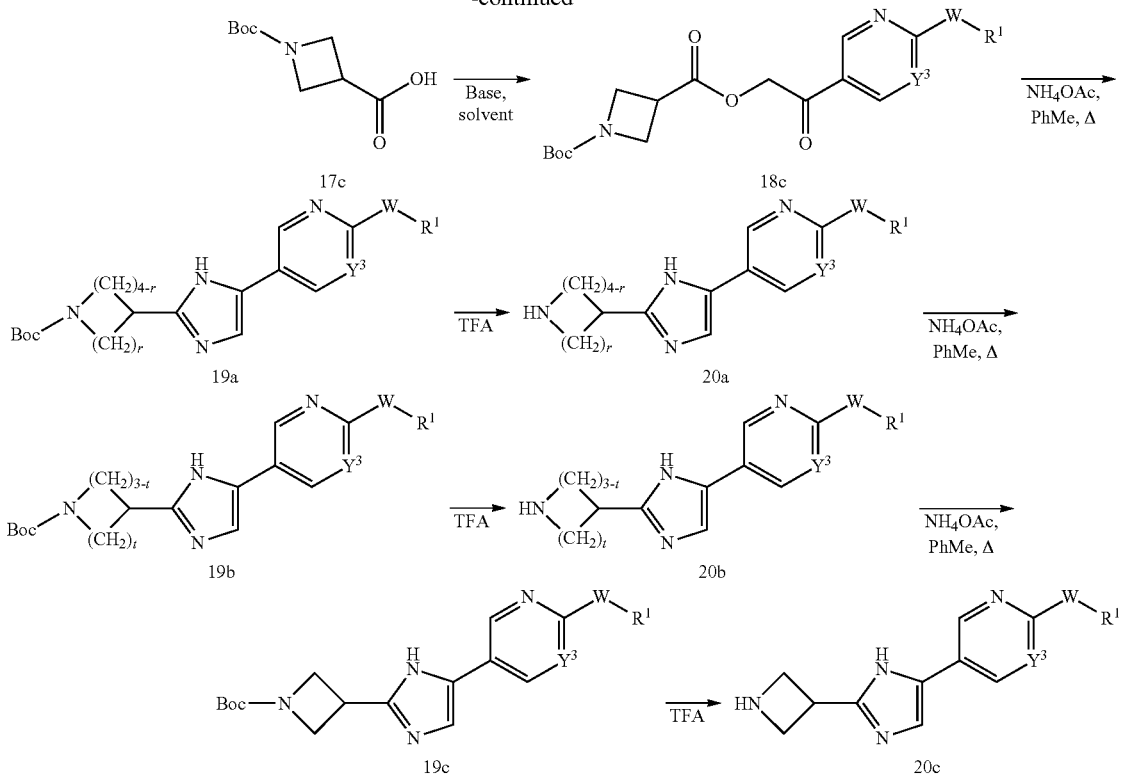

Example 17

Preparation of tert-butyl 4-(5-(2-phenylpyrimidin-5-yl)-1H-imidazol-2-yl)piperidine-1-carboxylate

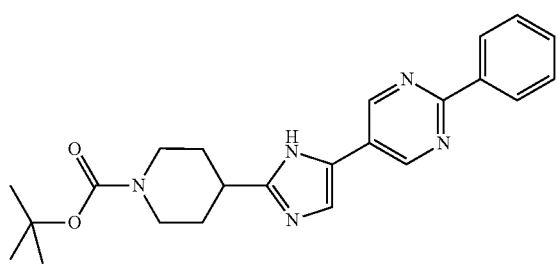 [SMILES: CC(C)(C)OC(=O)N1CCC(c2ncc(-c3cnc(-c4ccccc4)nc3)[nH]2)CC1]

To a solution consisting of 1-(tert-butoxycarbonyl)piperidine-4-carboxylic acid (170 mg, 0.74 mmol) in dimethylformamide (7 mL) was added cesium carbonate (459 mg, 1.44 mmol) and the reaction mixture was stirred for 15 minutes. To the reaction mixture was added 2-bromo-1-(2-phenylpyrimidin-5-yl)ethanone (Example 14, Step B, 200 mg, 0.72 mmol) and the mixture was stirred for two hours. Water was added to the reaction mixture and the organic material was extracted with ethyl acetate. The organic phase was dried over magnesium sulfate, filtered, and concentrated under reduced pressure to provide a yellow semi-solid (240 mg). The solid was dissolved in toluene, anhydrous ammonium acetate (1.1 g, 14 mmol) was added and the reaction was heated at 112° C. for four hours. The reaction mixture was cooled to room temperature, diluted with water and the organic material was extracted two times with ethyl acetate. The combined organic phase was washed with 1:9 v/v brine-water, then brine, and dried over magnesium sulfate, filter, and concentrated under reduced pressure. The residue was chromatographed on silica (25 g) eluted with 1:1 v/v to 4:1 ethyl acetate-hexane to afford the title compound (139 mg) as a yellow solid; $R_f$ 0.49 with 1:4 v/v hexanes-ethyl acetate; $^1$H-NMR (400 MHz; DMSO-$d_6$) δ 9.2 (s, 2H), 8.35-8.45 (m, 2H), 7.8 (s, 1H), 7.4-7.6 (m, 3H), 3.9-4.1 (m, 2.8-3.0 (m, 3H), 2.8-2.95 (m, 2H), 1.5-1.7 (M, 2H), 1.4 (m, 9H); MS (ESI$^+$) m/z 406 (M+1); H-PGDS FPBA IC$_{50}$: 0.15 µM.

Example 18

Preparation of 2-phenyl-5-(2-(piperidin-4-yl)-1H-imidazol-5-yl)pyrimidine

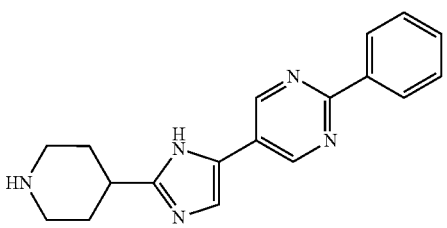 [SMILES: c1ccc(-c2ncc(-c3cnc(C4CCNCC4)[nH]3)cn2)cc1]

Solid tert-butyl 4-(4-(2-phenylpyrimidin-5-yl)-1H-imidazol-2-yl)piperidine-1-carboxylate (Example 17, 122 mg, 0.30 mmol) was treated with trifluoroacetic acid 2.0 mL) at room temperature for 15 minutes. Three times the reaction mixture was diluted with toluene and concentrated under reduced pressure to provide a dark semi-solid. The crude material was chromatographed on silica (12 g) eluted with 1:5:85 v/v acetic acid-methanol-dichloromethane. Some clean fractions were collected, concentrated, and the purified material was three times diluted with toluene and concentrated then promoted to solidify under hexane with scratching to afford the title compound (19 mg) as a light-pink acetate salt. The remaining fractions were collected, concentrated, three times diluted with toluene and concentrated to afford a semi-solid; $R_f$ 0.17 with 1/10/90 v/v acetic acid/methanol/dichloromethane; $^1$H-NMR (400 MHz; DMSO-$d_6$) δ 9.20 (s, 2H), 8.6-8.8 (br d, 1H), 8.3-8.5 (m, 3H), 7.83 (s, 1H), 7.45-7.55 (m, 3H), 3.2-3.5 (m, 2H), 2.95-3.2 (m, 3H), 2.1-2.2 (m, 2H), 1.8-2.0 (m, 5H); MS (ESI$^+$) m/z 306 (M+1); H-PGDS FPBA IC$_{50}$: 1 µM.

Example 19

Preparation of 5-(2-(1-benzylpiperidin-4-yl)-1H-imidazol-5-yl)-2-phenylpyrimidine

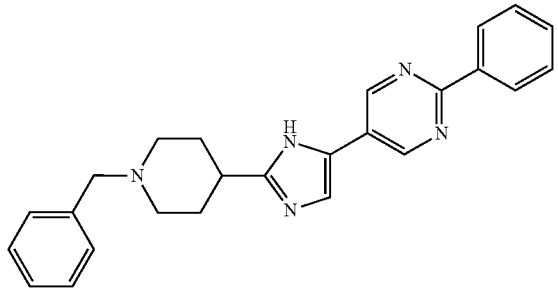 [SMILES: c1ccc(CN2CCC(c3ncc(-c4cnc(-c5ccccc5)nc4)[nH]3)CC2)cc1]

Step A: Preparation of sodium 1-benzylpiperidine-4-carboxylate

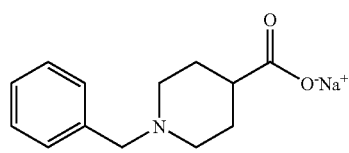

To a solution consisting of ethyl 1-benzylpiperidine-4-carboxylate (500 mg, 2.02 mmol) in ethanol (10 mL) was added 1 N sodium hydroxide (2.02 mL, 2.02 mmol) and the reaction mixture was stirred at room temperature overnight. Most of the ethanol was removed under reduced pressure and stirring was continued for six hours. Toluene was added to remove most of the water by azeotrope and the material was dried under high vacuum overnight to provide the title intermediate as a white solid.

Step B: Preparation of 5-(2-(1-benzylpiperidin-4-yl)-1H-imidazol-4-yl)-2-phenylpyrimidine

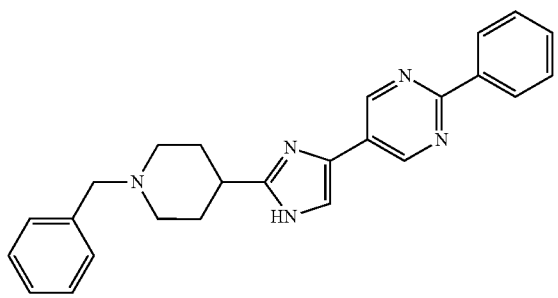 [SMILES: c1ccc(CN2CCC(c3nc(-c4cnc(-c5ccccc5)nc4)c[nH]3)CC2)cc1]

To a solution consisting of 2-bromo-1-(2-phenylpyrimidin-5-yl)ethanone (Example 14, Step B, 50 mg, 0.18 mmol) in tetrahydrofuran (1.5 mL) at room temperature was added sodium 1-benzylpiperidine-4-carboxylate (Step A, 48 mg, 0.20 mmol). The reaction mixture was warmed to 40° C. for one hour, and more sodium 1-benzylpiperidine-4-carboxylate (67 mg, 0.29 mmol) was added and warmed at 40° C. for two hours. The reaction mixture was cooled to room temperature, stirred vigorously while water (15 mL) was added quickly. The precipitate was filtered, washed with water and dried under high vacuum overnight to provide crude material (43.3 mg) that was dissolved in toluene (4 mL). To this solution was added freshly prepared ammonium acetate under toluene (400 mg wet with toluene and acetic acid). The reaction mixture was heated at 112° C. for 3.5 hours, cooled to room temperature, separated from the solidified ammonium acetate, concentrated under reduced pressure and chromatographed on silica (4 g) eluted with ethyl acetate and 1:9 v/v ethanol-ethyl acetate. The product was triturated under ethyl acetate/hexane/dichloromethane (0.3 mL) and filtered to the title compound (10 mg) as a tan crystalline-like solid; $R_f$ 0.17 with 1:9 v/v ethanol-ethyl acetate; melting point 223° C.; $^1$H-NMR (400 MHz; DMSO-$d_6$) δ 9.20 (s, 2H), 8.35-8.45 (m, 2H), 7.80-7.82 (m, 1H), 7.5-7.6 (m, 4H), 7.3-7.4 (m, 4H), 7.2-7.3 (m, 1H), 3.5 (s, 2H), 2.7-2.9 (m, 2H), 2.65-2.8 (m, 1H), 2.0-2.2 (m, 2H), 1.85-1.95 (m, 2H), 1.7-1.85 (m, 2H); MS (ESI$^+$) m/z 396 (M+1); H-PGDS FPBA IC$_{50}$: 0.08 µM; H-PGDS inhibitor EIA IC$_{50}$: 0.006 µM.

The compounds of general structure 20a-c shown in Scheme 5 may be further derivatized to compounds of general structure 21a-c as illustrated in Scheme 6. A compound 20a, 20b, or 20c may be alkylated, acylated, or arylated by a number of methods known to those ordinarily skilled in the art to provide compounds 21a, 21b, and 21c, respectively, of the exemplary embodiments. In general, an amine intermediate 20a-c is reacted with an electrophile Q-(CH$_2$)$_q$-LG, wherein Q and q are as defined above and LG is a leaving group, such as chloro, bromo, iodo, O-tosyl, O-methanesulfonyl, or O-trifluoromethanesulfonyl in the presence of a base, such as triethylamine, cesium carbonate, or sodium tert-butoxide, in a solvent such as THF, DMF, dichloromethane, or toluene. Groups with the general structure Q-(C$_2$)$_q$— may further be derivatized or manipulated in order to convert the compound to another compound of the exemplary embodiment. Such conversions include, but are not limited to, oxidation, reduction, deprotection, homologation, alkylation, acylation, or arylation and may be carried out by methods known to those ordinarily skilled in the art. The preparations of Examples 20, 23, 24, 25B, 26, 27, 29, and 31 employ this general method.

Scheme 6: General derivatization of amine compounds 20a-c

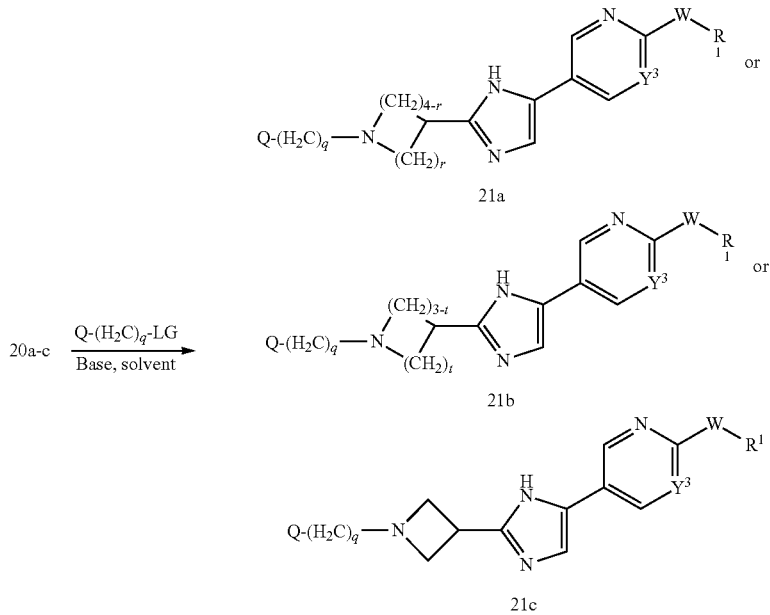

Example 20

Preparation of (4-(4-(2-phenylpyrimidin-5-yl)-1H-imidazol-2-yl)piperidin-1-yl)(pyridin-3-yl)methanone

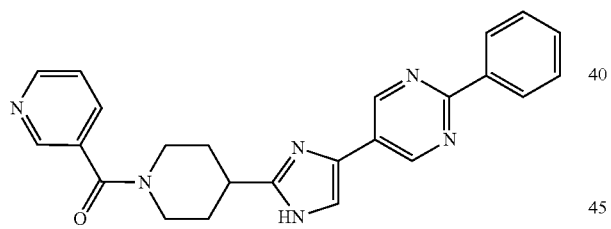

To a 0° C. solution of 2-phenyl-5-(2-(piperidin-4-yl)-1H-imidazol-4-yl)pyrimidine (76 mg, 0.25 mmol) in tetrahydrofuran (4 mL) was added triethylamine (51 mg, 0.50 mmol) followed by nicotinoyl chloride (49 mg, 0.27 mmol) and the reaction mixture was stirred for 1 hour at 0° C. then allowed to warm to room temperature. The reaction was diluted with water and the organic material extracted three times with ethyl acetate. The combined organic phase was dried over magnesium sulfate, filtered, and concentrated under reduced pressure. The crude solid was chromatographed on silica (4 g) and eluted with ethanol-ethyl acetate to give the title compound as a solid; melting point 234° C.; $R_f$ 0.31 with 0.5/10/40/50 acetic acid-isopropanol-hexane-dichloromethane; MS (ESI$^+$) m/z 411 (M+1); H-PGDS FPBA IC$_{50}$: 0.45 μM.

Example 21

Preparation of (±)-tert-butyl 3-(5-(2-phenylpyrimidin-5-yl)-1H-imidazol-2-yl)piperidine-1-carboxylate

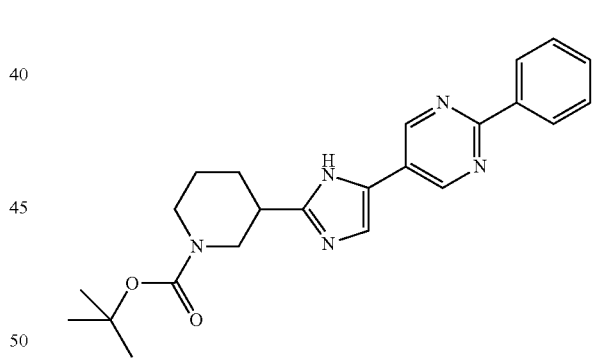

To a solution consisting of (±)-1-(tert-butoxycarbonyl)piperidine-3-carboxylic acid (42 mg, 0.18 mmol) in N,N-dimethylformamide (1.5 mL) was added cesium carbonate (117 mg, 0.36 mmol) and the reaction mixture was stirred for 15 minutes. To the reaction mixture was added 2-bromo-1-(2-phenylpyrimidin-5-yl)ethanone (Example 14, Step B, 50 mg, 0.18 mmol) and the mixture was stirred for 1.5 hours. Water was added to the vigorously stirred reaction mixture and the precipitate was filtered, washed with water and dried under high vacuum to provide a light green solid (42 mg). The solid (26 mg, 0.06 mmol) was dissolved in toluene, anhydrous ammonium acetate (146 mg, 1.9 mmol) was added and the reaction mixture was heated at 112° C. for four hours. The reaction mixture was cooled to room temperature and the liquid was separated from the solid and concentrated. The residue was chromatographed on silica (4 g) eluted with 1:4:5 v/v dichloromethane-ethyl acetate-hexane. Crystallization from methanol and water afforded the title compound (6.5 mg) as brown solid; R$_f$ 0.29 with 1:1 v/v hexanes-ethyl acetate; melting point 130° C.; $^1$H-NMR (400 MHz; DMSO-d$_6$) δ 9.20 (s, 2H), 8.35-8,45 (m, 2H), 7.85 (d, 1H), 7.5-7.6 (m, 3H), 4.0-4.4 (br d, 1H), 3.85-4.0 (m, 1H), 2.9-3.2 (br s, 1H), 2.7-2.9 (m, 2H), 2.0-2.2 (m, 1H), 1.65-1.7 (m, 2H), 1.3-1.5 (m, 1H), 1.41 (s, 9H); MS (ESI$^+$) m/z 406 (M+1); H-PGDS FPBA IC$_{50}$: 0.2 µM.

Example 22

Preparation of (±)-2-phenyl-5-(2-(piperidin-3-yl)-1H-imidazol-5-yl)pyrimidine

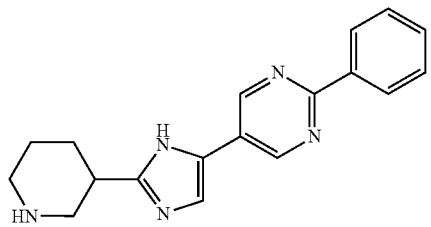 [SMILES: c1ccc(-c2ncc(-c3cnc(C4CCCNC4)[nH]3)cn2)cc1]

Solid (±)-tert-butyl 3-(4-(2-phenylpyrimidin-5-yl)-1H-imidazol-2-yl)piperidine-1-carboxylate (Example 21) was treated with 0.5 mL of trifluoroacetic acid at room temperature for 0.5 hour. Three times the reaction mixture was diluted with toluene and concentrated to give a dark semi-solid. The crude material was chromatographed on silica (4 g) eluted with 1:10:90 v/v acetic acid-methanol-dichloromethane. The clean fractions were collected, concentrated under reduced pressure, and the material was three times diluted with toluene and concentrated, then dried under high vacuum to afford the title compound as a pale yellow solid; R$_f$ 0.17 with 1:10:90 v/v acetic acid-methanol-dichloromethane; melting point 140° C.; $^1$H-NMR (400 MHz; DMSO-d$_6$) δ 9.22 (s, 2H), 8.5-9.2 (br s, 2H), 8.35-8,45 (m, 2H), 7.9 (d, 1H), 7.4-7.5 (m, 3H), 3.4-3.6 (m, 2H), 3.2-3.4 (m, 2H), 2.9-3.1 (m, 1H), 2.0-2.2 (m, 1H), 1.6-1.9 (m, 3H); MS (ESI$^+$) m/z 306 (M+1); H-PGDS FPBA IC$_{50}$: 1.25 µM.

Example 23

Preparation of (±)-5-(2-(1-benzylpiperidin-3-yl)-1H-imidazol-5-yl)-2-phenylpyrimidine

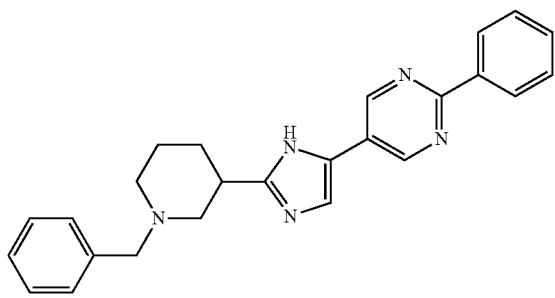 [SMILES: c1ccc(CN2CCCC(c3ncc(-c4cnc(-c5ccccc5)nc4)[nH]3)C2)cc1]

To a solution consisting of (±)-2-phenyl-5-(2-(piperidin-3-yl)-1H-imidazol-4-yl)pyrimidine (Example 22, 40 mg, 0.13 mmol) in dimethylformamide (2 mL) was added cesium carbonate (85 mg, 0.26 mmol) followed by benzyl bromide (27 mg, 0.16 mmol). The reaction mixture was stirred at room temperature for one hour and diluted with water and the organic material was extracted twice with ethyl acetate. The combined organic phase was dried over magnesium sulfate, filtered, and concentrated under reduced pressure. The residue was dissolved in dichloromethane/ethyl acetate and chromatographed on silica (4 g) eluted with 1:9 v/v ethanol-ethyl acetate. The purified material was diluted with toluene and concentrated. Solidification of the product was promoted with scratching under dichloromethane and hexane to afford the title compound (20 mg) as a colorless solid; melting point 179° C.; R$_f$ 0.19 with 1:9 v/v ethanol-ethyl acetate; $^1$H-NMR (400 MHz; DMSO-d$_6$) δ 12.1 (s, 1H), 9.18 (s, 2H), 8.2-8.4 (m, 2H), 7.8 (s, 1H), 7.4-7.6 (m, 4H), 7.22-7.35 (m, 4H), 7.18-7.22 (m, 4H), 3.4-3.6 (m, 2H), 2.9-3.0 (m, 2H), 2.7-2.9 (m, 1H), 2.02-2.1 (M, 1H), 1.9-2.1 (m, 2H), 1.62-1.8 (m, 1H), 1.5-1.62 (m, 2H); MS (ESI$^+$) m/z 396 (M+1); H-PGDS FPBA IC$_{50}$: 0.6 µM.

Example 24

Preparation of 2,2,2-trifluoro-1-(3-(4-(2-phenylpyrimidin-5-yl)-1H-imidazol-2-yl)piperidin-1-yl)ethanol

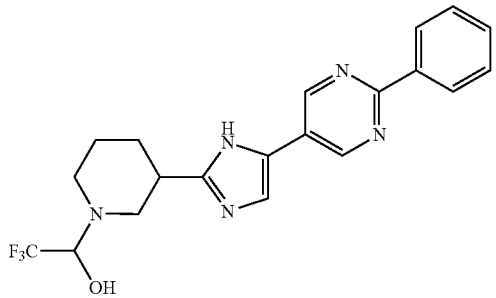 [SMILES: OC(N1CCCC(c2ncc(-c3cnc(-c4ccccc4)nc3)[nH]2)C1)C(F)(F)F]

To a room temperature solution of (±)-2,2,2-trifluoro-1-(3-(4-(2-phenylpyrimidin-5-yl)-1H-imidazol-2-yl)piperidin-1-yl)ethanone (18 mg, 0.04 mmol) in tetrahydrofuran (1 mL) was added borane-tetrahydrofuran (1M, 0.13 mL, 0.13 mmol). The reaction mixture was heated at 65° C. for four hours, cooled, treated carefully with 6 mL of 6N HCl and 2 mL of ethanol and heated at 65° C. for one hour. The cooled reaction mixture was extracted four times with ethyl acetate and the organic phase was dried over magnesium sulfate, filtered, and rotovapped. The residue was chromatographed on silica (4 g) and eluted with 1:20:80 to 5:30:70 triethylamine-isopropanol-hexanes to give the title compound as a bright yellow solid white solid; R$_f$ 0.15 with 1:20:80 v/v triethylamine-isopropanol-hexanes; MS (ESI$^+$) m/z 404 (M+1); H-PGDS FPBA IC$_{50}$: 10 µM.

Examples 25A and 25B

Preparation of (±)-N-methyl-3-(1-(methylcarbamoyl)-4-(2-phenylpyrimidin-5-yl)-1H-imidazol-2-yl)piperidine-1-carboxamide (Example 25A) and (±)-N-methyl-3-(5-(2-phenylpyrimidin-5-yl)-1H-imidazol-2-yl)piperidine-1-carboxamide (Example 25B)

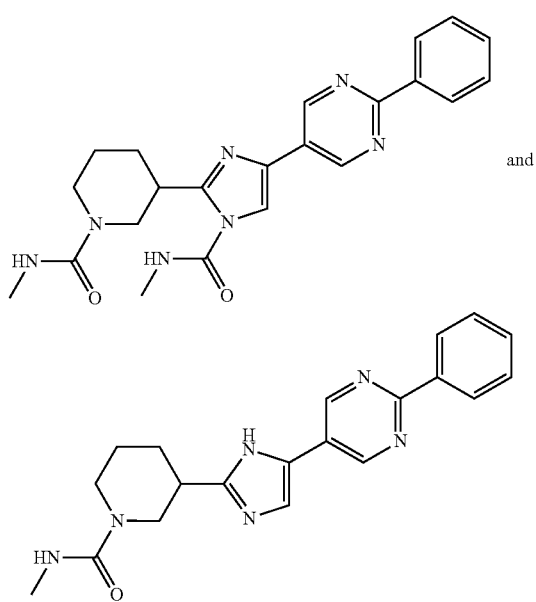

To a suspension consisting of 2-phenyl-5-(2-(piperidin-3-yl)-1H-imidazol-4-yl)pyrimidine (Example 22, 40 mg, 0.13 mmol) in dichloromethane (2 mL) was added methyl isocyanate (9 mg, 0.16 mmol) and the reaction mixture was stirred for one hour. TLC (1:10:90 v/v acetic acid-methanol-dichloromethane) indicated no reaction. The mixture was diluted with tetrahydrofuran (2 mL) to provide a homogeneous solution, and methyl isocyanate (9 mg, 0.16 mmol) was added. The reaction mixture was stirred overnight and the precipitate was filtered to provide (±)-N-methyl-3-(1-(methylcarbamoyl)-4-(2-phenylpyrimidin-5-yl)-1H-imidazol-2-yl)piperidine-1-carboxamide (Example 25A, 10 mg) as a white solid; $R_f$ 0.31 with 1:9 v/v ethanol-ethyl acetate; $^1$H-NMR (400 MHz; DMSO-$d_6$) δ 9.20 (s, 2H), 8.59 (br qt, 1H), 8.35-8.45 (m, 2H), 8.18 (s, 1H), 7.45-7.55 (m, 3H), 6.40 (br qt, 1H), 4.1-4.2 (m, 1H), 3.9-4.0 (m, 1H), 3.2-3.4 (m, 1H), 2.9-3.1 (m, 1H), 2.81 (d, 3H), 2.65-2.75 (m, 1H), 2.55 (d, 3H), 2.0-2.1 (m, 1H), 1.6-1.7 (m, 2H), 1.3-1.45 (m, 1H); MS (ESI$^+$) m/z 420 (M+1); H-PGDS FPBA IC$_{50}$: 0.62 µM.

The filtrate was diluted with water. The organic material was extracted twice with ethyl acetate and the combined organic phase was washed with brine, dried over magnesium sulfate, filtered, and concentrated under reduced pressure. The crude material was purified on a silica column to afford (±)-N-methyl-3-(4-(2-phenylpyrimidin-5-yl)-1H-imidazol-2-yl)piperidine-1-carboxamide (Example 25B, 5.5 mg) as a solid; $R_f$ 0.17 with 1:9 v/v ethanol-ethyl acetate; $^1$H-NMR (400 MHz; DMSO-$d_6$) δ 12.2 (s, 1H), 9.21 (s, 2H), 8.35-8.45 (m, 2H), 7.84-7.85 (m, 1H), 7.50-7.55 (m, 3H), 6.45 (br qt, 1H), 4.15-4.22 (m, 1H), 3.85-3.95 (m, 1H), 2.85-2.95 (m, 1H), 2.65-2.85 (m, 2H), 2.55 (d, 3H), 2.51 (d, 3H), 2.0-2.1 (m, 1H), 1.6-1.8 (m, 2H), 1.35-1.5 (m, 1H); MS (ESI$^+$) m/z 363 (M+1); H-PGDS FPBA IC$_{50}$: 0.3 µM.

Example 26

Preparation of (±)-cyclopropyl(3-(5-(2-phenylpyrimidin-5-yl)-1H-imidazol-2-yl)piperidin-1-yl)methanone

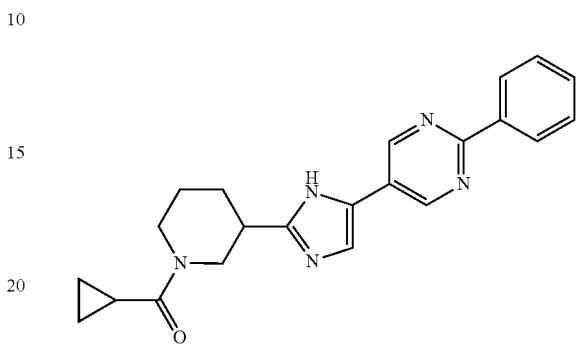

The title compound is prepared in the same manner as Example 27 except that cyclopropanecarbonyl chloride is used instead of trifluoroacetic anhydride. The reaction is carried out at 0° C. and allowed to warm to room temperature. The reaction mixture is diluted with water, extracted with ethyl acetate and the organic phase is dried over magnesium sulfate, filtered, and evaporated. The crude is purified on a silica column.

Example 27

Preparation of (±)-2,2,2-trifluoro-1-(3-(4-(2-phenylpyrimidin-5-yl)-1H-imidazol-2-yl)piperidin-1-yl)ethanone

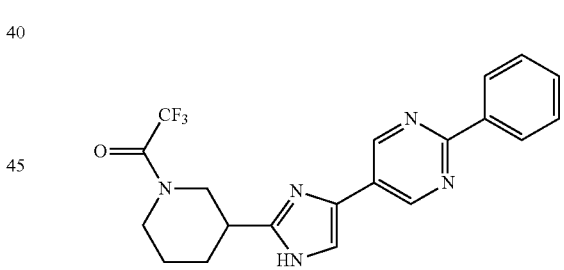

To a 0° C. solution of 2-phenyl-5-(2-(piperidin-3-yl)-1H-imidazol-4-yl)pyrimidine (40 mg, 0.13 mmol) in tetrahydrofuran (2 mL) was added triethylamine (26 mg, 0.26 mmol) followed by trifluoroacetic anhydride (30 mg, 0.14 mmol) and the reaction mixture was stirred for 1 hour at 0° C. then allowed to warm to room temperature. To −78° C. solution of 2-phenyl-5-(2-(piperidin-3-yl)-1H-imidazol-4-yl)pyrimidine (40 mg, 0.13 mmol) in tetrahydrofuran (2 mL) was added triethylamine (26 mg, 0.26 mmol) followed by trifluoroacetic anhydride (30 mg, 0.14 mmol) and the reaction mixture was stirred and allowed to slowly warm to room temperature. The two reaction mixtures were combined, the volatile materials were removed, and the crude reaction mixture was treated with 0.5 mL of N-methylpiperazine at 50° C. for 1 hour. The addition of 30 mL of water caused a precipitate that was filtered and washed with water and dried in high vacuum. The crude solid was chromatographed on 4 g of silica eluted with ethyl acetate/hexane to give 30 mg of the title compound as a white solid. R$_f$ 0.20 with 1:1 v/v hexanes-ethyl acetate; $^1$H-NMR (400 MHz; DMSO-d$_6$) δ 9.21 (s, 2H), 8.35-8.45 (m, 2H), 7.85-7.90 (m, 1H), 7.5-7.6 (m, 3H), 4.20-4.55 (m, 1H), 3.80-4.15 (m, 1H), 2.0-3.7 (m, 3H), 2.1-2.2 (m, 1H), 1.75-2.0 (m, 2H), 1.5-1.7 (m, 1H); MS (ESI$^+$) m/z 402 (M+1); H-PGDS FPBA IC$_{50}$: 0.09 μM.

Additional elution of the column with 1/9 ethanol/ethyl acetate provided 6 mg of a white solid identified as 1-(3-(4-(2-phenylpyrimidin-5-yl)-1H-imidazol-2-yl)piperidin-1-yl)ethanone. R$_f$ 0.17 with 1:9 v/v ethanol-ethyl acetate; MS (ESI$^+$) m/z 348 (M+1); H-PGDS FPBA IC$_{50}$: 0.09 μM.

Example 28

Preparation of (±)-tert-butyl 3-(5-(2-phenylpyrimidin-5-yl)-1H-imidazol-2-yl)pyrrolidine-1-carboxylate

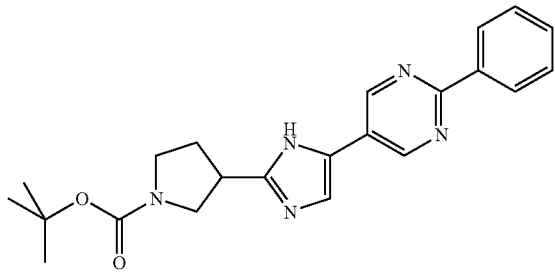 [SMILES: CC(C)(C)OC(=O)N1CCC(c2ncc(-c3cnc(-c4ccccc4)nc3)[nH]2)C1]

To a solution consisting of 1-(tert-butoxycarbonyl)pyrrolidine-3-carboxylic acid (159 mg, 0.74 mmol) in dimethylformamide (7 mL) was added cesium carbonate (459 mg, 1.44 mmol) and the reaction mixture was stirred for 15 minutes. To the reaction mixture was added 2-bromo-1-(2-phenylpyrimidin-5-yl)ethanone (Example 14, Step B, 200 mg, 0.72 mmol) and the mixture was stirred for two hours. Water was added to the reaction mixture and the organic material was extracted with ethyl acetate. The organic phase was dried over magnesium sulfate, filtered, and concentrated to afford a yellow semi-solid (250 mg). The solid was dissolved in toluene, anhydrous ammonium acetate (1.2 g, 15 mmol) was added and the reaction mixture was heated at 112° C. for four hours. The reaction mixture was cooled to room temperature, diluted with water and the organic material was extracted twice with ethyl acetate. The combined organic phase was washed with 1:9 v/v brine-water, then brine, and dried over magnesium sulfate, filtered, and concentrated under reduced pressure. The residue was chromatographed on silica (25 g). Elution with 1:1 v/v to 4:1 ethyl acetate-hexane afforded the title compound (83 mg) as a yellow solid; R$_f$ 0.43 with 1:4 v/v hexanes-ethyl acetate; melting point 219° C.; $^1$H-NMR (400 MHz; DMSO-d$_6$) δ 9.18 (s, 2H), 8.3-8.4 (m, 2H), 7.24 (d, 1H), 7.45-7.55 (m, 3H), 3.6-3.7 (m, 1H), 3.4-3.6 (m, 3H), 3.2-3.4 (m, 3H, under water peak), 2.0-2.35 (m, 2H), 1.4 (m, 9H); MS (ESI$^+$) m/z 392 (M+1); H-PGDS FPBA IC$_{50}$: 0.15 μM.

Example 29

Preparation of (±)-5-(2-(1-benzylpyrrolidin-3-yl)-1H-imidazol-5-yl)-2-phenylpyrimidine

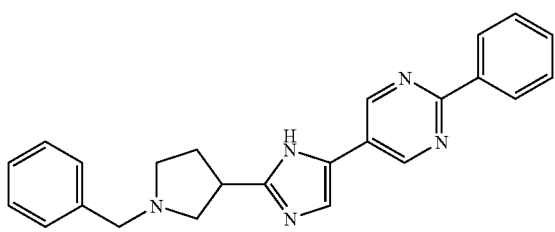 [SMILES: c1ccc(CN2CCC(c3ncc(-c4cnc(-c5ccccc5)nc4)[nH]3)C2)cc1]

The title compound is prepared in the same manner as example 23 except that (±)-2-phenyl-5-(2-(pyrrolidin-3-yl)-1H-imidazol-5-yl)pyrimidine is used instead of (±)-2-phenyl-5-(2-(piperidin-3-yl)-1H-imidazol-4-yl)pyrimidine.

Example 30

Preparation of (±)-2-phenyl-5-(2-(pyrrolidin-3-yl)-1H-imidazol-5-yl)pyrimidine

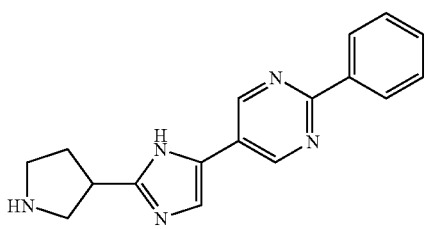 [SMILES: c1ccc(-c2ncc(-c3cnc(C4CCNC4)[nH]3)cn2)cc1]

The title compound was prepared according to the method described in Example 22, except that (±)-tert-butyl 3-(4-(2-phenylpyrimidin-5-yl)-1H-imidazol-2-yl)pyrrolidine-1-carboxylate (Example 28) was used instead of (±)-tert-butyl 3-(4-(2-phenylpyrimidin-5-yl)-1H-imidazol-2-yl)piperidine-1-carboxylate. MS (ESI$^+$) m/z 292 (M+1); H-PGDS FPBA IC$_{50}$: 2 μM.

Example 31

Preparation of (±)-N-methyl-3-(4-(2-phenylpyrimidin-5-yl)-1H-imidazol-2-yl)pyrrolidine-1-carboxamide

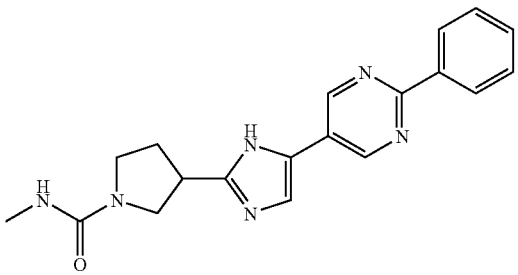 [SMILES: CNC(=O)N1CCC(c2ncc(-c3cnc(-c4ccccc4)nc3)[nH]2)C1]

The title compound is prepared in the same manner as Example 25B except that (±)-2-phenyl-5-(2-(pyrrolidin-3-yl)-1H-imidazol-5-yl)pyrimidine is used instead of (±)-2-phenyl-5-(2-(piperidin-3-yl)-1H-imidazol-4-yl)pyrimidine and the reaction is done in tetrahydrofuran instead of a combination of dichloromethane and tetrahydrofuran.

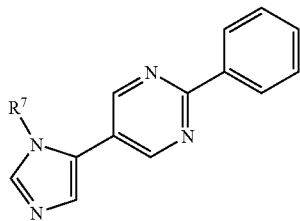

| Ex. | R[7] | H-PGDS FPBA IC$_{50}$ (μM) | H-PGDS Inhibitor EIA IC$_{50}$ (μM) |
|---|---|---|---|
| 5 | H | 5 | |
| 32 | Me | 7.6 | |
| 33 | Bn | 2 | |

Example 32

Preparation of
5-(1-methyl-1H-imidazol-5-yl)-2-phenyl pyrimidine

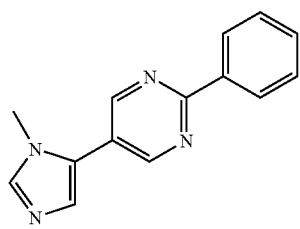 [SMILES: Cn1cncc1-c1cnc(-c2ccccc2)nc1]

The title compound was prepared by the method described in Example 1, Steps A-C, except that commercially available 1-methylimidazole (Aldrich) was used instead of 2-phenylimidazole in Step B; R$_f$ 0.31 with 95:5 v/v dichloromethane-methanol; $^1$H-NMR (400 MHz; CDCl$_3$) δ 8.87 (s, 2H), 8.48 (m, 2H), 7.63 (s, 1H), 7.54 (m, 3H), 7.28 (s, 1H); MS (ESI$^+$) m/z 237.1 (M+1); melting point 144° C.; H-PGDS FPBA IC$_{50}$: 7.6 μM.

Example 33

Preparation of
5-(1-benzyl-1H-imidazol-5-yl)-2-phenylpyrimidine

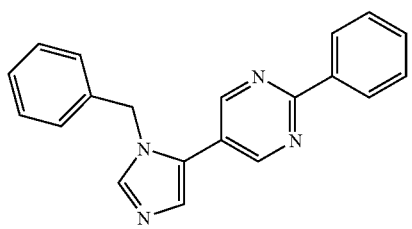 [SMILES: c1ccc(Cn2cncc2-c2cnc(-c3ccccc3)nc2)cc1]

The title compound was prepared by the method described in Example 1, Steps A-C, except that imidazole was used instead of 2-phenylimidazole in Step B; R$_f$ 0.18 with 100% ethyl acetate; melting point 140° C.; $^1$H-NMR (400 MHz; DMSO-d$_6$) δ 8.85 (s, 2H), 8.39 (m, 2H), 8.05 (s, 1H), 7.55 (m, 3H), 7.45-7.20 (m, 5H) 6.98 (dd, 2H), 5.43 (s, 2H); MS (ESI$^+$) m/z 313.0 (M+1); H-PGDS FPBA IC$_{50}$: 2 μM.

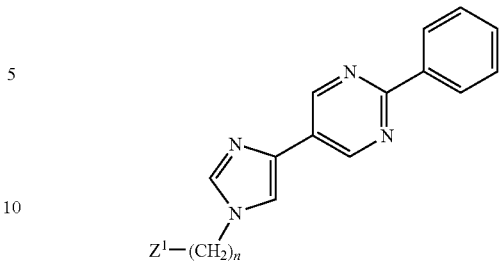

| Ex. | Z$^1$-(CH$_2$)$_n$ | H-PGDS FPBA IC$_{50}$ (μM) | H-PGDS Inhibitor EIA IC$_{50}$ (μM) |
|---|---|---|---|
| 5 | H (Z$^1$ = H, n = 0) | 5 | |
| 34 | Bn (Z$^1$ = Ph, n = 1) | 4 | |
| 35 | Me (Z$^1$ = H, n = 1) | | |
| 36 | (3-pyridyl)-CH$_2$— | | |
| 37 | 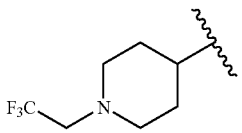 | | |

Example 34

Preparation of
5-(1-benzyl-1H-imidazol-4-yl)-2-phenylpyrimidine

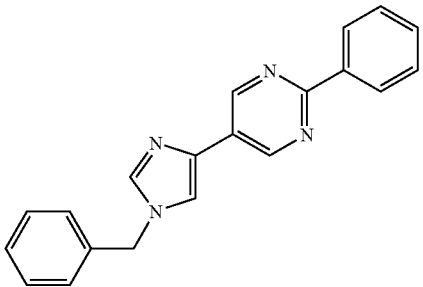 [SMILES: c1ccc(Cn2cnc(-c3cnc(-c4ccccc4)nc3)c2)cc1]

Step A: Preparation of
2-phenyl-5-(1-trityl-1H-imidazol-4-yl)pyrimidine

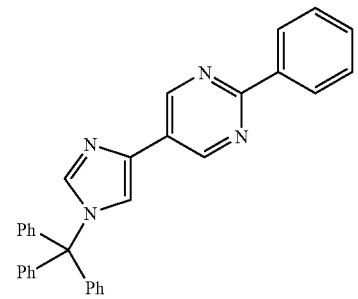 [SMILES: c1ccc(-c2ncc(-c3cn(C(c4ccccc4)(c4ccccc4)c4ccccc4)cn3)cn2)cc1]

To a solution of 4-Iodo-1-trityl-1H-imidazole (Synthonix, 2.0 g, 4.58 mmol) in THF (50 mL) at room temperature was added ethylmagnesium bromide (Aldrich, 1.0 M solution in THF, 5.5 mL, 5.50 mmol) under dry conditions. After stirring for 90 minutes, zinc chloride (Aldrich, 0.749. g, 5.50 mmol) was added to the reaction mixture. After stirring for an additional 90 minutes, tetrakis(triphenyl)phosphine)palladium (Strem, 0.529 g, 0.46 mmol) and 5-bromo-2-phenylpyrimidine (as prepared in Example 1, step A, 1.29 g, 5.50 mmol) were added to the reaction mixture. The reaction mixture was heated in a 70° C. oil bath overnight. Upon cooling, the reaction was diluted with dichloromethane and washed with 0.5 M EDTA buffer (at pH ~9) (2×250 mL) followed by brine (150 mL). The organics were dried over sodium sulfate, filtered, and concentrated. The crude product was purified by flash silica column chromatography using an 80 g Silicycle® column (elution with 10-30% ethyl acetate in hexane) which afforded the desired intermediate, 2-phenyl-5-(1-trityl-1H-imidazol-4-yl)pyrimidine, as a white solid (1.38 g, 65%). $R_f$ 0.87 with 95:5 v/v dichloromethane-methanol; $^1$H-NMR (400 MHz; DMSO-$d_6$) δ 9.29 (s, 2H), 8.42 (m, 2H), 7.92 (d, 1H), 7.62 (d, 1H), 7.56-7.43 (m, 13H), 7.24-7.22 (m, 6H); MS (ESI$^-$) m/z 463.0 (M−1); H-PGDS FPBA IC$_{50}$: >20 μM.

Step B: Preparation of
5-(1H-imidazol-4-yl)-2-phenylpyrmidine

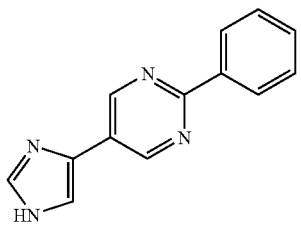 [SMILES: c1ccc(-c2ncc(-c3c[nH]cn3)cn2)cc1]

The title intermediate is chemically equivalent to Example 5, 5-(1H-imidazol-5-yl)-2-phenylpyrimidine. An alternative preparation of this compound is presented in this step. To a solution consisting of 2-phenyl-5-(1-trityl-1H-imidazol-4-yl)pyrimidine (Step A, 0.786 g, 1.69 mmol) in ethanol (50 mL) was added concentrated aqueous hydrochloric acid (5 mL) at room temperature. The reaction mixture was heated in a 50° C. oil bath for 90 minutes. Upon cooling, the reaction was concentrated under vacuum to about half the original amount of solvent. Ethyl ether (30 mL) was added to the mixture and the product precipitate was collected by filtration. The solid was washed with excess ethyl ether and then dried under vacuum to afford the intermediate, 5-(1H-imidazol-4-yl)-2-phenylpyrimidine, as a white solid (0.336 g, 76%). $R_f$ 0.14 with 95:5 v/v dichloromethane-methanol; $^1$H-NMR (400 MHz; DMSO-$d_6$) δ 9.49 (s, 2H), 9.41 (d, 1H), 8.49-8.44 (m, 3H), 7.61-7.58 (m, 3H); MS (ESI$^+$) m/z 223.1 (M+1); H-PGDS FPBA IC$_{50}$: 5 μM.

Step C: Preparation of
5-(1-benzyl-1H-imidazol-4-yl)-2-phenylpyrimidine

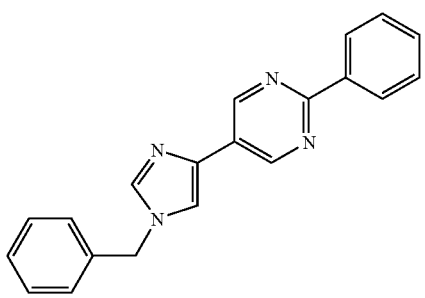 [SMILES: c1ccc(Cn2cnc(-c3cnc(-c4ccccc4)nc3)c2)cc1]

To a solution consisting of 5-(1H-imidazol-4-yl)-2-phenylpyrimidine (Step B, 0.050 g, 0.193 mmol) in N,N-dimethylformamide (10 mL) was added potassium carbonate (0.133 g, 0.965 mmol) at room temperature under dry conditions. After heating the reaction mixture in an 80° C. oil bath for one hour, benzyl bromide (Aldrich, 0.039 g, 0.231 mmol) was added to the mixture. The solution was left stirring in an 80° C. oil bath for 24 hours. Upon cooling, the reaction was diluted with dichloromethane (100 mL) and washed with saturated aqueous ammonium chloride (50 mL), water (50 mL) and brine (50 mL). The organic layer was dried over sodium sulfate, filtered, and concentrated. The residue was chromatographed on silica. Elution through an 8-g Silicycle® flash silica cartridge with gradient of 100% dichloromethane to 5% methanol in dichloromethane afforded the title compound as a white solid (22 mg, 36%). $R_f$ 0.56 with 95:5 v/v dichloromethane-methanol; melting point 195° C; $^1$H-NMR (400 MHz; DMSO-$d_6$) δ 9.25 (s, 2H), 8.44-8.42 (m, 2H), 8.03 (s, 2H), 7.56-7.54 (m, 3H), 7.45-7.36 (m, 5H), 5.38 (s, 2H); MS (ESI$^+$) m/z 313.1 (M+1); H-PGDS FPBA IC$_{50}$: 4 μM.

Example 35

Preparation of
5-(1-methyl-1H-imidazol-4-yl)-2-phenylpyrimidine

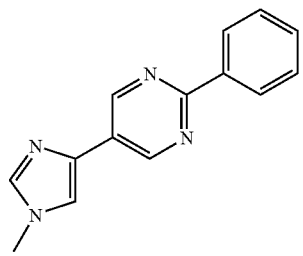 [SMILES: Cn1cnc(-c2cnc(-c3ccccc3)nc2)c1]

The title compound is prepared by the method described in Example 34, Steps A-C, except that iodomethane is used instead of benzyl bromide in Step C.

Example 36

Preparation of
5-(1-benzyl-1H-imidazol-4-yl)-2-phenylpyrimidine

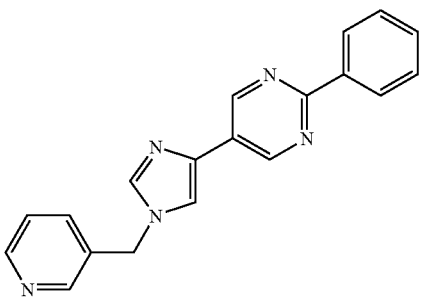 [SMILES: c1ccc(-c2ncc(-c3cn(Cc4cccnc4)cn3)cn2)cc1]

The title compound is prepared by the method described in Example 34, Steps A-C, except that 3-bromomethypyridine hydrobromide is used instead of benzyl bromide in Step C.

Example 37

Preparation of 2-phenyl-5-(1-(1-(2,2,2-trifluoroethyl)piperidin-4-yl)-1H-imidazol-4-yl)pyrimidine

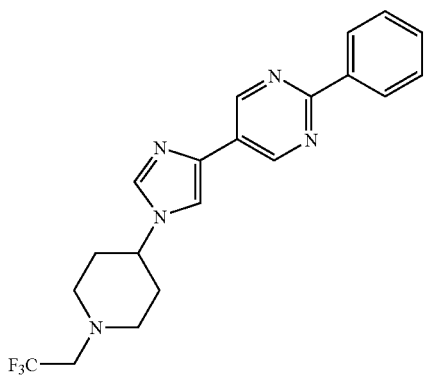 [SMILES: FC(F)(F)CN1CCC(n2cnc(-c3cnc(-c4ccccc4)nc3)c2)CC1]

The title compound was prepared by the method described in Example 34, Steps A-C, except that tert-butyl 4-(tosyloxy)piperidine-1-carboxylate is used instead of benzyl bromide in Step C. The nitrogen of the piperidine is deprotected and derivatized in the manner described in Examples 22 and 24, respectively.

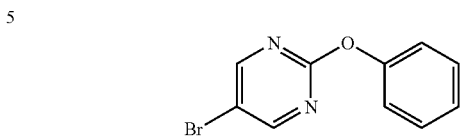

| Ex. | $R^2$ | H-PGDS FPBA $IC_{50}$ (μM) | H-PGDS Inhibitor EIA $IC_{50}$ (μM) |
|---|---|---|---|
| 38 | Ph | 4 | |
| 39 | Bn | 10 | |
| 40 | 3-pyridyl | 0.625 | 0.37 |

Example 38

Preparation of 2-phenoxy-5-(2-phenyl-1H-imidazol-5-yl)pyrimidine

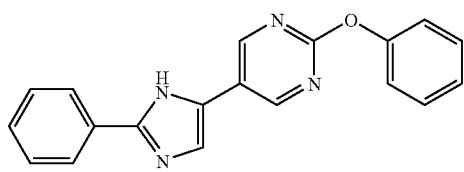 [SMILES: c1ccc(Oc2ncc(-c3cnc(-c4ccccc4)[nH]3)cn2)cc1]

Step A: Preparation of 5-bromo-2-phenoxypyrimidine

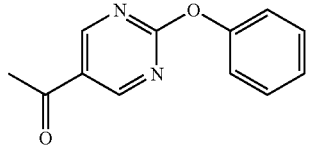 [SMILES: CC(=O)c1cnc(Oc2ccccc2)nc1]

A mixture consisting of 5-bromo-2-iodopyrimidine (Bridge Organics, 1.01 g, 3.57 mmol), phenol (Aldrich, 3.35 g, 35.7 mmol), and potassium carbonate (Aldrich, 4.93 g, 35.7 mmol) was stirred neat at 165° C. under a nitrogen atmosphere for four hours. After cooling to room temperature, the mixture was partitioned between ethyl acetate (250 mL) and 1 N hydrochloric acid (4×200 mL). The organic layer was washed with 1 N hydrochloric acid until disappearance of color in the aqueous layer. The phases were separated and the organic phase was washed with water (100 mL) and brine (100 mL). The organic layer was dried over anhydrous magnesium sulfate and concentrated under reduced pressure to provide an orange oil (1.1 g). The product was purified by flash silica column chromatography. Elution through an 80-g Silicycle® flash silica cartridge with 10% ethyl acetate in hexanes afforded the title compound as a white solid (0.82 g, 92% yield); $R_f$ 0.51 with 8:2 v/v hexanes-ethyl acetate; $^1$H-NMR (400 MHz; CDCl$_3$) δ 8.56 (s, 2H), 7.46-7.41 (m, 2H), 7.30-7.24 (m, 1H), 7.20-7.16 (m, 2H); MS (APCI$^+$) m/z 252.9 (M+1).

Step B: Preparation of 1-(2-phenoxypyrimidin-5-yl)methanone

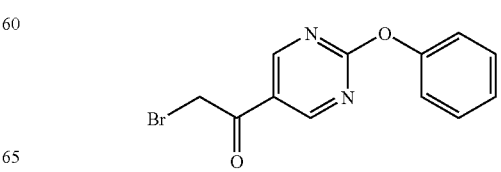

The title intermediate was prepared by the method described in Example 14, Step B, except that 5-bromo-2-phenoxypyrimidine was used instead of 5-bromo-2-phenylpyrimidine. The residue from the work up was dissolved in dichloromethane and diluted with hexane, was applied to an 80-g silica column eluted with 1:4 ethyl acetate-hexane to afford the title intermediate (690 mg, 65% yield); $R_f$ 0.29 with 3:1 v/v hexanes-ethyl acetate solvent system; $^1$H-NMR (400 MHz; DMSO-d$_6$) δ 9.17 (s, 2H), 7.4-7.6 (m, 2H), 7.2-7.4 (m, 3H), 2.60 (s, 3H); MS (ESI$^+$) m/z 215 (M+1).

Step C: Preparation of 2-bromo-1-(2-phenoxypyrimidin-5-yl)ethanone

To a solution consisting of 1-(2-phenoxypyrimidin-5-yl)ethanone (Step B, 400 mg, 1.87 mmol) in dichloromethane (14 mL) was added tetrabutylammonium tribromide (990 mg, 2.05 mmol). The reaction mixture was sealed with a screw top and warmed at 40° C. overnight and allowed to cool to room temperature. Hexane (4 mL) was subsequently added. After three hours and little precipitation, additional (150 mg) tetrabutylammonium tribromide was added and the reaction mixture was stirred overnight at room temperature. The pale yellow precipitate that formed was collected on a filter and washed with 1:1 dichloromethane-hexane to afford the title intermediate (375 mg, 68%); $R_f$ 0.43 with 3:1 v/v hexanes-ethyl acetate; MS (ESI$^+$) m/z 295, 293 (M+1, Br isotopes).

Step D: Preparation of
2-oxo-2-(2-phenoxypyrimidin-5-yl)ethyl benzoate

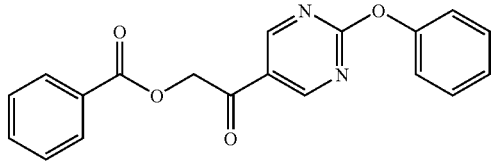 [SMILES: O=C(COC(=O)c1ccccc1)c1cnc(Oc2ccccc2)nc1]

To a mixture consisting of benzoic acid (21 mg, 0.17 mmol) and cesium carbonate (112 mg, 0.34 mmol) in DMF (2.5 mL) was added 2-bromo-1-(2-phenoxypyrimidin-5-yl)ethanone (50 mg, 0.17 mmol). Upon stirring at room temperature (30 minutes), the solution became dark amber. The reaction mixture was combined with ethyl acetate and washed sequentially with water and brine. The organic layer was dried with sodium sulfate, filtered and concentrated under reduced pressure followed by concentration with toluene. The title intermediate was isolated as a dark yellow solid (40 mg, 70% yield); TLC (silica) $R_f$ 0.44, 3:1 v/v hexanes-ethyl acetate.

Step E: Preparation of
2-phenoxy-5-(2-phenyl-1H-imidazol-5-yl)pyrimidine

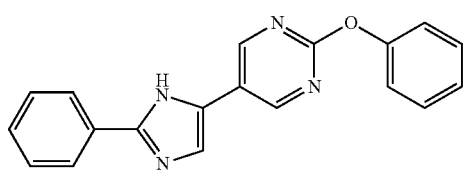 [SMILES: c1ccc(Oc2ncc(-c3cnc(-c4ccccc4)[nH]3)cn2)cc1]

A mixture consisting of 2-oxo-2-(2-phenoxypyrimidin-5-yl)ethyl benzoate (Step A, 40 mg), freshly prepared ammonium acetate (315 mg wet with toluene), and toluene (4 mL) was heated in a capped vial to 112° C. overnight. The reaction mixture was poured into a 0.1 M aqueous sodium bicarbonate solution and extracted twice with ethyl acetate. The organic layer was washed with brine, dried with magnesium sulfate, filtered and concentrated under reduced pressure. The crude brown solid was purified by flash chromatography using a 4:1 to 1:1 hexanes-ethyl acetate gradient affording the title compound (11.2 mg, 29% yield) as a light tan solid; melting point 254° C.; $^1$H-NMR (400 MHz; DMSO-d$_6$) δ 9.05 (s, 2H), 7.96-8.02 (m, 2H), 7.85-7.92 (m, 2H), 7.42-7.54 (m, 4H), 7.35-7.41 (m, 1H), 7.20-7.29 (m, 2H); LC/MS (ESI$^+$) m/z 315; H-PGDS FPBA IC$_{50}$: 4 μM.

Example 39

Preparation of
5-(2-benzyl-1H-imidazol-4-yl)-2-phenoxypyrimidine

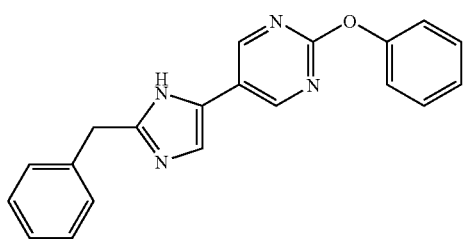 [SMILES: c1ccc(Cc2ncc(-c3cnc(Oc4ccccc4)nc3)[nH]2)cc1]

Step A: Preparation of
2-oxo-2-(2-phenoxypyrimidin-5-yl)ethyl
2-phenylacetate

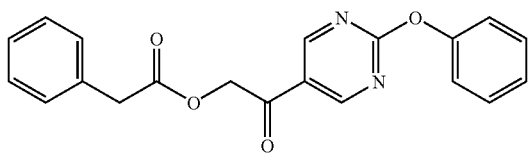 [SMILES: O=C(Cc1ccccc1)OCC(=O)c1cnc(Oc2ccccc2)nc1]

The title intermediate was prepared according to the method described in Example 38, Step D except that phenylacetic acid was used instead of benzoic acid. The title intermediate was isolated as a dark yellow solid (47 mg); TLC (silica) $R_f$ 0.64, 3:1 v/v hexanes-ethyl acetate.

Step B: Preparation of
5-(2-benzyl-1H-imidazol-4-yl)-2-phenoxypyrimidine

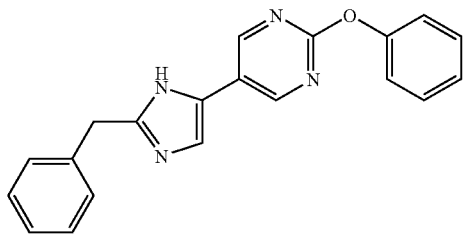 [SMILES: c1ccc(Cc2ncc(-c3cnc(Oc4ccccc4)nc3)[nH]2)cc1]

The title compound was prepared according to the procedure described in Example 27, Step E except that 2-oxo-2-(2-phenoxypyrimidin-5-yl)ethyl 2-phenylacetate was used instead of 2-oxo-2-(2-phenoxypyrimidin-5-yl)ethyl benzoate. The crude brown solid was purified by flash chromatography using a 4:1 to 1:1 hexanes-ethyl acetate gradient affording the title compound (9.9 mg, 23% yield) as a yellow solid; melting point 60° C.; $^1$H-NMR (400 MHz; DMSO-d$_6$)

δ 8.97 (s, 2H), 7.71 (s, 1H), 7.48-7.52 (m, 2H), 7.25-7.37 (m, 8H), 4.09 (s, 2H); LC/MS (ESI⁺) m/z 329; H-PGDS FPBA IC₅₀: 10 μM.

Example 40

Preparation of 2-phenoxy-5-(2-(pyridin-3-yl)-1H-imidazol-4-yl)pyrimidine

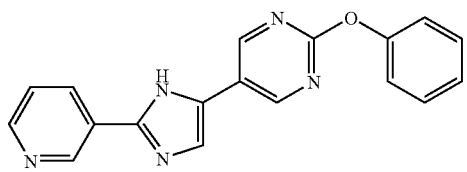 [SMILES: c1ccc(Oc2ncc(-c3cnc(-c4cccnc4)[nH]3)cn2)cc1]

Step A: Preparation of 2-oxo-2-(2-phenoxypyrimidin-5-yl)ethyl nicotinate

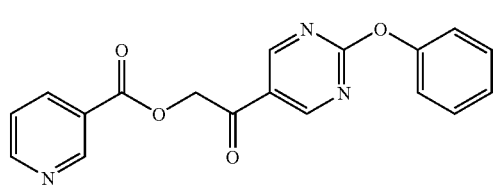 [SMILES: O=C(COC(=O)c1cccnc1)c1cnc(Oc2ccccc2)nc1]

To a mixture consisting of nicotinic acid (23 mg, 0.19 mmol) and cesium carbonate (115 mg, 0.35 mmol) in tetrahydrofuran (1.5 mL) was added 2-bromo-1-(2-phenoxypyrimidin-5-yl)ethanone (Example 38, Step C, 50 mg, 0.17 mmol). The stirring mixture was heated to 40° C. for one hour, after which time some starting material had not completely dissolved and the reaction was not completed as indicated by TLC. N,N-dimethylformamide (1.5 mL) was added and the reaction was stirred an additional two hours at room temperature. The work up of Example 38, Step D was followed. The title intermediate was isolated as a dark yellow solid (31 mg, 54% yield); TLC (silica) R$_f$ 0.17, 1:1 hexanes-ethyl acetate.

Step B: Preparation of 2-phenoxy-5-(2-(pyridin-3-yl)-1H-imidazol-4-yl)pyrimidine

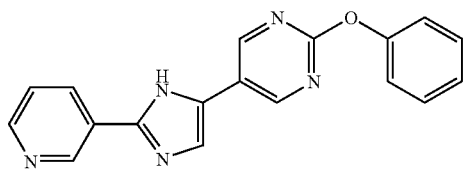 [SMILES: c1ccc(Oc2ncc(-c3cnc(-c4cccnc4)[nH]3)cn2)cc1]

The title compound was prepared according to the procedure in Example 38, Step E, except that 2-oxo-2-(2-phenoxypyrimidin-5-yl)ethyl nicotinate, prepared in Step A of this example, was used instead of 2-oxo-2-(2-phenoxypyrimidin-5-yl)ethyl benzoate. The crude brown solid was purified by flash chromatography using a 1:9 to 0:1 hexanes-ethyl acetate gradient affording the title compound (7.1 mg, 24% yield) as a tan solid; melting point 236° C.; ¹H-NMR (400 MHz; DMSO-d₆) δ 9.19 (s, 1H), 9.05 (s, 2H), 8.58-8.59 (m, 1H), 8.30-8.33 (m, 1H), 7.99 (s, 1H), 7.51-7.54 (m, 1H), 7.44-7.48 (m, 2H), 7.23-7.29 (m, 3H); LC/MS (ESI⁺) m/z 316; H-PGDS FPBA IC₅₀: 0.625 μM; H-PGDS inhibitor EIA IC₅₀: 0.37 μM.

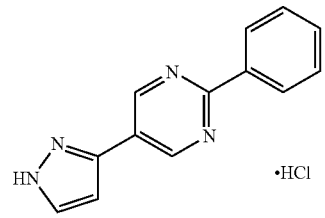 [SMILES: c1ccc(-c2ncc(-c3cc[nH]n3)cn2)cc1 ; Cl]

| Ex. | U$^1$ | U$^2$ | U$^3$ | U$^4$ | H-PGDS FPBA IC₅₀ (μM) | H-PGDS Inhibitor EIA IC₅₀ (μM) |
|---|---|---|---|---|---|---|
| 5 | NH | CH | N | CH | 5 | |
| 41 | NH | N | CH | CH | 2.4 | |
| 42 | O | CH | CH | N | 7.8 | |
| 43 | NH | N | N | N | 2.5 | |

Example 41

Preparation of 2-phenyl-5-(1H-pyrazol-3-yl)pyrimidine hydrochloride

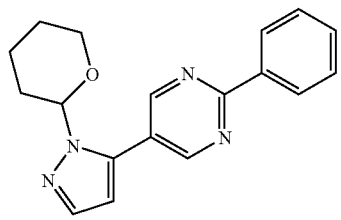 [SMILES: c1ccc(-c2ncc(-c3ccnn3C3CCCCO3)cn2)cc1]

Step A: Preparation of 2-phenyl-5-(1-(tetrahydro-2H-pyran-2-yl)-1H-pyrazol-5-yl)pyrimidine Diisopropyl 1-(tetrahydro-2H-pyran-2-yl)-1H-pyrazol-5-ylboronate (595 mg, 1.46 mmol) prepared according to the procedure described in the *Journal of Organic Chemistry*, 2008, 73, 1241-1243) was combined with Pd₂(dba)₃ (13 mg, 0.013 mmol) and 4,5-bis(diphenylphosphino)-9,9-dimethylxanthene (19 mg, 0.033 mmol). 1,4-Dioxane (10 mL) and 5-bromo-2-phenylpyrimidine (343 mg, 1.46 mmol) were added followed by 1.27 M aqueous K₃PO₄ (958 mg dissolved in 3.5 mL of water) and the mixture heated at 100° C. for 18 hours with stirring. The mixture was cooled to room temperature and filtered through Celite washing with ethyl acetate. The solvent was removed under reduced pressure and the concentrate partitioned between water and ethyl acetate. The organic phase was retained and dried with anhydrous sodium sulfate. The solution was filtered and the solvent removed under reduced pressure. Purification by silica gel flash chromatography (9:1 to 3:2 v/v hexane-ethyl acetate gradient) through a 12-g Silicycle® flash silica cartridge gave title intermediate as a white solid (51 mg, 11% yield); $R_f$ 0.70 with 40% ethyl acetate in hexane; MS (ESI$^+$) m/z 307 (M+1).

Step B: Preparation of
2-phenyl-5-(1H-pyrazol-3-yl)pyrimidine
hydrochloride

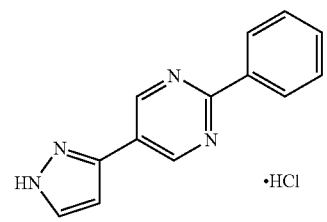 [SMILES: c1ccc(-c2ncc(-c3cc[nH]n3)cn2)cc1 ; Cl]

2-Phenyl-5-(1-(tetrahydro-2H-pyran-2-yl)-1H-pyrazol-5-yl)pyrimidine (Step A, 51 mg) was added to a 1 N hydrochloric acid solution in methanol (5 mL). The solution was stirred at room temperature for two hours. MTBE (40 mL) was added to precipitate a white solid which was filtered and rinsed with MTBE and dried under high vacuum. The title compound was obtained as a white powder (11.4 mg, 27% yield); melting point 264-273° C.; $^1$H-NMR (300 MHz; CD$_3$OD) δ 10.0 (s, 1H), 9.29 (s, 2H), 8.44 (dd, 2H), 7.86 (d, 1H), 7.54 (m, 3H), 6.95 (d, 1H); MS (ESI$^+$) m/z 223 (M+1); H-PGDS FPBA IC$_{50}$: 2.4 µM.

Example 42

Preparation of 2-(2-phenylpyrimidin-5-yl)oxazole

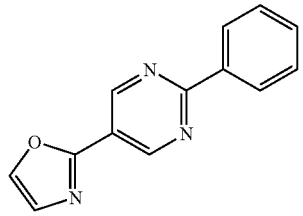 [SMILES: c1ccc(-c2ncc(-c3ncco3)cn2)cc1]

Oxazole (124 mg, 1.8 mmol) was dissolved in stirring tetrahydrofuran (20 mL) under nitrogen at −78° C. and treated with n-butyllithium (2.0 M in cyclohexane, 1.1 mL, 2.2 mmol) maintaining internal temperature below −60° C. After stirring ten minutes, ZnCl$_2$ (0.48 g, 3.5 mmol) was added portionwise. The cooling bath was removed and the solution was allowed to reach room temperature.

Tetrakis(triphenylphosphine)palladium(0) (30 mg, 5 mole %) and 5-bromo-2-phenylpyrimidine (309 mg, 1.30 mmol) were added and the mixture heated at 60° C. for four hours. Solvent was removed under reduced pressure and the mixture partitioned between saturated aqueous ammonium chloride and ethyl acetate. The organic phase was retained and additional ethyl acetate extractions of the aqueous phase performed. The combined extracts were dried with anhydrous sodium sulfate, the solution filtered, and solvent removed under reduced pressure. Purification by silica gel flash chromatography (9:1 to 7:3 v/v hexane-ethyl acetate) through a 12-g Silicycle® flash silica cartridge afforded the title compound as an off-white solid (17 mg, 6% yield); $R_f$ 0.66 with 3:1 v/v hexane-ethyl acetate; melting point 175-177° C.; $^1$H-NMR (300 MHz; DMSO-d$_6$) δ 9.42 (s, 2H), 8.48 (dd, 2H), 8.41 (s, 1H), 7.56-7.62 (m, 3H), 7.54 (s, 1H); MS (ESI$^+$) m/z 224 (M+1), (ESI$^-$) m/z 222 (M−1); H-PGDS FPBA IC$_{50}$: 7.8 µM.

Example 43

Preparation of
2-phenyl-5-(1H-tetrazol-5-yl)pyrimidine

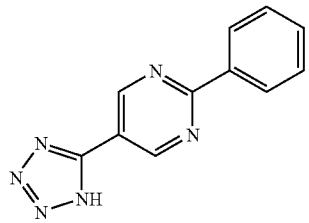 [SMILES: c1ccc(-c2ncc(-c3nnn[nH]3)cn2)cc1]

A mixture consisting of 2-phenylpyrimidine-5-carbonitrile (200 mg, 1.10 mmol), sodium azide (80 mg, 1.2 mmol) and ammonium chloride (66 mg, 1.2 mmol) in DMF (3 mL) was stirred at 100° C. for 24 hours. The reaction mixture was allowed to cool to room temperature. Upon addition of 1N hydrochloric acid (3 mL), a white solid precipitated. The precipitate was isolated by filtration and recrystallized from ethanol to afford the title compound as a white solid (123 mg, 50% yield); melting point 237° C.; $^1$H-NMR (400 MHz; DMSO-d$_6$) δ 9.51 (s, 2H), 8.51-8.53 (m, 2H), 7.61-7.65 (m, 3H); LC/MS (ESI$^+$) m/z 225; H-PGDS FPBA IC$_{50}$: 2.5 µM.

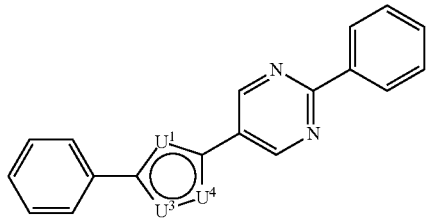

| Ex. | U$^1$ | U$^3$ | U$^4$ | H-PGDS FPBA IC$_{50}$ (µM) | H-PGDS Inhibitor EIA IC$_{50}$ (µM) |
|---|---|---|---|---|---|
| 1 | NH | N | CH | 0.25 | 0.012 |
| 44 (Step B) | NBn | CH | N | 15 | |
| 44 | NH | CH | N | 2.8 | |
| 45 | CH | N | NH | 1.5 | |
| 46 | O | N | CH | 125 | |
| 47 | O | CH | N | >20 | |
| 48 | N | S | CH | >20 | |
| 49 | NH | N | N | 1.0 | 0.084 |

Example 44

Preparation of 2-phenyl-5-(5-phenyl-1H-imidazol-2-yl)pyrimidine

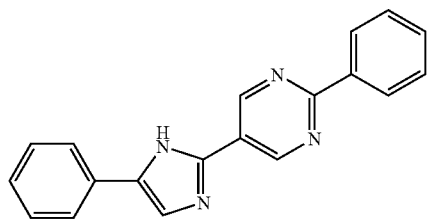 [SMILES: c1ccc(-c2ncc(-c3ncc(-c4ccccc4)[nH]3)cn2)cc1]

Step A: Preparation of 1-benzyl-5-phenyl-1H-imidazole

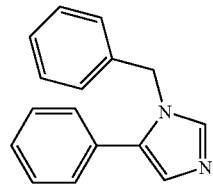 [SMILES: c1ccc(Cn2cncc2-c2ccccc2)cc1]

The title intermediate was prepared by the method described in Example 1, Step C, except that (i) commercially available bromobenzene was used instead of 5-bromo-2-phenylpyrimidine, and (ii) 1-benzyl-1H-imidazole was used instead of 1-benzyl-2-phenyl-1H-imidazole. The product was purified by flash silica column chromatography. Elution through a 25-g Silicycle® flash silica cartridge with gradient of 0% to 5% methanol in dichloromethane afforded the title intermediate as a yellow solid (0.140 g, 60% yield); $R_f$ 0.53 with 9:1 v/v dichloromethane-methanol; $^1$H-NMR (400 MHz; CDCl$_3$) δ 7.59 (s, 1H), 7.4-7.25 (m, 8H), 7.17 (s, 1H), 7.05 (d, 2H), 5.18 (s, 2H); MS (ESI$^+$) m/z 235.1 (M+1).

Step B: Preparation of 5-(1-benzyl-5-phenyl-1H-imidazol-2-yl)-2-phenylpyrimidine

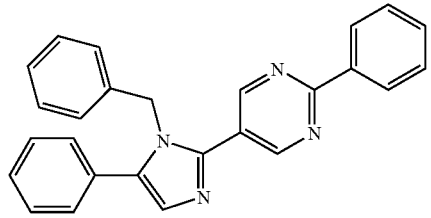 [SMILES: c1ccc(Cn2c(-c3ccccc3)cnc2-c2cnc(-c3ccccc3)nc2)cc1]

The title intermediate was prepared by the method described in Example 1, Step C, except that (i) 1-benzyl-5-phenyl-1H-imidazole was used instead of 1-benzyl-2-phenyl-1H-imidazole, (ii) copper iodide (2.0 molar equivalents) and N,N-dimethylacetamide (15 mL) was used instead of tris(2-furyl)phosphine, potassium carbonate, and N,N-dimethylformamide. The reaction mixture was brought to reflux (160° C.) under a nitrogen atmosphere overnight and then worked up in the same manner as described in Example 1, Step C to afford the title intermediate as a white solid (0.110 g, 35% yield); $R_f$ 0.66 with 95:5 v/v dichloromethane-methanol; $^1$H-NMR (400 MHz; CDCl$_3$) δ 9.00 (s, 2H), 8.43 (m, 2H), 7.58-7.23 (m, 12H), 5.35 (s, 2H); MS (ESI$^+$) m/z 389.1 (M+1); −PGDS FPBA IC$_{50}$: 15 μM.

Step C: Preparation of 2-phenyl-5-(5-phenyl-1H-imidazol-2-yl)pyrimidine

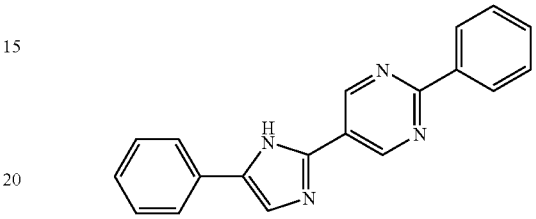

The title compound was prepared by the method described in Example 1, Step D, except that 5-(1-benzyl-5-phenyl-1H-imidazol-2-yl)-2-phenylpyrimidine (this Example, Step B) was used instead of 5-(1-benzyl-2-phenyl-1H-imidazol-5-yl)-2-phenylpyrimidine. The title compound was isolated as a white solid (0.044 g, 62% yield); $R_f$ 0.26 with 95:5 v/v dichloromethane-methanol; melting point 238° C.; $^1$H-NMR (400 MHz; DMSO-d$_6$) δ 9.40 (s, 2H), 8.43 (m, 2H), 7.99-7.84 (m, 2H), 7.58-7.20 (m, 8H); MS (ESI$^+$) m/z 299.1 (M+1); H-PGDS FPBA IC$_{50}$: 2.8 μM.

Example 45

Preparation of 2-phenyl-5-(3-phenyl-1H-pyrazol-5-yl)pyrimidine

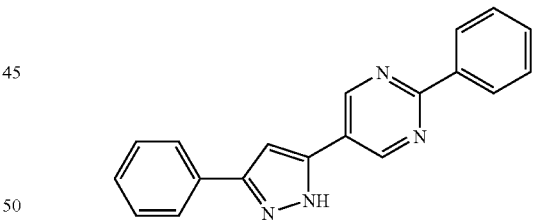

A mixture consisting of methyl 2-phenylpyrimidine-5-carboxylate (214 mg, 1.00 mmol) and acetophenone (0.115 mL, 120 mg, 1.00 mmol) in diethyl ether (10 mL) under a nitrogen atmosphere at room temperature was stirred for ten minutes. Sodium methoxide (65 mg, 1.2 mmol) was subsequently added followed by methanol (1.0 mL). The solution was stirred overnight at room temperature. The off-white precipitate which had formed was collected by filtration and was washed with diethyl ether. The solid was dissolved in water and the pH adjusted to 3 using acetic acid. A solid precipitated and was collected by filtration and washed with water. The solid was dried under high vacuum and was subsequently dissolved in acetic acid (10 mL). To this solution was added hydrazine (0.4 mL) and the mixture was stirred at room temperature overnight. The mixture was filtered and solids washed with hexane. The crude solid was purified by silica gel flash chromatography (9:1 to 1:1 v/v hexane-ethyl acetate gradient) through a 25-g Silicycle® flash silica cartridge which gave the title compound as light yellow solid (8 mg, 3% yield); $R_f$ 0.40 with 7:3 v/v hexane-ethyl acetate; $^1$H-NMR (300 MHz; CDCl$_3$) δ 9.38 (s, 2H), 8.45 (dd, 2H), 7.84 (br, 2H), 7.36-7.60 (m, 7H); MS (ESI$^+$) m/z 299 (M+1); H-PGDS FPBA IC$_{50}$: 1.5 µM.

Example 46

Preparation of 2-phenyl-5-(2-phenylpyrimidin-5-yl)oxazole

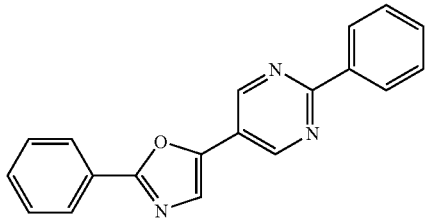 [SMILES: c1ccc(-c2ncc(-c3cnc(-c4ccccc4)o3)cn2)cc1]

Silver carbonate (317 mg, 1.15 mmol), triphenylphosphine (16 mg, 0.06 mmol) and Pd(dppf)Cl$_2$.CH$_2$Cl$_2$ (24 mg, 5 mole %) were stirred together at room temperature under nitrogen. 5-Bromo-2-phenylpyrimidine (163 mg, 0.69 mmol) was added followed by 2-phenyl-oxazole (84 mg, 0.58 mmol; prepared according to Ohnmacht, S. A. et al., *Chemical Communications*, 2008, 1241-1243). Finally water (6 mL) was added and the mixture heated for 18 hours at 60° C. The mixture was cooled to room temperature and filtered through Celite washing with DCM and acetone. Purification by silica gel flash chromatography (100% DCM) through a 12-g Silicycle® flash silica cartridge gave title compound as light yellow solid (19 mg, 11% yield); $R_f$ 0.68 with DCM; melting point 228-231° C.; $^1$H-NMR (300 MHz; DMSO-d$_6$) δ 9.39 (s, 2H), 8.45 (dd, 2H), 8.17 (dd, 2H), 8.11 (s, 1H), 7.54-7.65 (m, 6H); MS (ESI$^+$) m/z 300 (M+1), (ESI$^-$) m/z 298 (M−1); H-PGDS FPBA IC$_{50}$: 125 µM.

Example 47

Preparation of 5-phenyl-2-(2-phenylpyrimidin-5-yl)oxazole

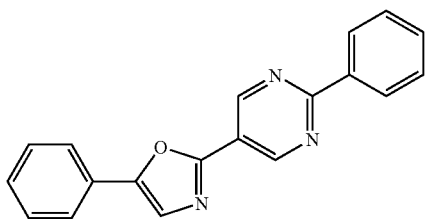 [SMILES: c1ccc(-c2ncc(-c3ncc(-c4ccccc4)o3)cn2)cc1]

Step A: Preparation of N-(2-oxo-2-phenylethyl)-2-phenylpyrimidine-5-carboxamide

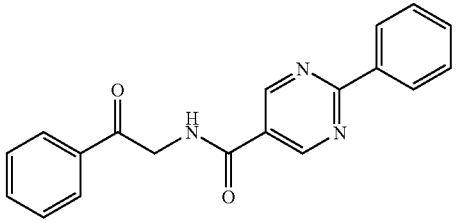 [SMILES: O=C(CNC(=O)c1cnc(-c2ccccc2)nc1)c1ccccc1]

To a solution consisting of 2-phenylpyrimidine-5-carboxylic acid (200 mg, 1.0 mmol) in thionyl chloride (10 mL) was added one drop of dry DMF. The solution was heated to reflux for four hours and was subsequently allowed to reach room temperature. Thionyl chloride was evaporated away under reduced pressure and to the residue was added toluene (2×30 mL), which was evaporated and the residue subjected to high vacuum to remove residual thionyl chloride. The residue and 2-amino-1-phenylethanone hydrochloride (172 mg, 1.0 mmol) were dissolved in dichloromethane (10 mL) followed by triethylamine (0.28 mL). The solution was stirred at room temperature for 18 hours. The mixture was diluted with dichloromethane and was washed with water. The organic phase was dried with anhydrous sodium sulfate, filtered, and concentrated. The residue was recrystallized from ethyl acetate to afford title intermediate as a white solid (183 mg, 57% yield); $R_f$ 0.60 with 5% methanol in dichloromethane; $^1$H-NMR (300 MHz; DMSO-d$_6$) δ 9.33 (s, 2H), 8.48 (d, 2H), 8.07 (d, 2H), 7.70 (brt, 1H), 7.59 (m, 6H), 4.89 (d, 2H); MS (ESI$^-$) m/z 316 (M−1).

Step B: Preparation of 5-Phenyl-2-(2-phenylpyrimidin-5-yl)oxazole

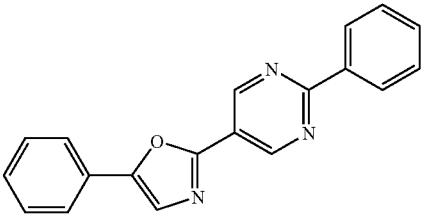 [SMILES: c1ccc(-c2ncc(-c3ncc(-c4ccccc4)o3)cn2)cc1]

To a solution consisting of N-(2-oxo-2-phenylethyl)-2-phenylpyrimidine-5-carboxamide (Step A, 80 mg, 0.25 mmol) in POCl$_3$ (1.0 mL) was added pyridine (2.0 mL). The solution was heated at 70° C. for six hours and was subsequently allowed to cool to room temperature. The solution was diluted with ethyl acetate (10 mL) and poured into a chilled saturated aqueous sodium bicarbonate solution (40 mL). After stirring for 15 minutes, the mixture was extracted with ethyl acetate (3×25 mL) and the combined organics were dried with anhydrous sodium sulfate, filtered, and concentrated. The residue was purified by silica gel flash chromatography (0-5% methanol in dichloromethane gradient) through a 40-g Silicycle® flash silica cartridge to afford the title compound as an off-white solid (49 mg, 65% yield); $R_f$ 0.80 with 2% methanol in dichloromethane; $^1$H-NMR (300 MHz; DMSO-d$_6$) δ 9.52 (s, 2H), 8.48 (dd, 2H), 7.99 (s, 1H), 7.94 (dd, 2H), 7.43-7.60 (m, 6H); MS (ESI+) m/z 300 (M+1); H-PGDS FPBA IC$_{50}$: >20 μM.

Example 48

Preparation of
2-phenyl-4-(2-phenylpyrimidin-5-yl)thiazole

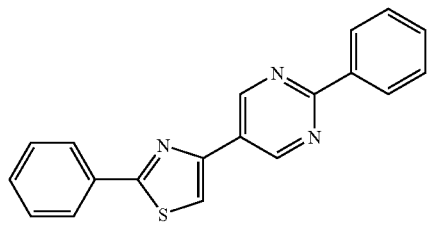 [SMILES: c1ccc(-c2ncc(-c3csc(-c4ccccc4)n3)cn2)cc1]

A mixture consisting of 2-bromo-1-(2-phenylpyrimidin-5-yl)ethanone (Example 14, Step B, 50 mg, 0.18 mmol), thiobenzamide (TCI America, 25 mg, 0.18 mmol) and absolute ethanol (4 mL) in a capped scintillation vial was heated to near boiling for several minutes and was subsequently allowed to cool to room temperature. A white solid precipitated within minutes. The precipitate was collected by vacuum filtration. Light ethanol rinse, suction, and drying under high vacuum at room temperature afforded the title compound (26 mg, 46% yield) as an off-white solid; melting point 214.4-216.1° C.; $^1$H-NMR (400 MHz; DMSO-d$_6$) δ 9.54 (s, 2H), 8.54 (s, 1H), 8.47 (m, 2H), 8.08 (m, 2H), 7.62-7.54 (m, 6H); LC/MS (ESI+) m/z 316.1, (ESI−) m/z 337.2 (M−1+Na+); H-PGDS FPBA IC$_{50}$: >20 μM.

Triazole compounds of general structure 25 of the exemplary embodiments may be prepared according to the general synthetic route illustrated in Scheme 7. Examples 49 and 50 may be prepared using this general route.

Scheme 7: General synthesis of 5-(triazol-4-yl)-pyridines and 5-(triazol-4-yl)-pyrimidines

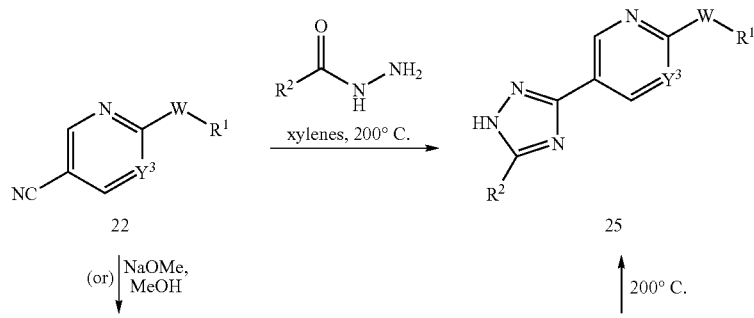

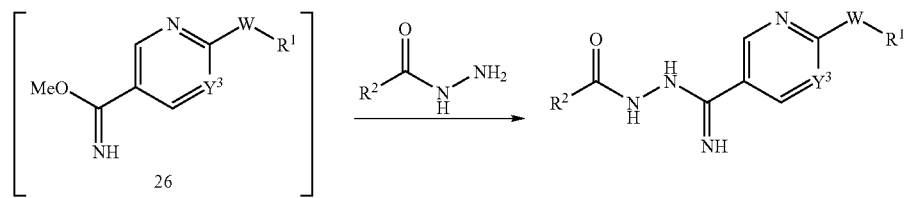

R$^1$, R$^2$, Y$^3$ and W are defined in the detailed description

Example 49

Preparation of 2-phenyl-5-(5-phenyl-4H-1,2,4-triazol-3-yl)pyrimidine

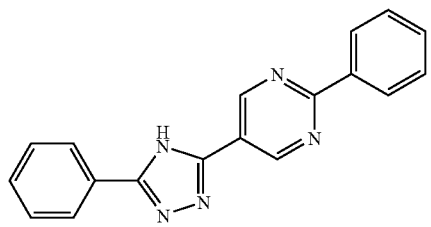 [SMILES: c1ccc(-c2ncc(-c3nnc(-c4ccccc4)[nH]3)cn2)cc1]

2-Phenyl-pyrimidine-5-carbonitrile (Biofine International, 0.10 g, 0.55 mmol) and benzoic hydrazide (Aldrich, 0.075 g, 0.55 mmol) were dissolved in o-xylene (5 mL) and heated to 200° C. in a sealed pressure tube while stirring for 24 hours. After cooling to room temperature, the reaction mixture was heated to 200° C. in an open vessel under a stream of nitrogen for six hours. The remaining crude solid was dissolved in a minimal amount of 98:2 v/v dichloromethane-methanol and purified by flash silica column chromatography. Elution through a 40-g Analogix® flash silica cartridge with 100% dichloromethane to 2% methanol in dichloromethane afforded the title compound as a pale yellow solid (10 mg, 6% yield); $R_f$ 0.1 with 98:2 v/v dichloromethane-methanol; melting point 280-282° C.; $^1$H-NMR (400 MHz; CDCl$_3$) δ 8.48-8.42 (m, 2H), 8.12-8.06 (m, 2H), 7.60-7.48 (m, 6H); MS (ESI$^+$) m/z 300.1 (M+1); H-PGDS FPBA IC$_{50}$: 1.0 μM; H-PGDS inhibitor EIA IC$_{50}$: 0.084 μM.

Example 50

Preparation of 2-phenyl-5-(5-(pyridin-3-yl)-1H-1,2,4-triazol-3-yl)pyrimidine

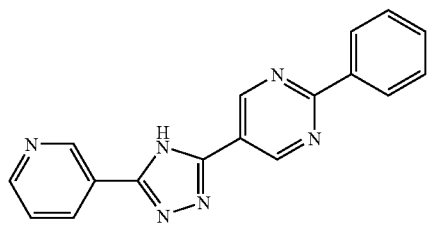 [SMILES: c1ccc(-c2ncc(-c3nnc(-c4cccnc4)[nH]3)cn2)cc1]

2-Phenyl-pyrimidine-5-carbonitrile (Biofine International, 0.20 g, 1.10 mmol) and nicotinic hydrazide (Aldrich, 0.151 g, 1.10 mmol) were dissolved in o-xylene (5 mL) and heated to 200° C. under nitrogen atmosphere for seven hours as the o-xylene slowly boiled off. The remaining crude solid was dissolved in a minimal amount of 98:2 v/v dichloromethane-methanol and purified by flash silica column chromatography. Elution through a 40-g Analogix® flash silica cartridge with 100% dichloromethane to 5% methanol in dichloromethane afforded the title compound as a yellow solid (32 mg, 10% yield); $R_f$ 0.27 with 95:5 v/v dichloromethane-methanol; melting point 322-333° C.; $^1$H-NMR (400 MHz; CDCl$_3$) δ 9.53 (s, 2H), 9.32 (d, 1H), 8.76-8.75 (m, 1H), 8.53-8.46 (m, 3H), 7.64-7.60 (m, 4H); MS (ESI$^+$) m/z 301.1 (M+1); H-PGDS FPBA IC$_{50}$: 1 μM.

Example 51

Preparation of 5-(1-methyl-5-(pyridin-3-yl)-1H-1,2,4-triazol-3-yl)-2-phenylpyrimidine

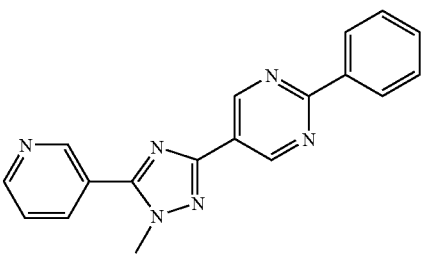 [SMILES: Cn1nc(-c2cnc(-c3ccccc3)nc2)nc1-c1cccnc1]

2-Phenyl-5-(5-(pyridin-3-yl)-1H-1,2,4-triazol-3-yl)pyrimidine (25 mg, 0.08 mmol) was dissolved in DMF (2 mL). An excess of sodium hydride (150 mg, 60% dispersion in mineral oil) and an excess of iodomethane (1 mL) were added and the solution was stirred at room temperature for 2.5 hours. The reaction was quenched by the addition of water, diluted with ethyl acetate, and washed sequentially with water and brine. The crude residue was dissolved in a minimal amount of dichloromethane and purified by flash silica column chromatography. Elution through a 12-g Analogix® flash silica cartridge with 100% dichloromethane to 4% methanol in dichloromethane afforded the title compounds (2 mg, 8% yield); $R_f$ 0.33 with 95:5 v/v dichloromethane-methanol; MS (ESI$^+$) m/z 315.1 (M+1).

Example 52

Preparation of tert-butyl 4-(5-(2-phenylpyrimidin-5-yl)-2H-tetrazol-2-yl)piperidine-1-carboxylate

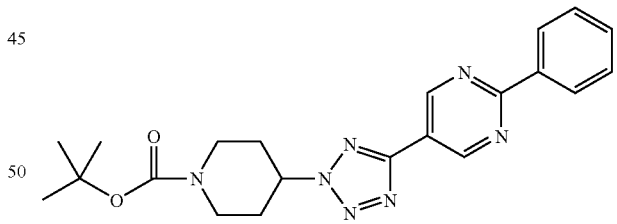

To a solution consisting of 2-phenyl-5-(2H-tetrazol-5-yl)pyrimidine (25 mg, 0.111 mmol) in DMF (2.0 mL) was added tert-butyl 4-(tosyloxy)piperidine-1-carboxylate (40 mg, 0.111 mmol), synthesized from tert-butyl 4-hydroxypiperidine-1-carboxylate (PCT International Application No. WO 2007/060026), and sodium carbonate (85 mg, 0.45 mmol). The suspension was vigorously stirred for 24 hours and an additional molar equivalent of tert-butyl 4-(tosyloxy)piperidine-1-carboxylate was added and the reaction was heated for another 24 hours at 70° C. After cooling to room temperature, the crude reaction mixture was diluted with ethyl acetate, washed sequentially with 1 M sodium carbonate, 5% citric acid, and brine. After solvent evaporation, the remaining crude solid was dissolved in a minimal amount of dichloromethane and purified by flash silica column chromatography. Elution through a 40-g Analogix® flash silica cartridge with 100% dichloromethane to 2% methanol in dichloromethane provided the title compound as an off-white solid. The solid was further purified by triturating with methanol to afford the title compound as a white solid (15 mg, 33% yield); $R_f$ 0.37 with 95:2 v/v dichloromethane-methanol; melting point 178-180° C.; $^1$H-NMR (400 MHz; CDCl$_3$) δ 9.47 (s, 2H), 8.52-8.49 (m, 2H), 7.52-7.50 (m, 3H), 4.96-4.95 (m, 2H), 4.23 (bs, 2H), 3.10-2.97 (m, 2H), 2.30-2.21 (m, 4H), 1.48 (s, 9H); MS (ESI$^+$) m/z 408.2 (M+1).

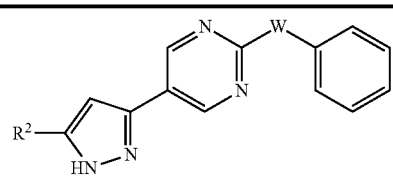

| Ex. | R$^2$ | W | H-PGDS FPBA IC$_{50}$ (μM) | H-PGDS Inhibitor EIA IC$_{50}$ (μM) |
|---|---|---|---|---|
| 41 | H | bond | 2.4 | |
| 45 | Ph | bond | 1.5 | |
| 53 | 3-pyridyl | bond | 1.3 | |
| 54 | CO$_2$Et | O | 1.3 | 0.13 |
| 55 | CO$_2$Me | O | 2 | |
| 56 | CO$_2$H | O | 5 | |
| 57 | 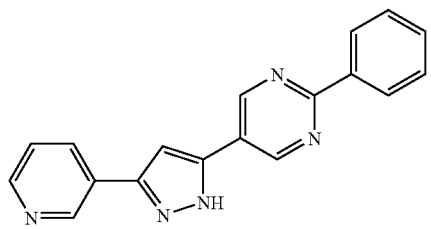 | O | 0.65 | 0.42 |

Example 53

Preparation of 2-phenyl-5-(3-(pyridin-3-yl)-1H-pyrazol-5-yl)pyrimidine

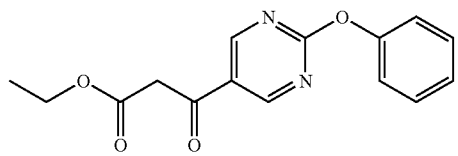

To a solution consisting of 1-(2-phenylpyrimidin-5-yl)ethanone (Example 14, Step A, 46 mg, 0.23 mmol) and methyl nicotinate (35 mg, 0.25 mmol) in tetrahydrofuran (1 mL) was added a solution consisting of potassium tert-butoxide in tetrahydrofuran (0.28 mL, 0.28 mmol). The reaction mixture was stirred overnight. Analysis of the reaction mixture by TLC (1:3 ethyl acetate-hexanes) showed the 1-(2-phenylpyrimidin-5-yl)ethanone was not consumed. To the reaction mixture was added methyl nicotinate (118 mg, 0.86 mmol) and sodium hydride (10 mg, 0.23 mmol, 60% dispersion), and the reaction mixture was heated at 50° C. for one hour. The reaction mixture was diluted with a saturated aqueous solution of ammonium chloride and sodium chloride and the organic material was extracted three times with ethyl acetate. The combined organic phase was dried over magnesium sulfate, filtered and concentrated to dryness to provide a crude material. To a solution consisting of this crude material in acetic acid was added excess hydrazine hydrate and the reaction mixture was heated at 50° C. for two hours followed by 80° C. overnight. The reaction mixture was diluted with saturated aqueous sodium bicarbonate and the organic material was extracted three times with ethyl acetate. The combined organic phase was dried over magnesium sulfate, filtered, and concentrated to dryness. The crude material was chromatographed on silica (4 g) eluted with 1:4:5 v/v dichloromethane-ethyl acetate-hexane to 1:6:4 to afford the title compound (10 mg) as a tan solid; H-PGDS FPBA IC$_{50}$: 1.3 μM.

Example 54

Preparation of ethyl 5-(2-phenoxypyrimidin-5-yl)-1H-pyrazole-3-carboxylate

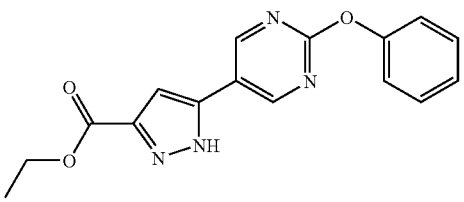 [SMILES: CCOC(=O)c1cc(-c2cnc(Oc3ccccc3)nc2)[nH]n1]

Step A: Preparation of ethyl 3-oxo-3-(2-phenoxypyrimidin-5-yl)propanoate

A mixture consisting of 1-(2-phenoxypyrimidin-5-yl)ethanone (Example 38, Step B, 214 mg, 1.00 mmol) and diethyl oxalate (0.14 mL, 150 mg, 1.0 mmol) in diethyl ether (10 mL) under a nitrogen atmosphere at room temperature was stirred for ten minutes. Sodium methoxide (65 mg, 1.2 mmol) was subsequently added followed by methanol (1.0 mL). The solution was stirred overnight at room temperature. The off-white precipitate which had formed was collected by filtration and washed with diethyl ether. The solid was dissolved in water and the pH adjusted to 3 using acetic acid. The solid precipitate which formed was filtered and washed with water. The solid was air dried to afford a mixture comprising both the ethyl and methyl esters.

Step B: Preparation of ethyl 5-(2-phenoxypyrimidin-5-yl)-1H-pyrazole-3-carboxylate

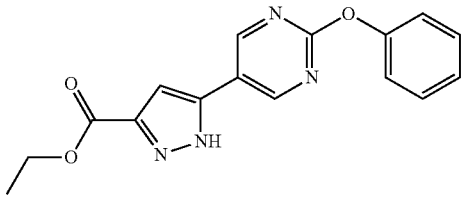 [SMILES: CCOC(=O)c1cc(-c2cnc(Oc3ccccc3)nc2)[nH]n1]

To a mixture consisting of the solid comprising ethyl 3-oxo-3-(2-phenoxypyrimidin-5-yl)propanoate (Step A, 1.00 mmol theory) in acetic acid (10 mL) was added hydrazine (0.40 mL, 410 mg, 13 mmol). The stirring mixture was heated to 60° C. for one hour and was subsequently cooled to room temperature and stirred overnight. The off-white solid which had precipitated was collected by filtration and washed with hexane. The solid was purified by silica gel flash chromatography using a 9:1 to 1:1 v/v hexane-ethyl acetate gradient through a 40-g Silicycle® flash silica cartridge to afford the title compound as a white solid (100 mg, 32% yield); $R_f$ 0.50 with 1:1 v/v hexane-ethyl acetate; $^1$H-NMR (300 MHz; DMSO-$d_6$) δ 9.12 (s, 2H), 7.50 (s, 1H), 7.43 (dd, 2H), 7.20-7.28 (m, 3H), 4.26 (q, 2H), 1.25 (t, 3H); MS (ESI$^-$) m/z 309 (M−1); H-PGDS FPBA IC$_{50}$: 1.3 µM; H-PGDS inhibitor EIA IC$_{50}$: 0.13 µM.

Example 55

Preparation of methyl 5-(2-phenoxypyrimidin-5-yl)-1H-pyrazole-3-carboxylate

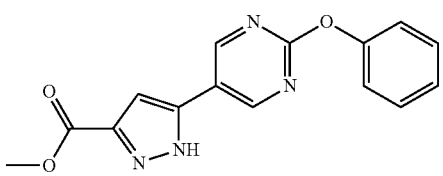 [SMILES: COC(=O)c1cc(-c2cnc(Oc3ccccc3)nc2)[nH]n1]

The title compound was isolated from the chromatography of Example 54, Step B as white solid (52 mg, 17% yield); $R_f$ 0.40 with 1:1 v/v hexane-ethyl acetate; $^1$H-NMR (300 MHz; DMSO-$d_6$) δ 9.08 (s, 2H), 7.50 (s, 1H), 7.46 (dd, 2H), 7.20-7.30 (m, 3H), 3.90 (s, 3H); MS (ESI$^-$) m/z 309 (M−1); H-PGDS FPBA IC$_{50}$: 2 µM.

Example 56

Preparation of 5-(2-phenoxypyrimidin-5-yl)-1H-pyrazole-3-carboxylic acid

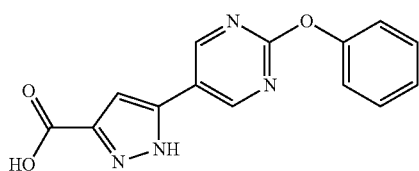 [SMILES: O=C(O)c1cc(-c2cnc(Oc3ccccc3)nc2)[nH]n1]

To a solution consisting of lithium hydroxide monohydrate (0.13 g, 3.0 mmol) dissolved in ethanol (10 mL)/water (5 mL) was added ethyl 5-(2-phenoxypyrimidin-5-yl)-1H-pyrazole-3-carboxylate (Example 54, 90 mg, 0.29 mmol) and the mixture was stirred at room temperature for 18 hours. Ethanol was removed under reduced pressure and the solution diluted with water and subsequently was acidified with acetic acid to precipitate product. The solid precipitate was filtered, washed with water, and dried under high vacuum to afford the title compound as a white solid (64 mg, 79% yield); $R_f$ 0.15 with 2% methanol in dichloromethane; $^1$H-NMR (300 MHz; DMSO-$d_6$) δ 9.12 (s, 2H), 7.49 (dd, 2H), 7.25-7.43 (m, 4H); MS (ESI$^-$) m/z 281 (M−1); H-PGDS FPBA IC$_{50}$: 5 µM.

Example 57

Preparation of (4-methylpiperazin-1-yl)(5-(2-phenoxypyrimidin-5-yl)-1H-pyrazol-3-yl)methanone

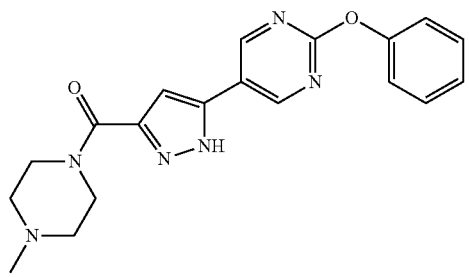 [SMILES: CN1CCN(C(=O)c2cc(-c3cnc(Oc4ccccc4)nc3)[nH]n2)CC1]

To a solution consisting of 5-(2-phenoxypyrimidin-5-yl)-1H-pyrazole-3-carboxylic acid (Example 56, 60 mg, 0.21 mmol) in thionyl chloride (10 mL) was added one drop of dry DMF. The solution was heated to reflux for four hours and was subsequently allowed to cool to room temperature. Thionyl chloride was evaporated under reduced pressure and to the residue was added toluene (2×30 mL), which was evaporated and the residue subjected to high vacuum to remove residual thionyl chloride. The residue and 1-methylpiperazine (25 mg, 0.028 mL, 0.25 mmol) were dissolved in dichloromethane (10 mL) followed by the addition of triethylamine (0.14 mL). The solution was stirred at room temperature for 18 hours. The solvent was evaporated and the residue was purified by silica gel flash chromatography using 0-10% methanol in dichloromethane gradient through a 25-g Silicycle® flash silica cartridge to afford the title compound as a white solid (46 mg, 60% yield); $R_f$ 0.30 with 6% methanol in dichloromethane; $^1$H-NMR (300 MHz; CD$_3$OD) δ 8.96 (s, 2H), 7.43 (m, 2H), 7.25 (m, 1H), 7.19 (d, 2H), 7.02 (s, 1H), 3.74-3.99 (br, 4H), 2.51 (br, 4H), 2.33 (s, 3H); MS (ESI$^-$) m/z 363 (M−1); H-PGDS FPBA IC$_{50}$: 0.65 µM; H-PGDS inhibitor EIA IC$_{50}$: 0.42 µM.

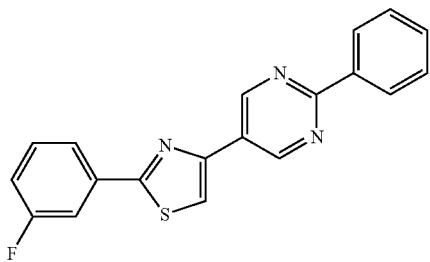 [SMILES: Fc1cccc(-c2nc(-c3cnc(-c4ccccc4)nc3)cs2)c1]

| Ex. | R² | H-PGDS FPBA IC₅₀ (μM) | H-PGDS Inhibitor EIA IC₅₀ (μM) |
|---|---|---|---|
| 48 | Ph | >20 | |
| 58 | 3-F-Ph | >20 | |
| 59 | 3-pyridyl | 1 | 0.15 |
| 60 | PhCH₂— | >20 | |
| 61 | 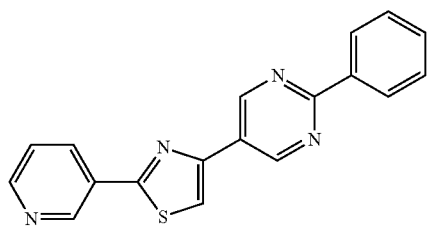 •CF₃CO₂H | 5 | |

Example 58

Preparation of 2-(3-fluorophenyl)-4-(2-phenylpyrimidin-5-yl)thiazole

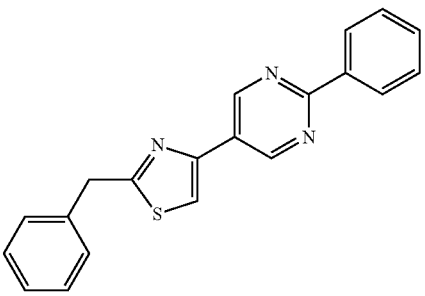 [SMILES: c1ccc(Cc2nc(-c3cnc(-c4ccccc4)nc3)cs2)cc1]

The title compound was prepared according to the procedure described in Example 48 except that 3-fluorothiobenzamide was used instead of thiobenzamide. The title compound was isolated (35.4 mg, 59% yield) as a white solid; melting point 228° C.; ¹H-NMR (400 MHz; DMSO-d₆) δ 8.62 (s, 2H), 8.48-8.53 (m, 3H), 7.94-8.01 (m, 2H), 7.58-7.70 (m, 4H), 7.42-7.48 (m, 1H); LC/MS (ESI⁺) m/z 334; H-PGDS FPBA IC₅₀: >20 μM.

Example 59

Preparation of 4-(2-phenylpyrimidin-5-yl)-2-(pyridin-3-yl)thiazole

The title compound was prepared according to the procedure described in Example 48 except that thionicotinamide was used instead of thiobenzamide. The title compound was isolated (30.2 mg, 53% yield) as an off-white solid; melting point 319° C.; ¹H-NMR (400 MHz; DMSO-d₆) δ 9.39 (s, 2H), 9.38 (s, 1H), 8.81-8.84 (m, 1H), 8.69 (s, 1H), 8.59-8.64 (m, 1H), 8.48-8.54 (m, 2H), 7.72-7.77 (m, 1H), 7.59-7.64 (m, 3H); LC/MS (ESI⁺) m/z 317; H-PGDS FPBA IC₅₀: 1 μM; H-PGDS inhibitor EIA IC₅₀: 0.15 μM.

Example 60

Preparation of 2-benzyl-4-(2-phenylpyrimidin-5-yl)thiazole

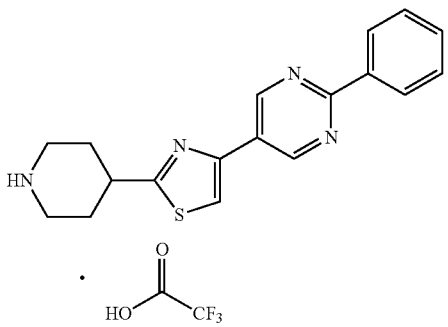

The title compound was prepared according to the procedure described in Example 48 except that 2-phenylthioacetamide was used instead of thiobenzamide. The title compound was isolated (26 mg, 51% yield) as a pale yellow solid; melting point 170° C.; ¹H-NMR (400 MHz; DMSO-d₆) δ 9.45 (s, 2H), 8.45-8.50 (m, 2H), 8.36 (s, 1H), 7.57-7.62 (m, 3H), 7.31-7.48 (m, 5H), 4.50 (s, 2H); LC/MS (ESI+) m/z 330; H-PGDS FPBA IC₅₀: >20 μM.

Example 61

Preparation of 4-(4-(2-phenylpyrimidin-5-yl)thiazol-2-yl)piperidinium 2,2,2-trifluoroacetate

Step A: Preparation of tert-butyl 4-(4-(2-phenylpyrimidin-5-yl)thiazol-2-yl)piperidine-1-carboxylate

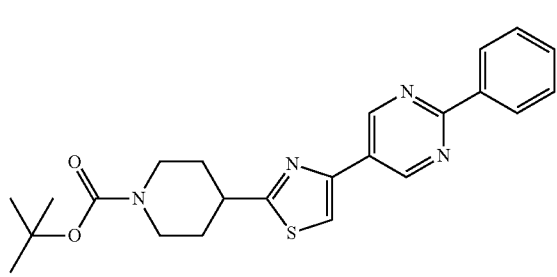 [SMILES: CC(C)(C)OC(=O)N1CCC(c2nc(-c3cnc(-c4ccccc4)nc3)cs2)CC1]

The title intermediate was prepared according to the procedure described in Example 48 except that tert-butyl 4-(aminocarbothioyl)tetrahydropyridine-1(2H)-carboxylate was used instead of thiobenzamide. The product was isolated (27 mg) as an off-white solid; LC/MS shows a mixture of title intermediate ((ESI$^+$) m/z 423) and title (deprotected) compound ((ESI$^+$) m/z 323).

Step B: Preparation of 4-(4-(2-phenylpyrimidin-5-yl)thiazol-2-yl)piperidinium 2,2,2-trifluoroacetate

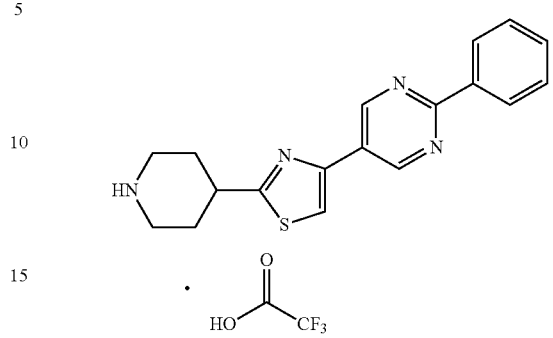

A mixture consisting of title intermediate (23 mg) and trifluoroacetic acid (500 µL) was stirred at room temperature for 20 minutes. The trifluoroacetic acid was removed yielding an off-white oil. Trituration with ethanol produced an off-white solid which was subsequently filtered and washed with ethanol to afford the title compound (23.5 mg, 85% yield) as a white solid; melting point 290° C.; $^1$H-NMR (400 MHz; DMSO-d$_6$) δ 9.50 (s, 2H), 8.50-8.58 (m, 2H), 8.45 (s, 1H), 7.60-7.65 (m, 3H), 3.32-3.59 (m, 4H), 3.08-3.20 (m, 2H), 2.30-2.39 (m, 2H), 1.94-2.07 (m, 2H); LC/MS (ESI$^+$) m/z 323; H-PGDS FPBA IC$_{50}$: 5 µM.

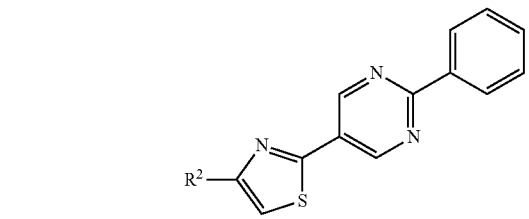

| Ex. | R$^2$ | H-PGDS FPBA IC$_{50}$ (µM) | H-PGDS Inhibitor EIA IC$_{50}$ (µM) |
|---|---|---|---|
| 62 | CO$_2$$^t$Bu | 5.9 | |
| 63 | CO$_2$H | 1.1 | |
| 64 | 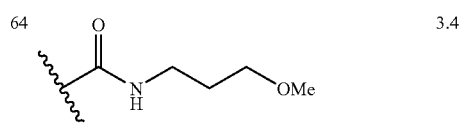 | 3.4 | |
| 65 | 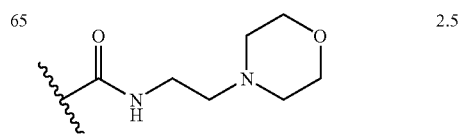 | 2.5 | |

Example 62

Preparation of 2 tert-butyl 2-(2-phenylpyrimidin-5-yl)thiazole-4-carboxylate

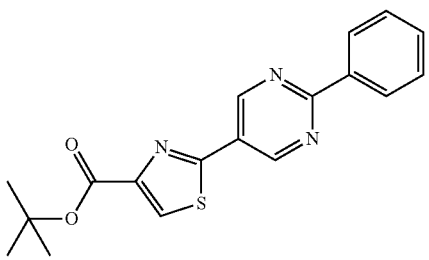 [SMILES: CC(C)(C)OC(=O)c1csc(-c2cnc(-c3ccccc3)nc2)n1]

In a sealed tube, cesium carbonate (1.95 g, 6.00 mmol), tert-butyl-4-thiazolecarboxylate (556 mg, 3.00 mmol; prepared according to the procedure described in *Organic Letters*, 2008, 10(13), 2909), palladium(II) acetate (47 mg, 0.21 mmol) and 4,5-bis(diphenylphosphino)-9,9-dimethylxanthene (240 mg, 0.42 mmol) were combined with 5-bromo-2-phenylpyrimidine (705 mg, 3.00 mmol) in dry DMF (11 mL) and the mixture heated at 110° C. for 18 hours with stirring. The mixture was cooled to room temperature and filtered through Celite washing with hot ethyl acetate. Solvent was removed under reduced pressure and the residue purified by silica gel flash chromatography (9:1 to 3:2 v/v hexane-ethyl acetate gradient) through a 40-g Silicycle® flash silica cartridge. The title compound was obtained as a white solid (646 mg, 63% yield); $R_f$ 0.75 with 1:1 v/v hexane-ethyl acetate; $^1$H-NMR (300 MHz; CDCl$_3$) δ 9.37 (s, 2H), 8.52 (dd, 2H), 8.15 (s, 1H), 7.54 (m, 3H), 1.64 (s, 9H); MS (ESI$^+$) m/z 340 (M+1); H-PGDS FPBA IC$_{50}$: 5.9 μM.

Example 63

Preparation of 2-(2-Phenylpyrimidin-5-yl)thiazole-4-carboxylic acid

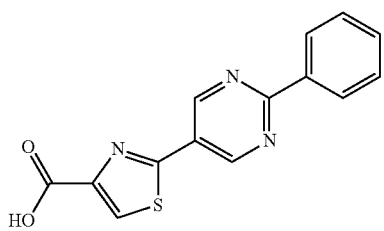 [SMILES: O=C(O)c1csc(-c2cnc(-c3ccccc3)nc2)n1]

To a solution consisting of lithium hydroxide monohydrate (0.38 g, 9.0 mmol) dissolved in ethanol (20 mL)/water (10 mL) was added tert-butyl 2-(2-phenylpyrimidin-5-yl)thiazole-4-carboxylate (Example 62, 705 mg, 3.0 mmol) in dry DMF (11 mL) and the mixture stirred at room temperature for 18 hours. Ethanol was removed under reduced pressure and the solution diluted with water and subsequently extracted with diethyl ether (2×30 mL). The aqueous phase was acidified with 2 N hydrochloric acid to pH2. The solid precipitate was filtered, washed with water and dried under high vacuum to give the title compound as an off-white solid (371 mg, 87% yield); $R_f$ 0.15 with 9:1 v/v dichloromethane-methanol; $^1$H-NMR (300 MHz; DMSO-d$_6$) δ 9.39 (s, 2H), 8.63 (s, 1H), 8.44 (dd, 2H), 7.55 (m, 3H); MS (ESI$^+$) m/z 284 (M+1); H-PGDS FPBA IC$_{50}$: 1.1 μM.

Example 64

Preparation of N-(3-methoxypropyl)-2-(2-phenylpyrimidin-5-yl)thiazole-4-carboxamide

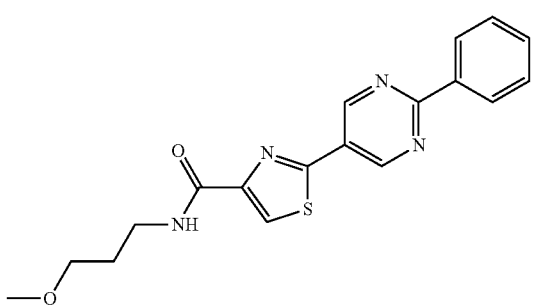 [SMILES: COCCCNC(=O)c1csc(-c2cnc(-c3ccccc3)nc2)n1]

To a solution consisting of 2-(2-phenylpyrimidin-5-yl)thiazole-4-carboxylic acid (Example 63, 80 mg, 0.28 mmol) in dichloromethane (10 mL) was added EDAC (75 mg, 0.39 mmol) and HOBt (53 mg, 0.39 mmol) at 0° C. To this mixture was added 3-methoxypropylamine (25 mg, 0.28 mmol) dissolved in dichloromethane (2 mL) and diisopropylethylamine (0.52 mL, 390 mg, 3.0 mmol). The solution was allowed to reach room temperature and stirred for 18 hours. The solvent was evaporated away under reduced pressure and the residue was purified by silica gel flash chromatography (1:1 v/v hexane-ethyl acetate to 100% ethyl acetate gradient) through a 25-g Silicycle® flash silica cartridge. The title compound was obtained as an off-white solid (21 mg, 21% yield); $R_f$ 0.70 with 4:1 v/v ethyl acetate-hexane; melting point 134-136° C.; $^1$H-NMR (300 MHz; CDCl$_3$) δ 9.31 (s, 2H), 8.52 (dd, 2H), 8.20 (s, 1H), 7.88 (br t, 1H), 7.53 (m, 3H), 3.62 (t, 2H); 3.59 (t, 2H); 3.41 (s, 3H), 1.96 (m, 2H); MS (ESI$^+$) m/z 355 (M+1); H-PGDS FPBA IC$_{50}$: 3.4 μM.

Example 65

Preparation of N-(2-morpholinoethyl)-2-(2-phenylpyrimidin-5-yl)thiazole-4-carboxamide

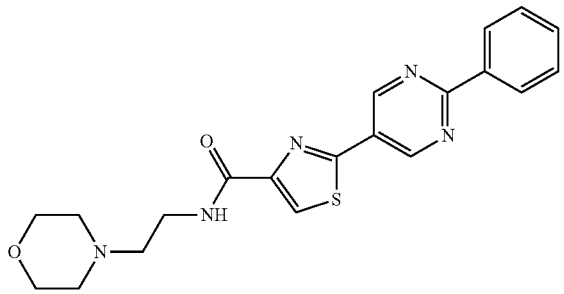 [SMILES: O=C(NCCN1CCOCC1)c1csc(-c2cnc(-c3ccccc3)nc2)n1]

To a solution consisting of 2-(2-phenylpyrimidin-5-yl)thiazole-4-carboxylic acid (Example 63, 172 mg, 0.61 mmol) in thionyl chloride (10 mL) was added one drop of dry DMF. The solution was heated at reflux for four hours and was subsequently allowed to reach room temperature and stirred for 18 hours. The thionyl chloride was evaporated away under reduced pressure and to the residue was added toluene (2×30 mL), which was evaporated and the residue subjected to high vacuum to remove residual thionyl chloride. The residue was dissolved in dichloromethane (10 mL) and 4-(2-aminoethyl) morpholine (51 mg, 0.051 mL, 0.40 mmol) was added followed by diisopropylethylamine (0.10 mL). The solution was stirred at room temperature for 18 hours. The solvent was removed under reduced pressure and the residue partitioned between water and diethyl ether. The organics were dried with anhydrous sodium sulfate, filtered, and concentrated. The residue was purified by silica gel flash chromatography (100% dichloromethane to 9:1 v/v dichloromethane-methanol gradient) through a 40-g Silicycle® flash silica cartridge. The title compound was obtained as an off-white solid (63 mg, 61% yield); $R_f$ 0.70 with 9:1 v/v dichloromethane-methanol; $^1$H-NMR (300 MHz; CDCl$_3$) δ 9.30 (s, 2H), 8.51 (m, 2H), 8.20 (s, 1H), 7.88 (br t, 1H), 7.53 (m, 3H), 3.77 (t, 4H); 3.61 (dt, 2H), 2.64 (t, 2H), 2.54 (t, 4H); MS (ESI$^+$) m/z 396 (M+1); H-PGDS FPBA IC$_{50}$: 2.5 µM.

Example 66

Preparation of 2-methyl-5-(2-(pyridin-3-yl)-1H-imidazol-5-yl)pyridine

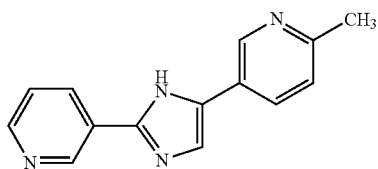 [SMILES: Cc1ccc(-c2cnc(-c3cccnc3)[nH]2)cn1]

Step A: Preparation of 5-(1-benzyl-2-(pyridin-3-yl)-1H-imidazol-5-yl)-2-methylpyridine

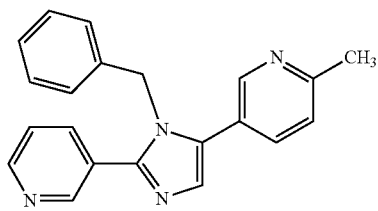 [SMILES: Cc1ccc(-c2cnc(-c3cccnc3)n2Cc2ccccc2)cn1]

To a mixture consisting of 5-bromo-2-methylpyridine (Chem-Impex, 0.132 g, 0.770 mmol), palladium (II) acetate (Strem, 0.022 g, 0.032 mmol), tris(2-furyl)phosphine (TCI America, 0.015 g, 0.064 mmol) and potassium carbonate (0.177 g, 1.283 mmol) was added a solution consisting of 3-(1-benzyl-1H-imidazol-2-yl)pyridine (0.151 g, 0.642 mmol) in N,N-dimethylformamide (2 mL). The reaction mixture was brought to reflux at 140° C. while under a nitrogen atmosphere. After stirring for 16 hours at reflux the solution was cooled to room temperature. The reaction mixture was partitioned between ethyl acetate (120 mL) and saturated aqueous ammonium chloride (50 mL). The phases were separated and the organic layer was washed with brine (75 mL), and was subsequently dried over anhydrous magnesium sulfate. Concentration under reduced pressure afforded the crude product as an orange oil. The product was purified by flash silica column chromatography. Elution through a 80-g Silicycle® flash silica cartridge with gradient of 2% to 5% methanol in dichloromethane afforded the title intermediate (0.112 g, 53% yield); $R_f$ 0.2 with 5:95 v/v methanol-dichloromethane; MS (APCl$^+$) m/z 327.3 (M+1); H-PGDS FPBA IC$_{50}$: >10 µM.

Step B: Preparation of 2-methyl-5-(2-(pyridin-3-yl)-1H-imidazol-5-yl)pyridine

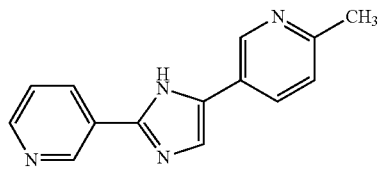 [SMILES: Cc1ccc(-c2cnc(-c3cccnc3)[nH]2)cn1]

To a solution consisting of 5-(1-benzyl-2-(pyridin-3-yl)-1H-imidazol-5-yl)-2-methylpyridine (0.112 g, 0.343 mmol) in methanol (27 mL) was added ammonium formate (Aldrich, 0.216 g, 12.7 mmol) and 10% palladium on carbon (Alfa Aesar, 0.135 g). The reaction mixture was brought to reflux at 70° C. for 16 hours. After cooling the solution to room temperature, the crude reaction mixture was filtered through a 45 µM syringe filter and was rinsed with additional methanol. Concentration of the filtrate afforded a yellow oil. The product was purified by flash silica column chromatography and eluted through a 25-g Silicycle® flash silica cartridge with 10:90 v/v methanol-dichloromethane. After combining all fractions containing product and removing the solvents, the title compound precipitated from dichloromethane as a white solid (0.013 g, 16% yield); $R_f$ 0.50 with 90:10 v/v dichloromethane-methanol; melting point 237-239° C.; $^1$H-NMR (400 MHz; MeOH-d$_4$) δ 9.11 (d, 1H), 8.85 (d, 2H), 8.56 (dd, 1H), 8.36 (m, 1H) 8.13 (dd, 1H), 7.69 (s, 1H), 7.56 (m, 1H), 7.33 (d, 1H), 2.54 (s, 3H); MS (ESI$^+$); H-PGDS FPBA IC$_{50}$: >10 µM.

Example 67

Preparation of phenyl(5-(2-(pyridin-3-yl)-1H-imidazol-5-yl)pyrimidin-2-yl)methanone

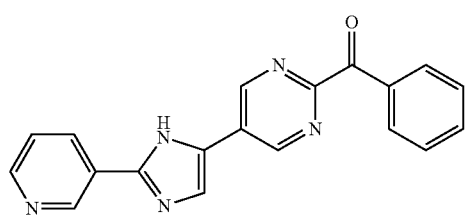 [SMILES: O=C(c1ccccc1)c1ncc(-c2cnc(-c3cccnc3)[nH]2)cn1]

The title compound is prepared by the method described in Example 1, except that (5-bromopyrimidin-2-yl)(phenyl)methanone (prepared according to the procedure described in WO 2008/121670 p. 94) is used instead of 5-bromo-2-phenylpyrimidine and 3-(1-benzyl-1H-imidazol-2-yl)pyridine is used instead of 1-benzyl-2-phenyl-1H-imidazole in Step C.

Example 68

Preparation of phenyl(5-(2-(pyridin-3-yl)-1H-imidazol-5-yl)pyrimidin-2-yl)methanol

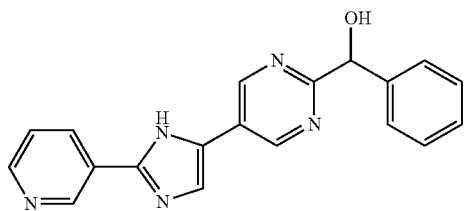 [SMILES: OC(c1ccccc1)c1ncc(-c2cnc(-c3cccnc3)[nH]2)cn1]

To a solution consisting of phenyl(5-(2-(pyridin-3-yl)-1H-imidazol-5-yl)pyrimidin-2-yl)methanone (Example 67) dissolved in methanol is added sodium borohydride (1 molar equivalent) at 0° C. The mixture is allowed to reach room temperature and is stirred one hour. The mixture is partitioned between ethyl acetate and water and the organics washed with brine, dried ($Na_2SO_4$), filtered and concentrated to afford the title compound.

Example 69

Preparation of 2-phenyl-5-(2-(1-(pyridin-3-yl)piperidin-4-yl)-1H-imidazol-4-yl)pyrimidine

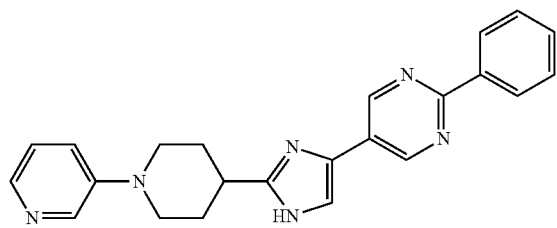 [SMILES: c1ccc(-c2ncc(-c3c[nH]c(C4CCN(c5cccnc5)CC4)n3)cn2)cc1]

The title compound is prepared in a similar manner as described in *Tetrahedron Letters*, 2007, 48(14), 2519-2525. In this case, to a degassed solution of sodium tert-butoxide, palladium acetate, and 2-dicyclohexlphosphino-2',4',6'-triisopropylbiphenyl (X-phos) in tert-butanol and toluene is added 3-bromopyridine and 2-phenyl-5-(2-(piperidin-4-yl)-1H-imidazol-4-yl)pyrimidine. The reaction is stirred and heated at 120° C. under nitrogen for 18 hours. The reaction mixture is cooled, diluted with water and the organic material is extracted with ethyl acetate. The organic phase is washed with brine, dried over magnesium sulfate, filtered and concentrated under reduced pressure. The residue is chromatographed on silica to give the title compound.

Example 70

Preparation of 3-(4-(4-(2-phenylpyrimidin-5-yl)-1H-imidazol-2-yl)piperidin-1-yl)pyridazine

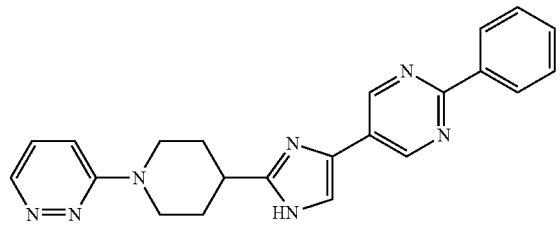 [SMILES: c1ccc(-c2ncc(-c3c[nH]c(C4CCN(c5cccnn5)CC4)n3)cn2)cc1]

The title compound is prepared in a similar manner described above using Buchwald-Hartwig amination conditions or as described in PCT International Application 2006/058338, 1 Jun. 2006. In this case, a solution consisting of 2-phenyl-5-(2-(piperidin-4-yl)-1H-imidazol-4-yl)pyrimidine and 6-chloropyridazine 1-oxide (preparation of this reagent can be found in PCT International Application 2007/106670, 20 Sep. 2007 and *Chemical and Pharmaceutical Bulletin*, 1963, 11, 261-263) in dimethylsulfoxide is heated at 80° C. for 18 hours. The reaction mixture is cooled, diluted with water and the organic material is extracted with ethyl acetate. The organic phase is washed with brine, dried over magnesium sulfate, filtered and concentrated under reduced pressure. The residue is chromatographed on silica to afford the title compound.

Example 71

Preparation of 5-(1-benzyl-2-(pyridin-3-yl)-1H-imidazol-5-yl)-4-methyl-2-phenylthiazole

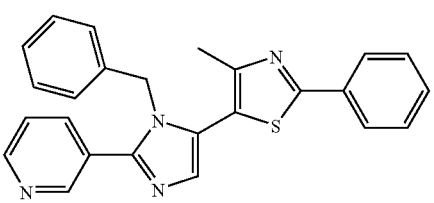 [SMILES: Cc1nc(-c2ccccc2)sc1-c1cnc(-c2cccnc2)n1Cc1ccccc1]

The title compound was prepared by the method described in Example 1, except that (i) commercially available 5-bromo-4-methyl-2-phenylthiazole (Apollo Scientific) was used instead of 5-bromo-2-phenylpyrimidine in Step C, and (ii) 3-(1-benzyl-1H-imidazol-2-yl)pyridine was used instead of 1-benzyl-2-phenyl-1H-imidazole in Step C. 3-(1-Benzyl-1H-imidazol-2-yl)pyridine was prepared by the procedure described in Example 8, Steps A and B except the commercially available 3-cyanopyridine was used instead of 3-fluorobenzonitrile; $R_f$ 0.34 with 95:5 v/v dichloromethane-methanol; $^1$H-NMR (400 MHz; DMSO-$d_6$) δ 8.87 (dd, 1H), 8.64-8.63 (dd, 1H), 7.94-7.91 (m, 1H), 7.86-7.84 (m, 2H), 7.43-7.22 (m, 8H), 6.83-6.81 (m, 2H), 5.25 (s, 2H), 2.31 (s, 3H); MS (ESI+) m/z 409.1 (M+1); H-PGDS FPBA IC$_{50}$: >20 μM.

Example 72

Preparation of 4-methyl-2-phenyl-5-(2-(pyridin-3-yl)-1H-imidazol-5-yl)thiazole

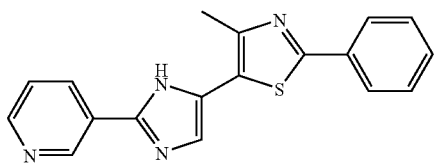 [SMILES: Cc1nc(-c2ccccc2)sc1-c1cnc(-c2cccnc2)[nH]1]

The title compound is prepared from 5-(1-benzyl-2-(pyridin-3-yl-1H-imidazol-5-yl)-4-methyl-2-phenylthiazole (Example 71) in a similar manner as described in *Tetrahedron Letters*, 2008, 64(26), 6060-6072. In this case, 5-(1-benzyl-2-(pyridin-3-yl)-1H-imidazol-5-yl)-4-methyl-2-phenylthiazole in methanol is debenzylated by hydrogenation under an atmospheric pressure of hydrogen using a balloon with vigorous stirring for 70 h under reflux. The reaction mixture is filtered through Celite, filtered and concentrated under reduced pressure. The residue is chromatographed on silica to give the title compound.

Tetrazole compounds with the general structures 24a and 24b of the exemplary embodiments may be prepared using the general synthetic route described in Scheme 8.

Scheme 8: General synthesis of 5-(tetrazol-2-yl)-pyr(im)idines and 5-(tetrazol-3-yl)-pyr(im)idines

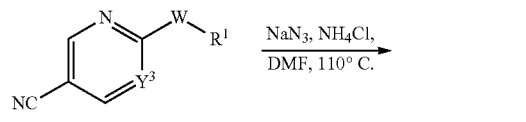

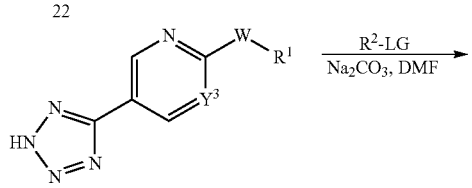

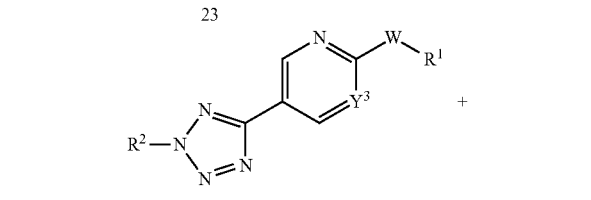

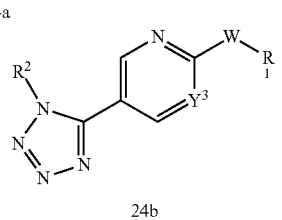

Example 73

Preparation of 5-(2-methyl-2H-tetrazol-5-yl)-2-phenylpyrimidine (A) and 5-(1-methyl-1H-tetrazol-5-yl)-2-phenylpyrimidine (B)

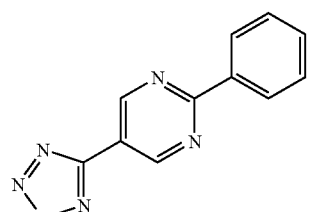

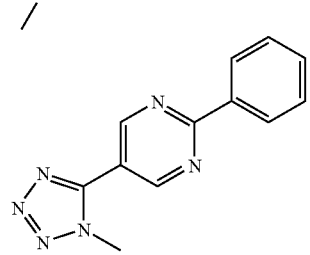

Example 73A  Example 73B

The title compounds were prepared from 2-phenyl-5-(1H-tetrazol-5-yl)pyrimidine (Example 43, 20 mg, 0.022 mmol) using iodomethane (500 μL, 8.0 mmol), triethylamine (330 μL, 2.37 mmol) in acetonitrile (3 mL). The reaction was heated to 40° C. for three hours. The reaction mixture was concentrated and purified by column chromatography using a gradient of 100% dichloromethane to 1:99 v/v methanol-dichloromethane affording the title compounds as white solids (73% total yield); Example 73A: 10.3 mg; melting point 228° C.; $^1$H-NMR (400 MHz; CDCl$_3$) δ 9.49 (s, 2H), 8.51-8.54 (m, 2H), 7.52-7.54 (m, 3H), 4.47 (s, 3H); LC/MS (ESI+) m/z 239; H-PGDS FPBA IC$_{50}$: 10 μM; Example 73B: 3.1 mg; melting point 238° C.; $^1$H-NMR (400 MHz; CDCl$_3$) δ 9.23 (s, 2H), 8.54-8.56 (m, 2H), 7.55-7.57 (m, 3H), 4.30 (s, 3H); LC/MS (ESI+) m/z 239; H-PGDS FPBA IC$_{50}$: 20 μM.

Example 74

H-PGDS Fluorescence Polarization Binding Assay

This assay essentially is available from Cayman Chemical Company as Catalog item #600007. The test data reported for the aforementioned Examples (H-PGDS FPBA IC$_{50}$) were generated using a 96-well, instead of the 384-well, format.

Detection analyte and H-PGDS-MBP fusion enzyme were incubated in the presence of reduced glutathione (5 mM) for 60-90 minutes at room temperature and FP was measured using a TECAN SAFIRE 2 plate reader equipped with absorbance, fluorescence, fluorescence polarization and FRET capabilities. Assays were performed in 96-well microtiter plates in 100 µL of total sample volume. Excitation and emission wavelengths appropriate for the employed detection analyte were used.

Step A: Preparation of Reagents (i). Detection Analyte: H-PGDS FP Fluorescent Probe—Green FP buffer concentrate (4× (200 mM Tris pH8.0, 200 mM KCl, 20 mM CHAPS, 40 mM DTT), Cayman Chemical Catalog No. 600028, 6 mL) was diluted with deionized water (18 mL) to provide 1×FP buffer (24 mL).

A solution consisting of 2-(6-hydroxy-3-oxo-3H-xanthen-9-yl)-5-(2-(3-((2-phenylpyrimidine-5-carboxamido)methyl)phenylsulfonamido)ethylcarbamoyl)benzoic acid in absolute ethanol (20 µL, 100 ug/mL) was diluted with 1×FP buffer (180 µL) to provide the H-PGDS FP fluorescent probe—green reagent.

(ii). Enzyme: H-PGDS-MBP Fusion

H-PGDS-Maltose binding protein (MBP; 100 ul, 0.5mg/ml) fusion was diluted with 1×FP buffer (900 µL).

(iii). HQL-79 FP Positive Control

Twelve clean microfuge tubes were labeled A1 through A12. A 5 mM 4-(diphenylmethoxy)-1-[3-(1H-tetrazol-5-yl)propyl-piperidine (HQL-79) in dimethyl sulfoxide (DMSO) solution (Cayman Chemical Catalog No. 600027, 100 µL) was added to tube A12. Dimethyl sulfoxide (50 µL) was added to each of tubes A1 through A11. The HQL-79 control solution was serially diluted by removing 50 µL from tube A12 and placing it in tube A11 with subsequent thorough mixing of the contents of tube A11. Next, 50 µL was removed from tube A11 and was placed into tube A10 with subsequent thorough mixing of the contents of tube A10. This process was repeated for tubes A9 through A2.

(iv). Glutathione (GSH) Solution

A 100 mM aqueous (deionized water) glutathione solution (1,500 µL in vial) was obtained from Cayman Chemical Company (Catalog No. 600029).

Step B: Preparation of Assay Cocktail

Into a 50 mL conical tube was added the H-PGDS 1×FP buffer (18.65 mL), H-PGDS FP fluorescent probe—green (138 µL), H-PGDS-MBP fusion dilution (880 µL), and glutathione solution (1,250 µL). The cocktail prepared was enough for either a standard 96-well, 384-well, or higher density plate.

Step C: Preparation of Test Compound Solutions

A test compound may be dissolved in DMSO, ethanol, or methanol at several concentrations when the titration endpoint is unknown. A final volume of 5 µL is added to each inhibitor well.

Step D: Assay Protocol (96-Well Plate Format)

(i). Apportionment of the Assay Cocktail

Assay cocktail (95 µL) was added to each plate well.

(ii). Preparation of Maximum Binding (100% Activity) Wells

DMSO (5 µL) from microfuge tube A1 was added to each plate well A1 and B1.

(iii). Apportionment of HQL-79 Positive Control Solution

Positive control solution (5 µL) from microfuge tube A2 was added to each plate well A2 and B2. Positive control solution (5 µL) from microfuge tube A3 was added to each plate well A3 and B3. This procedure was continued until all the positive control standard dilutions were aliquoted.

(iv). Apportionment of Test Compound Solutions

Test compound solutions (5 µL) were added to the wells. Each test compound concentration was typically assayed in duplicate or triplicate. The $IC_{50}$ for a particular test compound was obtained by performing a full concentration titration versus a full concentration titration of positive control. Comparison of a single concentration of a test compound to the maximum binding well provided an assessment of the relative affinity of the test compound for H-PGDS-MBP.

(v). Incubation

The plate was covered and incubated for 60-90 minutes at room temperature. The FP signal is stable for at least two hours.

(vi). Plate Reading

Plates were read with excitation and emission wavelengths of 470 nm and 530 nm (for detection analyte comprising the fluorescein fluorophore), respectively. The measurements were taken in the fluorescent polarization mode with the z-height set to the middle of the well and the G-factor set to 1.13 on a Tecan Safire 2 reader.

Example 75

H-PGDS Inhibitor Enzyme Immunoassay

The assay detects and measures $PGD_2$ generated by H-PGDS. The prostanoid product is quantified via enzyme immunoassay (EIA) using a specific $PGD_2$ antibody.

The assay is carried out by the following steps:
1. Inhibitor screening is performed in 100 mM Tris-HCl, pH 8.0 containing 1 mM GSH, 1 mM $MgCl_2$, 4% inhibitor/DMSO, 40 µM $PGH_2$ and 25 ng of PGDS in a total volume of 125 µL.
2. A reaction mixture containing 100 mM Tris-HCl, pH 8.0, 1 mM GSH, 1 mM $MgCl_2$, 25 ng H-PGDS and 4% inhibitor or DMSO (uninhibited reaction) is preincubated at 25° C. for 10 minutes.
3. Reactions are initiated using 5 µL of $PGH_2$ and quenched every 15 seconds for one minute. Reactions are quenched by taking 10 µL of reaction mixture and adding to 490 µL of 100 mM phosphate buffer containing 0.1% BSA, 400 mM NaCl, 1 mM EDTA, 20 mM $FeCl_2$, 10% 1N HCl, and 0.01% azide to prevent the non-enzymatic formation of $PGD_2$ from $PGH_2$. The $FeCl_2$ serves the purpose of reducing $PGH_2$ to 12-HHT. (Quench buffer is kept on ice at all times).
4. Quenched samples (5 µL) are further diluted 100 fold in 495 µL of 100 mM phosphate buffer containing 0.1% BSA, 400 mM NaCl, 1 mM EDTA, and 0.01% azide for the $PGD_2$ EIA assay. (Dilution buffers are kept on ice at all times).

The final 5000 fold diluted samples are analyzed following the protocol outlined in Cayman Chemical's commercially available $PGD_2$ EIA kit (Cat. #512021). 50 µL of diluted sample is analyzed at least in duplicate in the EIA assay and the amount of $PGD_2$ formed is quantified using a standard curve.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

What is claimed is:
1. A compound of Formula (I):

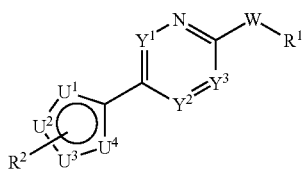

wherein:
R$^1$ is (C$_1$-C$_6$)-alkyl, (C$_3$-C$_6$)-cycloalkyl, phenyl, 2-pyridyl, 3-pyridyl, or 4-pyridyl; wherein each phenyl, 2-pyridyl, 3-pyridyl, or 4-pyridyl of R$^1$ may be optionally substituted with no more than two of each or a combination of fluoro, hydroxy, —CH$_2$OH, carboxy, carboxymethyl, or carboxyethyl;
R$^2$ is —(CH$_2$)Z$^1$ or —(CH$_2$)$_n$Z$^2$;
n is 0, 1, 2, 3, or 4;
Z$^1$ is hydrogen, OR$^3$, C(O)R$^3$, CO$_2$R$^3$, C(O)NR$^4$R$^5$, SO$_2$NR$^4$R$^5$, SO$_2$R$^3$, (C$_1$-C$_6$)-alkyl, (C$_3$-C$_6$)-cycloalkyl, (C$_3$-C$_6$)-alkenyl, (C$_3$-C$_6$)-alkynyl, (C$_6$-C$_{14}$)-aryl, (CH$_2$)$_p$ CF$_3$, a five- to ten-membered heteroaryl,

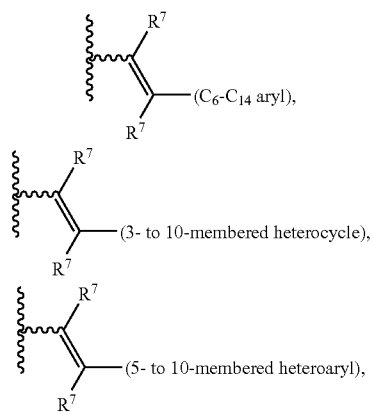

or a three- to ten-membered heterocycle; wherein any one nitrogen atom of any heterocycle containing one or more nitrogen atoms that may be substituted with a non-ring atom are substituted with —(CH$_2$)$_q$Q;
Z$^2$ is cyano, trifluoromethyl, (CF$_2$)$_p$CF$_3$, SR$^3$, NR$^4$R$^5$, N(H)C(O)R$^3$, N(H)CO$_2$R$^3$, N(H)C(O)NR$^4$R$^5$, N(H)SO$_2$R$^3$, vinyl, or ethynyl when n is 1, 2, 3 or 4;
Z$^2$ may also be cyano, trifluoromethyl, (CF$_2$)$_p$CF$_3$, SR$^3$, NR$^4$R$^5$, N(H)C(O)R$^3$, N(H)CO$_2$R$^3$, N(H)C(O)NR$^4$R$^5$, N(H)SO$_2$R$^3$, vinyl, or ethynyl when n is 0, except when R$^2$ is covalently bonded to a U$^1$, U$^2$, U$^3$, or U$^4$ that is a nitrogen atom;
R$^3$ is hydrogen, (C$_1$-C$_6$)-alkyl, trifluoromethyl, (C$_3$-C$_6$)-alkenyl, (C$_3$-C$_6$)-alkynyl, (CH$_2$)$_m$(C$_3$-C$_6$)-cycloalkyl, (CH$_2$)$_m$phenyl, (CH$_2$)$_m$-(five- to ten-membered heteroaryl), or (CH$_2$)$_m$(three- to ten-membered heterocycle), wherein any one nitrogen atom of any heterocycle containing one or more nitrogen atoms that may be substituted with a non-ring atom are substituted with —(CH$_2$)$_q$Q;
m is 0, 1, 2, 3, or 4;
q is 0, 1, 2, 3, or 4;
Q is hydrogen, (C$_1$-C$_6$)-alkyl, (CH$_2$)$_p$CF$_3$, (C$_3$-C$_6$)-alkenyl, (C$_3$-C$_6$)-alkynyl, (C$_3$-C$_6$)-cycloalkyl, (C$_6$-C$_{14}$)-aryl, C(O)R$^3$, CO$_2$R$^3$, C(O)NR$^4$R$^5$, a three- to six-membered heterocycle, or a five- to ten-membered heteroaryl when q is 0, 1, 2, 3, or 4;
Q may also be cyano, trifluoromethyl, or SO$_2$NR$^4$R$^5$ when q is 1, 2, 3, or 4;
Q may also be hydroxy, (C$_1$-C$_6$)-alkoxy, sulfhydryl, —S—(C$_1$-C$_6$)-alkyl, or NR$^4$R$^5$ when q is 2, 3, or 4;
p is 1, 2, or 3;
R$^3$ may also be vinyl or ethynyl when R$^3$ is not covalently bonded to an N or O atom;
R$^3$ may also be vinyl or ethynyl when R$^3$ is not covalently bonded to an S atom possessing a −2 (minus 2) oxidation state;
R$^4$ and R$^5$ are independently hydrogen, (C$_1$-C$_6$)-alkyl, (C$_3$-C$_6$)-alkenyl, (C$_3$-C$_6$)-alkynyl, (CH$_2$)$_m$(C$_3$-C$_6$)-cycloalkyl, (CH$_2$)$_m$phenyl, (CH$_2$)$_m$-(three- to ten-membered heterocycyl), or (CH$_2$)$_m$-(five- to ten-membered heteroaryl);
the NR$^4$R$^5$ group of any C(O)NR$^4$R$^5$, SO$_2$NR$^4$R$^5$, NR$^4$R$^5$, or N(H)C(O)NR$^4$R$^5$ may also form a pyrrolidine, a piperidine, a morpholine, a thiomorpholine, or a thiomorpholine S-dioxide;
the NR$^4$R$^5$ group of any C(O)NR$^4$R$^5$, SO$_2$NR$^4$R$^5$, NR$^4$R$^5$, or N(H)C(O)NR$^4$R$^5$ may also form a piperazine ring, wherein the other nitrogen atom of the piperazine ring is substituted with hydrogen, (C$_1$-C$_6$)-alkyl, CH$_2$CF$_3$, (C$_3$-C$_6$)-cycloalkyl, CH$_2$(C$_3$-C$_6$)-cycloalkyl, phenyl, benzyl, hydroxyethyl, or hydroxypropyl;
phenyl or heteroaryl rings of Z$^1$ and Z$^2$ are optionally substituted with one-to-three of any one or combination of the following: halo, hydroxy, sulfhydryl, (C$_1$-C$_3$)-alkoxy, (C$_1$-C$_3$)-alkyl, (C$_1$-C$_3$)-alkylthio, trifluoromethyl, trifluoromethoxy, cyano, carboxy, carboxy (C$_1$-C$_3$)-alkyl, carbamoyl, or sulfamoyl;
W is a covalent bond, O, S, SO, SO$_2$, CH$_2$, CHOH, or CO;
U$^1$, U$^2$, U$^3$, U$^4$, and a carbon atom form a five-membered heteroaryl ring; wherein one of U$^1$, U$^2$, U$^3$, and U$^4$ of the five-membered heteroaryl ring is covalently bonded to the R$^2$ group; wherein the U$^1$, U$^2$, U$^3$, or U$^4$ that is covalently bonded to the R$^2$ group is a carbon atom or a nitrogen atom; wherein when the U$^1$, U$^2$, U$^3$, or U$^4$ that is covalently bonded to the R$^2$ group is a nitrogen atom, one, two, or all of the other three of the group consisting of U$^1$, U$^2$, U$^3$, and U$^4$ is N and each remaining of the group consisting of U$^1$, U$^2$, U$^3$, and U$^4$ that is not N is C—R$^6$; wherein when the U$^1$, U$^2$, U$^3$, or U$^4$ that is covalently bonded to the R$^2$ group is a carbon atom, one of the other three of the group consisting of U$^1$, U$^2$, U$^3$, and U$^4$ is N—R$^6$, O, or S, and each of remaining of the group consisting of U$^1$, U$^2$, U$^3$, and U$^4$ is C—R$^6$ or N with the further proviso that when Z$^2$ is SR$^3$ and n is 0, then at most one of the other three of the group consisting of U$^1$, U$^2$, U$^3$, and U$^4$ is N-R$^6$;
Y$^2$ is a CH;
Y$^1$, Y$^2$, Y$^3$, a nitrogen atom, and two carbon atoms form a six-membered heteroaryl ring; wherein no more than one of the group consisting of Y$^1$ and Y$^3$ is N; and wherein all Y$^1$ and Y$^3$ that are not N are C—R$^6$;
each R$^6$ is independently hydrogen, methyl, trifluoromethyl, or amino; and
each R$^7$ is independently hydrogen or methyl.

2. A compound of claim 1, wherein the compound according to Formula (I) comprises a compound according to Formula (III):

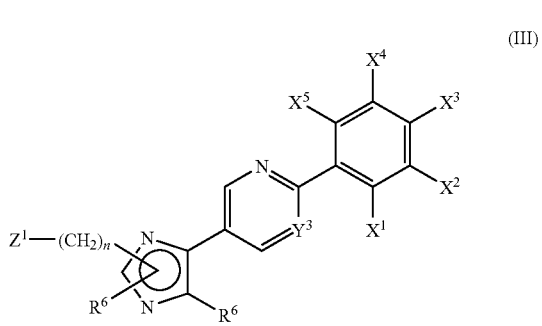

(III)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
$Y^3$ is CH or N;
each $R^6$ is independently hydrogen, methyl, trifluoromethyl, or amino;
n is 0, 1, 2, 3, or 4;
$Z^1$ is hydrogen, $OR^3$, $C(O)R^3$, $CO_2R^3$, $C(O)NR^4R^5$, $SO2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

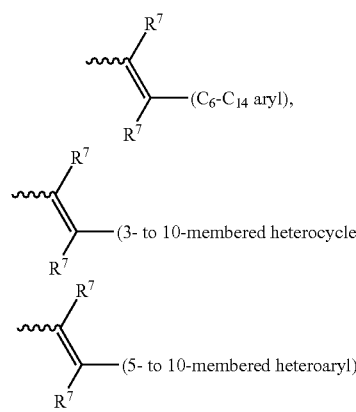

or a three- to ten-membered heterocycle, wherein any one nitrogen atom of any heterocycle containing one or more nitrogen atoms that may be substituted with a non-ring atom are substituted with —$(CH_2)_qQ$;
p is 1, 2, or 3;
$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$-(three- to ten-membered heterocycle) wherein any one nitrogen atom of any heterocycle containing one or more nitrogen atoms that may be substituted with a non-ring atom are substituted with —$(CH_2)_qQ$;
$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;
the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;
m is 0, 1, 2, 3, or 4;
q is 0, 1, 2, 3, or 4;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl;
Q may also be cyano, trifluoromethyl, or $SO_2NR^4R^5$ when q is 1, 2, 3, or 4;
Q may also be hydroxy, sulfhydryl, or $NR^4R^5$ when q is 2, 3, or 4;
phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl; and
$R^7$ is hydrogen or methyl.

3. A compound of claim 2, wherein the compound according to Formula (III) comprises a compound according to Formula (IV):

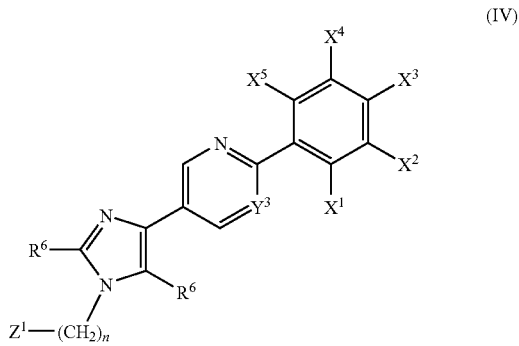

(IV)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
$Y^3$ is CH or N;
each $R^6$ is independently hydrogen, methyl, trifluoromethyl, or amino;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

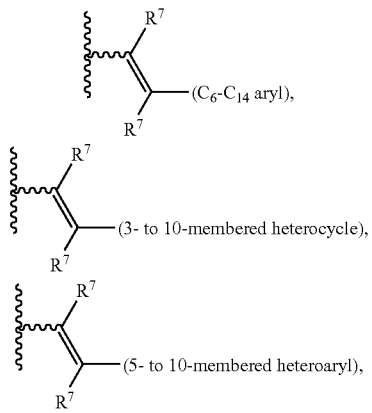

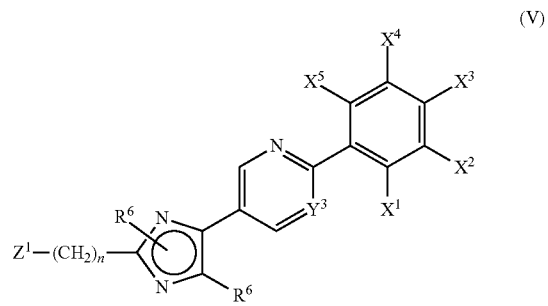

or a three- to ten-membered heterocycle; wherein any one nitrogen atom of any heterocycle containing one or more nitrogen atoms that may be substituted with a non-ring atom are substituted with —$(CH_2)_q Q$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$-(three- to ten-membered heterocycle); wherein any one nitrogen atom of any heterocycle containing one or more nitrogen atoms that may be substituted with a non-ring atom are substituted with —$(CH_2)_q Q$;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

m is 0, 1, 2, 3, or 4;

q is 0, 1, 2, 3, or 4;

Q is hydrogen, $(C_1-C_6)$-alkyl, $(CH_2)_p CF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl; and $R^7$ is hydrogen or methyl.

4. A compound of claim 2, wherein the compound according to Formula (III) comprises a compound according to Formula (V):

(V)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

$Y^3$ is CH or N;

each $R^6$ is independently hydrogen, methyl, trifluoromethyl, or amino;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

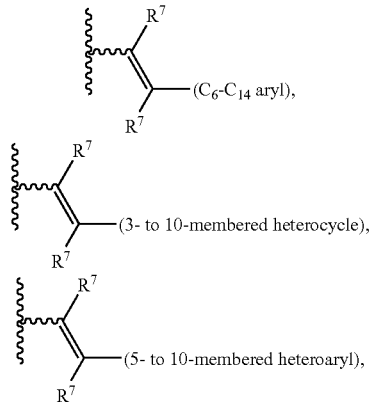

or a three- to ten-membered heterocycle; wherein any one nitrogen atom of any heterocycle containing one or more nitrogen atoms that may be substituted with a non-ring atom are substituted with —$(CH_2)_q Q$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$-(three- to ten-membered heterocycle); wherein any one nitrogen atom of any heterocycle containing one or more nitrogen atoms that may be substituted with a non-ring atom are substituted with —$(CH_2)_q Q$;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the NR$^4$R$^5$ group of any C(O)NR$^4$R$^5$, SO$_2$NR$^4$R$^5$, NR$^4$R$^5$, or N(H)C(O)NR$^4$R$^5$ may also form a piperazine ring, wherein the other nitrogen atom of the piperazine ring is substituted with hydrogen, (C$_1$-C$_6$)-alkyl, CH$_2$CF$_3$, (C$_3$-C$_6$)-cycloalkyl, CH$_2$(C$_3$-C$_6$)-cycloalkyl, phenyl, benzyl, hydroxyethyl, or hydroxypropyl;

m is 0, 1, 2, 3, or 4;

q is 0, 1, 2, 3, or 4;

Q is hydrogen, (C$_1$-C$_6$)-alkyl, (CH$_2$)$_p$CF$_3$, (C$_3$-C$_6$)-alkenyl, (C$_3$-C$_6$)-alkynyl, (C$_3$-C$_6$)-cycloalkyl, (C$_6$-C$_{14}$)-aryl, C(O)R$^3$, CO$_2$R$^3$, C(O)NR$^4$R$^5$, a three- to six-membered heterocycle, or a five- to ten-membered heteroaryl;

Q may also be cyano, trifluoromethyl, or SO$_2$NR$^4$R$^5$ when q is 1, 2, 3, or 4;

Q may also be hydroxy, (C$_1$-C$_6$)-alkoxy, sulfhydryl, —S—(C$_1$-C$_6$)-alkyl, or NR$^4$R$^5$ when q is 2, 3, or 4;

p is 1, 2, or 3;

phenyl or heteroaryl rings of Z$^1$ are optionally substituted with one-to-three of any one or combination of the following: halo, hydroxy, sulfhydryl, (C$_1$-C$_3$)-alkoxy, (C$_1$-C$_3$)-alkyl, (C$_1$-C$_3$)-alkylthio, trifluoromethyl, trifluoromethoxy, cyano, carboxy, carboxy(C$_1$-C$_3$)-alkyl, carbamoyl, or sulfamoyl; and R$^7$ is hydrogen or methyl.

5. A compound of claim 4, wherein Y$^3$ is N.

6. A compound of claim 5, wherein:

each X$^1$, X$^3$, X$^4$, and X$^5$ is hydrogen;

X$^2$ is hydrogen or fluoro;

each R$^6$ is independently hydrogen, methyl, or trifluoromethyl;

n is 0, 1, or 2;

Z$^1$ is phenyl, 2-pyridyl, 3-pyridyl, 4-pyridyl, piperidin-4-yl, piperidin-3-yl, piperidin-3(R)-yl, piperidin-3(S)-yl, piperidin-2-yl, piperidin-2(R)-yl, piperidin-2(S)-yl, pyrrolidin-3-yl, pyrrolidin-3(R)-yl, pyrrolidin-3(S)-yl, pyrrolidin-2-yl, pyrrolidin-2(R)-yl, pyrrolidin-2(S)-yl, or azetidin-3-yl;

the nitrogen atom of a piperidinyl, a pyrrolidinyl, or a azetidinyl ring is substituted with —(CH$_2$)$_q$Q;

q is 0, 1, or 2;

Q is hydrogen, (C$_1$-C$_6$)-alkyl, —CH$_2$CF$_3$, (C$_3$-C$_6$)-alkenyl, (C$_3$-C$_6$)-alkynyl, (C$_3$-C$_6$)-cycloalkyl, phenyl, naphthyl, C(O)R$^3$, CO$_2$R$^3$, C(O)NR$^4$R$^5$, a three- to six-membered heterocycle, or a five- to ten-membered heteroaryl;

R$^3$ is hydrogen, (C$_1$-C$_6$)-alkyl, trifluoromethyl, (C$_3$-C$_6$)-alkenyl, (C$_3$-C$_6$)-alkynyl, (CH$_2$)$_m$(C$_3$-C$_6$)-cycloalkyl, (CH$_2$)$_m$phenyl, or (CH$_2$)$_m$-(five- to ten-membered heteroaryl); and m is 0, 1, or 2.

7. A compound of claim 6, wherein:

Z$^1$ is phenyl, 2-pyridyl, 3-pyridyl, or 4-pyridyl; and wherein said phenyl or pyridyl rings of Z$^1$ are optionally substituted with one or two of any one or combination of the following: halo, hydroxy, methoxy, methyl, or trifluoromethyl.

8. A compound of claim 7, wherein:

Z$^1$ is phenyl; and wherein said phenyl ring of Z$^1$ is substituted with one or two of any one or combination of the following: halo, hydroxy, methoxy, methyl, or trifluoromethyl.

9. A compound of claim 8, wherein said phenyl ring of Z$^1$ is substituted with one or two of any one or combination of the following: halo or methoxy.

10. A compound of claim 7, wherein Z$^1$ is 2-pyridyl, 3-pyridyl, or 4-pyridyl.

11. A compound of claim 6, wherein Z$^1$ is piperidin-4-yl, piperidin-3-yl, piperidin-3(R)-yl, piperidin-3(S)-yl, piperidin-2-yl, piperidin-2(R)-yl, piperidin-2(S)-yl, pyrrolidin-3-yl, pyrrolidin-3(R)-yl, pyrrolidin-3(S)-yl, pyrrolidin-2-yl, pyrrolidin-2(R)-yl, pyrrolidin-2(S)-yl, or azetidin-3-yl.

12. A compound of claim 11, wherein:

q is 0 or 1;

Q is (C$_1$-C$_4$)-alkyl, —CH$_2$CF$_3$, (C$_3$-C$_6$)-cycloalkyl, phenyl, C(O)R$^3$, CO$_2$R$^3$, C(O)NHR$^5$, a five- to six-membered heterocycle, or a five- to ten-membered heteroaryl;

R$^3$ is hydrogen, (C$_1$-C$_4$)-alkyl, trifluoromethyl, (CH$_2$)$_m$(C$_3$-C$_6$)-cycloalkyl, (CH$_2$)$_m$phenyl, or (CH$_2$)$_m$-(five- to six-membered heteroaryl); and m is 0, 1, or 2.

13. A compound of claim 12, wherein q is 1; and

Q is (C$_1$-C$_4$)-alkyl, —CH$_2$CF$_3$, (C$_3$-C$_6$)-cycloalkyl, phenyl, a five- to six-membered heterocycle, or a five- to ten-membered heteroaryl.

14. A compound of claim 12, wherein q is 0.

15. A compound of claim 4, or a pharmaceutically acceptable salt thereof, wherein Y$^3$ is CH.

16. A compound of claim 15, or a pharmaceutically acceptable salt thereof, wherein:

each X$^1$, X$^3$, X$^4$, and X$^5$ is hydrogen;

X$^2$ is hydrogen or fluoro;

R$^6$ is hydrogen, methyl, or trifluoromethyl;

n is 0, 1, or 2;

Z$^1$ is phenyl, 2-pyridyl, 3-pyridyl, 4-pyridyl, piperidin-4-yl, piperidin-3-yl, piperidin-3(R)-yl, piperidin-3(S)-yl, piperidin-2-yl, piperidin-2(R)-yl, piperidin-2(S)-yl, pyrrolidin-3-yl, pyrrolidin-3(R)-yl, pyrrolidin-3(S)-yl, pyrrolidin-2-yl, pyrrolidin-2(R)-yl, pyrrolidin-2(S)-yl, or azetidin-3-yl;

the nitrogen atom of a piperidinyl, a pyrrolidinyl, or a azetidinyl ring of Z$^1$ is substituted with —(CH$_2$)$_q$Q;

q is 0, 1, or 2;

Q is hydrogen, (C$_1$-C$_6$)-alkyl, —CH$_2$CF$_3$, (C$_3$-C$_6$)-alkenyl, (C$_3$-C$_6$)-alkynyl, (C$_3$-C$_6$)-cycloalkyl, phenyl, naphthyl, C(O)R$^3$, CO$_2$R$^3$, C(O)NR$^4$R$^5$, a three- to six-membered heterocycle, or a five- to ten-membered heteroaryl;

R$^3$ is hydrogen, (C$_1$-C$_6$)-alkyl, trifluoromethyl, (C$_3$-C$_6$)-alkenyl, (C$_3$-C$_6$)-alkynyl, (CH$_2$)$_m$(C$_3$-C$_6$)-cycloalkyl, (CH$_2$)$_m$phenyl, or (CH$_2$)$_m$-(five- to ten-membered heteroaryl); and m is 0, 1, or 2.

17. A compound of claim 16, or a pharmaceutically acceptable salt thereof, wherein:

Z$^1$ is phenyl, 2-pyridyl, 3-pyridyl, or 4-pyridyl; and said phenyl or pyridyl rings may be optionally substituted with one or two of any one or combination of the following: halo, hydroxy, methoxy, methyl, or trifluoromethyl.

18. A compound of claim 17, wherein:

Z$^1$ is phenyl; and said phenyl ring of Z$^1$ is substituted with one or two of any one or combination of the following: halo, hydroxy, methoxy, methyl, or trifluoromethyl.

19. A compound of claim 18, wherein said phenyl ring of Z$^1$ is substituted with one or two of any one or combination of the following: halo or methoxy.

20. A compound of claim 17, wherein Z$^1$ is 2-pyridyl, 3-pyridyl, or 4-pyridyl.

21. A compound of claim 16, wherein Z$^1$ is piperidin-4-yl, piperidin-3-yl, piperidin-3(R)-yl, piperidin-3(S)-yl, piperidin-2-yl, piperidin-2(R)-yl, piperidin-2(S)-yl, pyrrolidin-3-yl, pyrrolidin-3(R)-yl, pyrrolidin-3(S)-yl, pyrrolidin-2-yl, pyrrolidin-2(R)-yl, pyrrolidin-2(S)-yl, or azetidin-3-yl.

22. A compound of claim 21, wherein:
q is 0 or 1;
Q is $(C_1-C_4)$-alkyl, —$CH_2CF_3$, $(C_3-C_6)$-cycloalkyl, phenyl, $C(O)R^3$, $CO_2R^3$, $C(O)NHR^5$, a five- to six-membered heterocycle, or a five- to ten-membered heteroaryl;
$R^3$ is hydrogen, $(C_1-C_4)$-alkyl, trifluoromethyl, $(CH_2)_m(C_3-C_6)$-cycloalkyl, $(CH_2)_m$phenyl, or $(CH_2)_m$-(five- to six-membered heteroaryl); and
m is 0, 1, or 2.

23. A compound of claim 22, wherein:
q is 1; and
Q is $(C_1-C_4)$-alkyl, —$CH_2CF_3$, $(C_3-C_6)$-cycloalkyl, phenyl, a five- to six-membered heterocycle, or a five- to ten-membered heteroaryl.

24. A compound of claim 22, wherein:
q is 0;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NHR^5$, a three- to six-membered heterocycle, or a five- to ten-membered heteroaryl;
phenyl or heteroaryl rings are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl.

25. A compound of claim 1, wherein the compound according to Formula (I) comprises a compound according to Formula (VI):

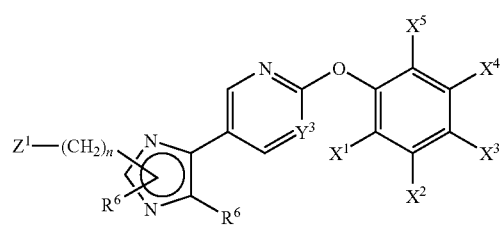

(VI)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

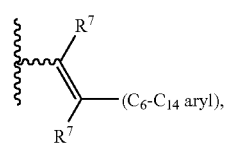

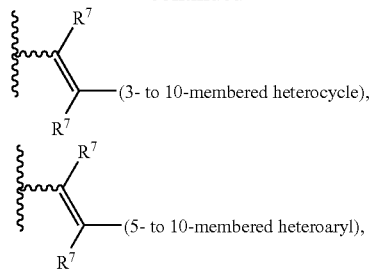

or a three- to ten-membered heterocycle; wherein any one nitrogen atom of any heterocycle containing one or more nitrogen atoms that may be substituted with a non-ring atom are substituted with —$(CH_2)_qQ$;
$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;
m is 0, 1, 2, 3, or 4;
q is 0, 1, 2, 3, or 4;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;
Q may also be cyano, trifluoromethyl, or $SO_2NR^4R^5$ when q is 1, 2, 3, or 4;
Q may also be hydroxy, $(C_1-C_6)$-alkoxy, sulfhydryl, —S—$(C_1-C_6)$-alkyl, or $NR^4R^5$ when q is 2, 3, or 4;
p is 1, 2, or 3;
$R^3$ may also be vinyl or ethynyl when $R^3$ is not covalently bonded to an N or O atom;
$R^3$ may also be vinyl or ethynyl when $R^3$ is not covalently bonded to an S atom possessing a –2 (minus 2) oxidation state;
$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);
the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;
the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;
phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;
each $R^6$ is independently hydrogen, methyl, trifluoromethyl, or amino; and
each $R^7$ is independently hydrogen or methyl.

26. A compound of claim 25, wherein the compound according to Formula (VI) comprises a compound according to Formula (VII):

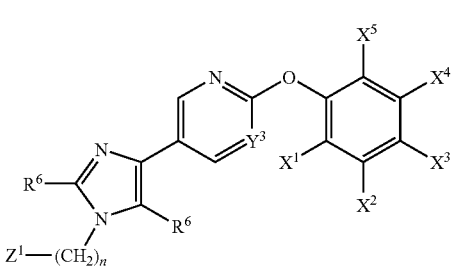

(VII)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

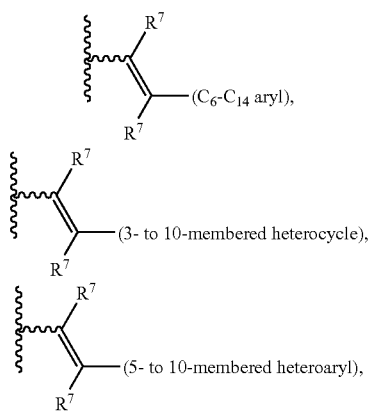

or a three- to ten-membered heterocycle; wherein any one nitrogen atom of any heterocycle containing one or more nitrogen atoms that may be substituted with a non-ring atom are substituted with —$(CH_2)_qQ$;
$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;
m is 0, 1, 2, 3, or 4;
q is 0, 1, 2, 3, or 4;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;
Q may also be cyano, trifluoromethyl, or $SO_2NR^4R^5$ when q is 1, 2, 3, or 4;
Q may also be hydroxy, $(C_1-C_6)$-alkoxy, sulfhydryl, —S—$(C_1-C_6)$-alkyl, or $NR^4R^5$ when q is 2, 3, or 4;
p is 1, 2, or 3;
$R^3$ may also be vinyl or ethynyl when $R^3$ is not covalently bonded to an N or O atom;
$R^3$ may also be vinyl or ethynyl when $R^3$ is not covalently bonded to an S atom possessing a −2 (minus 2) oxidation state;
$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);
the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;
the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;
phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;
each $R^6$ is independently hydrogen, methyl, trifluoromethyl, or amino; and
each $R^7$ is independently hydrogen or methyl.

27. A compound of claim 25, wherein the compound according to Formula (VI) comprises a compound according to Formula (VIII):

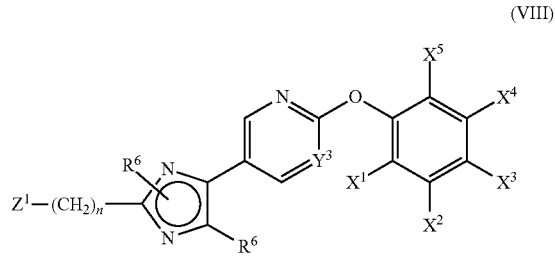

(VIII)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

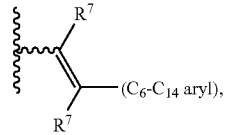

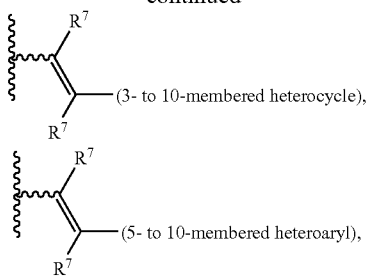
(3- to 10-membered heterocycle), (5- to 10-membered heteroaryl), or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;
q is 0, 1, 2, 3, or 4;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;
Q may also be cyano, trifluoromethyl, or $SO_2NR^4R^5$ when q is 1, 2, 3, or 4;
Q may also be hydroxy, $(C_1-C_6)$-alkoxy, sulfhydryl, —S—$(C_1-C_6)$-alkyl, or $NR^4R^5$ when q is 2, 3, or 4;
p is 1, 2, or 3;
$R^3$ may also be vinyl or ethynyl when $R^3$ is not covalently bonded to an N or O atom;
$R^3$ may also be vinyl or ethynyl when $R^3$ is not covalently bonded to an S atom possessing a −2 (minus 2) oxidation state;
$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);
the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;
the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;
phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;
each $R^6$ is independently hydrogen, methyl, trifluoromethyl, or amino; and
each $R^7$ is independently hydrogen or methyl.

28. A compound of claim 27, wherein $Y^3$ is N and each $R^6$ is independently hydrogen, methyl, or trifluoromethyl.

29. A compound of claim 27, wherein $Y^3$ is CH and each $R^6$ is independently hydrogen, methyl, or trifluoromethyl.

30. A compound of claim 1, wherein the compound according to Formula (I) comprises a compound according to Formula (IX):

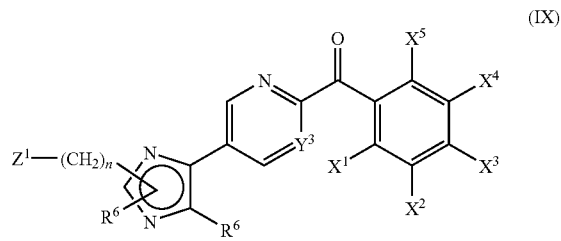

(IX)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

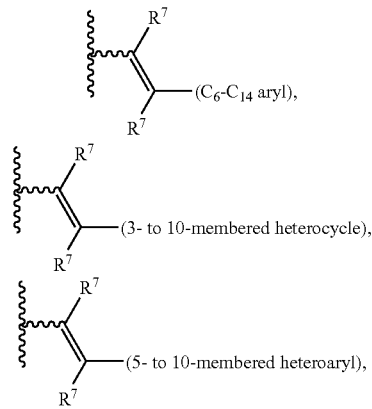

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;
q is 0, 1, 2, 3, or 4;
Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a –2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

31. A compound of claim 30, wherein the compound according to Formula (IX) comprises a compound according to Formula (X):

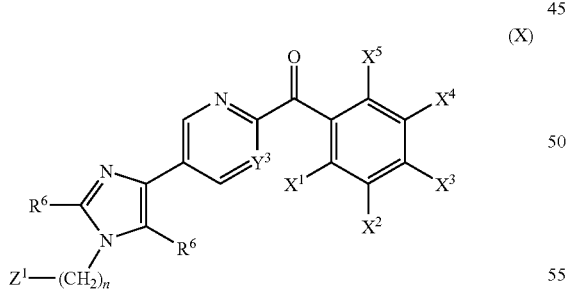

(X)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

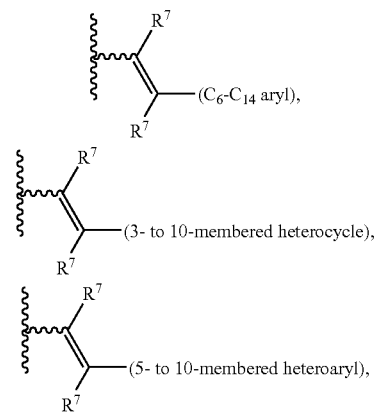

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a –2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1$-

$C_3$)-alkyl, ($C_1$-$C_3$)-alkylthio, trifluoromethyl, trifluoromethoxy, cyano, carboxy, carboxy ($C_1$-$C_3$)-alkyl, carbamoyl, or sulfamoyl;

each $R^6$ is independently hydrogen, methyl, trifluoromethyl, or amino; and each $R^7$ is independently hydrogen or methyl.

32. A compound of claim 31, wherein $Y^3$ is N and each $R^6$ is independently hydrogen, methyl, or trifluoromethyl.

33. A compound of claim 31, wherein $Y^3$ is CH and each $R^6$ is independently hydrogen, methyl, or trifluoromethyl.

34. A compound of claim 30, wherein the compound according to Formula (IX) comprises a compound according to Formula (XI):

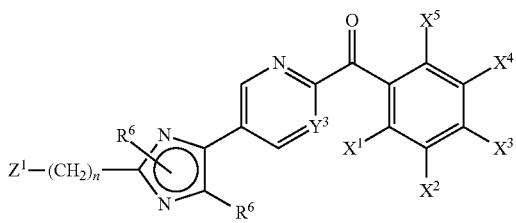

(XI)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, ($C_1$-$C_6$)-alkyl, ($C_3$-$C_6$)-cycloalkyl, ($C_3$-$C_6$)-alkenyl, ($C_3$-$C_6$)-alkynyl, ($C_6$-$C_{14}$)-aryl, $(CH_2)_p CF_3$, a five- to ten-membered heteroaryl,

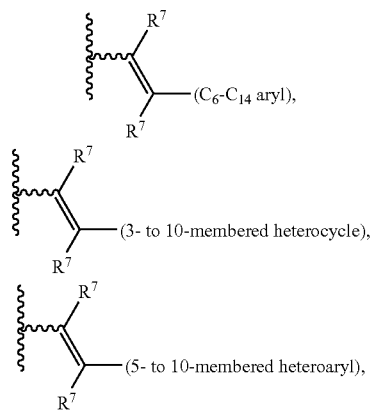

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, ($C_1$-$C_6$)-alkyl, trifluoromethyl, ($C_3$-$C_6$)-alkenyl, ($C_3$-$C_6$)-alkynyl, $(CH_2)_m(C_3$-$C_6)$-cycloalkyl, $(CH_2)_m$phenyl, $(CH_2)_m$-(five- to ten-membered heteroaryl), or $(CH_2)_m$-(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, ($C_1$-$C_6$)-alkyl, $(CH_2)_pCF_3$, ($C_3$-$C_6$)-alkenyl, ($C_3$-$C_6$)-alkynyl, ($C_3$-$C_6$)-cycloalkyl, ($C_6$-$C_{14}$)-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, ($C_1$-$C_6$)-alkoxy, sulfhydryl, —S—($C_1$-$C_6$)-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, ($C_1$-$C_6$)-alkyl, ($C_3$-$C_6$)-alkenyl, ($C_3$-$C_6$)-alkynyl, $(CH_2)_m(C_3$-$C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, ($C_1$-$C_6$)-alkyl, $CH_2CF_3$, ($C_3$-$C_6$)-cycloalkyl, $CH_2(C_3$-$C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, ($C_1$-$C_3$)-alkoxy, ($C_1$-$C_3$)-alkyl, ($C_1$-$C_3$)-alkylthio, trifluoromethyl, trifluoromethoxy, cyano, carboxy, carboxy($C_1$-$C_3$)-alkyl, carbamoyl, or sulfamoyl;

each $R^6$ is independently hydrogen, methyl, trifluoromethyl, or amino; and each $R^7$ is independently hydrogen or methyl.

35. A compound of claim 34, wherein $Y^3$ is N and each $R^6$ is independently hydrogen, methyl, or trifluoromethyl.

36. A compound of claim 34, wherein $Y^3$ is CH and each $R^6$ is independently hydrogen, methyl, or trifluoromethyl.

37. A compound of claim 1, wherein the compound according to Formula (I) comprises a compound according to Formula (XII):

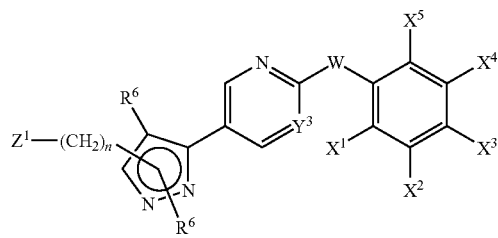

(XII)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1\text{-}C_6)$-alkyl, $(C_3\text{-}C_6)$-cycloalkyl, $(C_3\text{-}C_6)$-alkenyl, $(C_3\text{-}C_6)$-alkynyl, $(C_6\text{-}C_{14})$-aryl, $(CH_2)_p CF_3$, a five- to ten-membered heteroaryl,

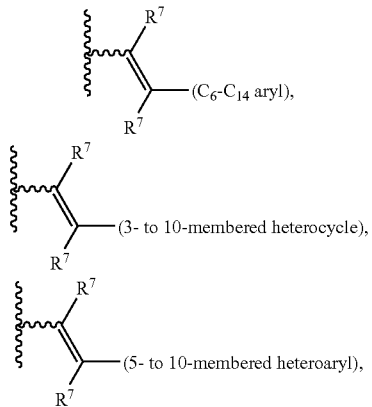

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1\text{-}C_6)$-alkyl, trifluoromethyl, $(C_3\text{-}C_6)$-alkenyl, $(C_3\text{-}C_6)$-alkynyl, $(CH_2)_m(C_3\text{-}C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1\text{-}C_6)$-alkyl, $(CH_2)_pCF_3$, $(C_3\text{-}C_6)$-alkenyl, $(C_3\text{-}C_6)$-alkynyl, $(C_3\text{-}C_6)$-cycloalkyl, $(C_6\text{-}C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1\text{-}C_6)$-alkoxy, sulfhydryl, —S—$(C_1\text{-}C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1\text{-}C_6)$-alkyl, $(C_3\text{-}C_6)$-alkenyl, $(C_3\text{-}C_6)$-alkynyl, $(CH_2)_m(C_3\text{-}C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1\text{-}C_6)$-alkyl, $CH_2CF_3$, $(C_3\text{-}C_6)$-cycloalkyl, $CH_2(C_3\text{-}C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1\text{-}C_3)$-alkoxy, $(C_1\text{-}C_3)$-alkyl, $(C_1\text{-}C_3)$-alkylthio, trifluoromethyl, trifluoromethoxy, cyano, carboxy, carboxy$(C_1\text{-}C_3)$-alkyl, carbamoyl, or sulfamoyl;

each $R^6$ is independently hydrogen, methyl, trifluoromethyl, or amino; and each $R^7$ is independently hydrogen or methyl.

38. A compound of claim 37, wherein the compound according to Formula (XII) comprises a compound according to Formula (XIII)

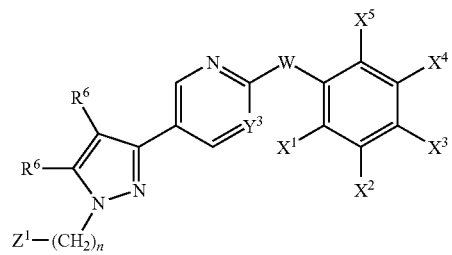

(XIII)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1\text{-}C_6)$-alkyl, $(C_3\text{-}C_6)$-cycloalkyl, $(C_3\text{-}C_6)$-alkenyl, $(C_3\text{-}C_6)$-alkynyl, $(C_6\text{-}C_{14})$-aryl, $(CH_2)_p CF_3$, a five- to ten-membered heteroaryl,

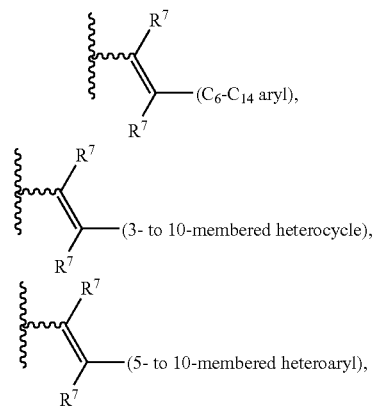

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1\text{-}C_6)$-alkyl, trifluoromethyl, $(C_3\text{-}C_6)$-alkenyl, $(C_3\text{-}C_6)$-alkynyl, $(CH_2)_m(C_3\text{-}C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_q Q$;

m is 0, 1, 2, 3, or 4;

q is 0, 1, 2, 3, or 4;

Q is hydrogen, $(C_1-C_6)$-alkyl, $(CH_2)_p CF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

39. A compound of claim 38, wherein $Y^3$ is N and each $R^6$ is independently hydrogen, methyl, or trifluoromethyl.

40. A compound of claim 38, wherein $Y^3$ is CH and each $R^6$ is independently hydrogen, methyl, or trifluoromethyl.

41. A compound of claim 37, wherein the compound according to Formula (XII) comprises a compound according to Formula (XIV):

(XIV)

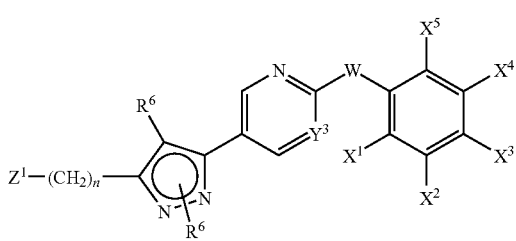

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

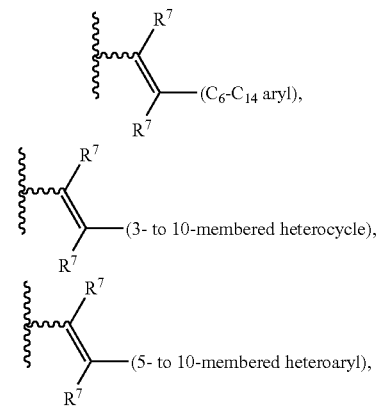

or a three- to ten-membered heterocycle; wherein any one nitrogen atom of any heterocycle containing one or more nitrogen atoms that may be substituted with a non-ring atom are substituted with —$(CH_2)_q Q$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_q Q$;

m is 0, 1, 2, 3, or 4;

q is 0, 1, 2, 3, or 4;

Q is hydrogen, $(C_1-C_6)$-alkyl, $(CH_2)_p CF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the NR⁴R⁵ group of any C(O)NR⁴R⁵, SO₂NR⁴R⁵, NR⁴R⁵, or N(H)C(O)NR⁴R⁵ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

42. A compound of claim 41, wherein $Y^3$ is N and each $R^6$ is independently hydrogen, methyl, or trifluoromethyl.

43. A compound of claim 41, wherein $Y^3$ is CH and each $R^6$ is independently hydrogen, methyl, or trifluoromethyl.

44. A compound of claim 1, wherein the compound according to Formula (I) comprises a compound according to Formula (XV):

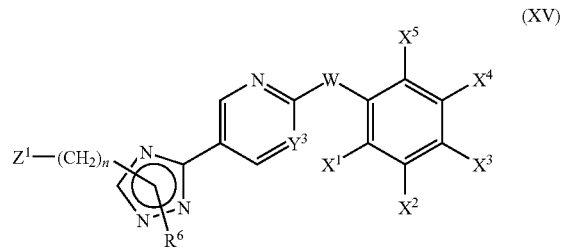

(XV)

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;
W is a covalent bond, O, or CO;
n is 0, 1, 2, 3, or 4;
$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

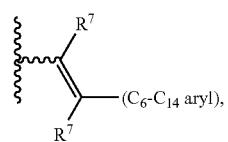

(C₆-C₁₄ aryl),

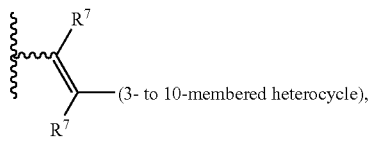

(3- to 10-membered heterocycle),

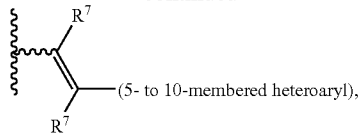

(5- to 10-membered heteroaryl), or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$-(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3 ̄C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the NR⁴R⁵ group of any C(O)NR⁴R⁵, SO₂NR⁴R⁵, NR⁴R⁵, or N(H)C(O)NR⁴R⁵ may also form a pyrrolidine, a piperidine, a morpholine, a thiomorpholine, or a thiomorpholine S-dioxide;

the NR⁴R⁵ group of any C(O)NR⁴R⁵, SO₂NR⁴R⁵, NR⁴R⁵, or N(H)C(O)NR⁴R⁵ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

45. A compound of claim 44, wherein the compound according to Formula (XV) comprises a compound according to Formula (XVI):

(XVI)

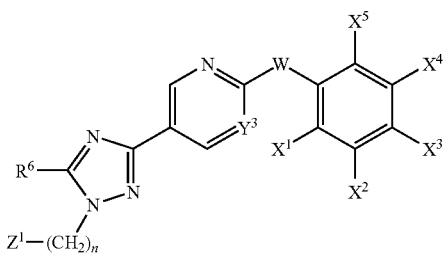

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

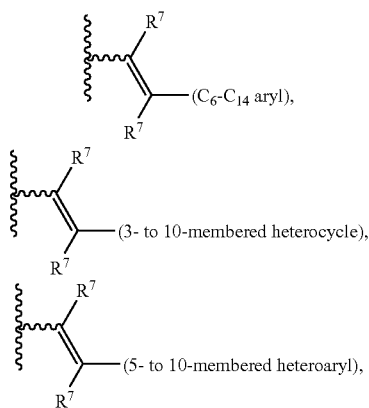

or a three- to ten-membered heterocycle; wherein any one nitrogen atom of any heterocycle containing one or more nitrogen atoms that may be substituted with a non-ring atom are substituted with —$(CH_2)_q Q$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_q Q$;

m is 0, 1, 2, 3, or 4;

q is 0, 1, 2, 3, or 4;

Q is hydrogen, $(C_1-C_6)$-alkyl, $(CH_2)_p CF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy $(C_1-C_3)$-alkyl, carbamoyl, or sulfamoyl;

each $R^6$ is independently hydrogen, methyl, trifluoromethyl, or amino; and each $R^7$ is independently hydrogen or methyl.

46. A compound of claim 45, wherein $Y^3$ is N and $R^6$ is hydrogen, methyl, or trifluoromethyl.

47. A compound of claim 45, wherein $Y^3$ is CH and $R^6$ is hydrogen, methyl, or trifluoromethyl.

48. A compound of claim 44, wherein the compound according to Formula (XV) comprises a compound according to Formula (XVII):

(XVII)

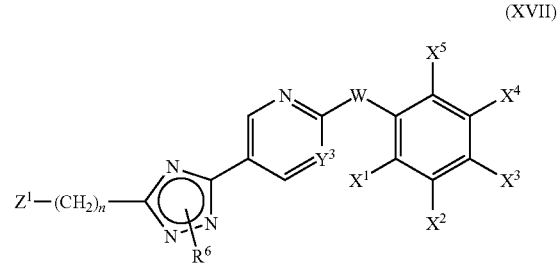

wherein:
each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

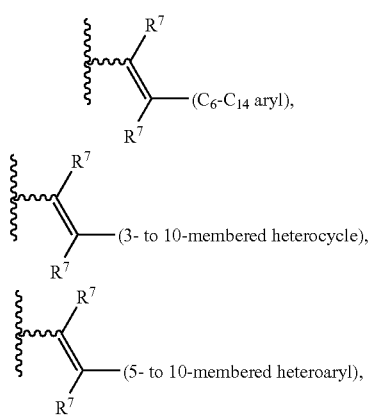

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

49. A compound of claim 48, wherein $Y^3$ is N and $R^6$ is hydrogen or methyl.

50. A compound of claim 48, wherein $Y^3$ is CH and $R^6$ is hydrogen or methyl.

51. A compound of claim 1, wherein the compound according to Formula (I) comprises a compound according to Formula (XVIII):

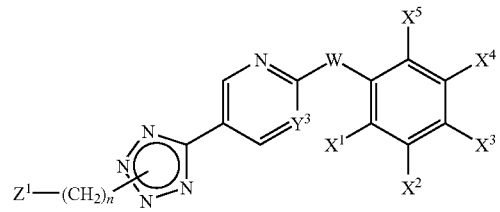

(XVIII)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

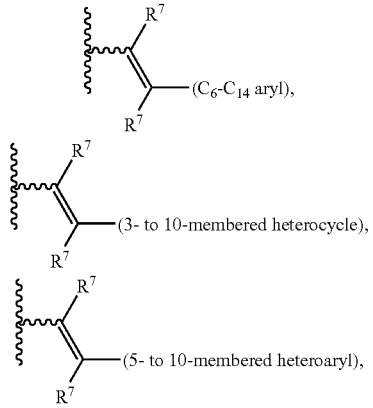

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-C_3)$-alkyl, $(C_1-C_3)$-alkylthio, trifluoromethyl, trifluoromethoxy, cyano, carboxy, carboxy$(C_1-C_3)$-alkyl, carbamoyl, or sulfamoyl;

each $R^6$ is independently hydrogen, methyl, trifluoromethyl, or amino; and each $R^7$ is independently hydrogen or methyl.

52. A compound of claim 51, wherein the compound according to Formula (XVIII) comprises a compound according to Formula (XIX):

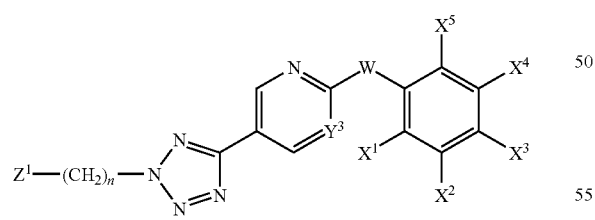

(XIX)

wherein:

each $X^1$, $X^2$, $X^3$, $X^4$, and $X^5$ is independently hydrogen or fluoro, with no more than two of $X^1$, $X^2$, $X^3$, $X^4$, and $X^5$ being fluoro;

W is a covalent bond, O, or CO;

n is 0, 1, 2, 3, or 4;

$Z^1$ is hydrogen, $OR^3$, $C(O)R^3$, $CO_2R^3$, $C(O)NR^4R^5$, $SO_2NR^4R^5$, $SO_2R^3$, $(C_1-C_6)$-alkyl, $(C_3-C_6)$-cycloalkyl, $(C_3-C_6)$-alkenyl, $(C_3-C_6)$-alkynyl, $(C_6-C_{14})$-aryl, $(CH_2)_p CF_3$, a five- to ten-membered heteroaryl,

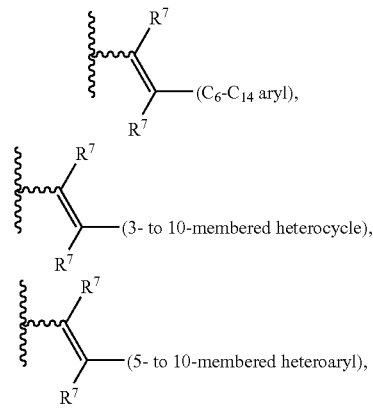

or a three- to ten-membered heterocycle; wherein any one nitrogen atom of any heterocycle containing one or more nitrogen atoms that may be substituted with a non-ring atom are substituted with —$(CH_2)_qQ$;

$R^3$ is hydrogen, $(C_1-C_6)$-alkyl, trifluoromethyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(five- to ten-membered heteroaryl), or $(CH_2)_m$(three- to ten-membered heterocycle), wherein any one nitrogen atom of any heterocycle containing one or more nitrogen atoms that may be substituted with a non-ring atom are substituted with —$(CH_2)_qQ$;

m is 0, 1, 2, 3, or 4;

q is 0, 1, 2, 3, or 4;

Q is hydrogen, $(C_1-C_6)$-alkyl, $(CH_2)_pCF_3$, $(C_3-C_6)$-alkenyl, $(C_3-C_6)$-alkynyl, $(C_3-C_6)$-cycloalkyl, $(C_6-C_{14})$-aryl, $C(O)R^3$, $CO_2R^3$, $C(O)NR^4R^5$, a three- to six-membered heterocycle, or a five- to ten-membered heteroaryl when q is 0, 1, 2, 3, or 4;

Q may also be cyano, trifluoromethyl, or $SO_2NR^4R^5$ when q is 1, 2, 3, or 4;

Q may also be hydroxy, $(C_1-C_6)$-alkoxy, sulfhydryl, —S—$(C_1-C_6)$-alkyl, or $NR^4R^5$ when q is 2, 3, or 4;

p is 1, 2, or 3;

$R^3$ may also be vinyl or ethynyl when $R^3$ is not covalently bonded to an N or O atom;

$R^3$ may also be vinyl or ethynyl when $R^3$ is not covalently bonded to an S atom possessing a −2 (minus 2) oxidation state;

$R^4$ and $R^5$ are independently hydrogen, $(C_1-C_6)$-alkyl, $(C_3-C_6)$-alkenyl, $(C_3-C_6)$-alkynyl, $(CH_2)_m(C_3-C_6)$-cycloalkyl, $(CH_2)_m$phenyl, $(CH_2)_m$-(three- to ten-membered heterocycyl), or $(CH_2)_m$-(five- to ten-membered heteroaryl);

the $NR^4R^5$ group of any $C(O)NR^4R^5$, $SO_2NR^4R^5$, $NR^4R^5$, or $N(H)C(O)NR^4R^5$ may also form a pyrrolidine, a piperidine, a morpholine, a thiomorpholine, or a thiomorpholine S-dioxide;

the $NR^4R^5$ group of any $C(O)NR^4R^5$, $SO_2NR^4R^5$, $NR^4R^5$, or $N(H)C(O)NR^4R^5$ may also form a piperazine ring, wherein the other nitrogen atom of the piperazine ring is substituted with hydrogen, $(C_1-C_6)$-alkyl, $CH_2CF_3$, $(C_3-C_6)$-cycloalkyl, $CH_2(C_3-C_6)$-cycloalkyl, phenyl, benzyl, hydroxyethyl, or hydroxypropyl;

phenyl or heteroaryl rings of $Z^1$ are optionally substituted with one-to-three of any one or combination of the following: halo, hydroxy, sulfhydryl, $(C_1-C_3)$-alkoxy, $(C_1-$ $C_3$)-alkyl, ($C_1$-$C_3$)-alkylthio, trifluoromethyl, trifluoromethoxy, cyano, carboxy, carboxy($C_1$-$C_3$)-alkyl, carbamoyl, or sulfamoyl;

each $R^6$ is independently hydrogen, methyl, trifluoromethyl, or amino; and each $R^7$ is independently hydrogen or methyl.

53. A compound of claim 52, wherein $Y^3$ is N.

54. A compound of claim 52, wherein $Y^3$ is CH.

55. A pharmaceutical composition comprising a compound of claim 1.

56. A method of treating a disease or condition mediated at least in part by prostaglandin $D_2$ produced by H-PGDS, in a subject in need of such treatment, wherein the disease or condition is allergy or allergic inflammation, comprising administering to the subject a therapeutically effective amount of a compound of claim 1.

57. A pharmaceutical composition comprising a compound of claim 1 and a second pharmacologically active compound.

* * * * *

UNITED STATES PATENT AND TRADEMARK OFFICE
CERTIFICATE OF CORRECTION

PATENT NO. : 8,536,185 B2  
APPLICATION NO. : 12/564582  
DATED : September 17, 2013  
INVENTOR(S) : Gregory W. Endres et al.

Page 1 of 1

It is certified that error appears in the above-identified patent and that said Letters Patent is hereby corrected as shown below:

In the Claims

Claim 1, Column 111, lines 14-15, delete "R1 is (C1-C6)-alkyl, (C3-C6)-cycloalkyl, phenyl, 2-pyridyl, 3-pyridyl, or 4-pyridyl;" replace with -- R1 is (C2-C6)-alkyl, (C3-C6)-cycloalkyl, phenyl, 2-pyridyl, 3-pyridyl, or 4-pyridyl; --

Signed and Sealed this  
Twenty-ninth Day of April, 2014

Michelle K. Lee  
*Deputy Director of the United States Patent and Trademark Office*